(12) United States Patent
Feilner et al.

(10) Patent No.: US 11,856,367 B2
(45) Date of Patent: Dec. 26, 2023

(54) HEARING SYSTEM, HEARING DEVICE AND METHOD FOR PROVIDING AN ALERT FOR A USER

(71) Applicant: SONOVA AG, Stäfa (CH)

(72) Inventors: Manuela Feilner, Egg b. Zürich (CH); Alexander Markus, Stäfa (CH)

(73) Assignee: Sonova AG, Stäfa (CH)

( * ) Notice: Subject to any disclaimer, the term of this patent is extended or adjusted under 35 U.S.C. 154(b) by 0 days.

(21) Appl. No.: 17/508,385

(22) Filed: Oct. 22, 2021

(65) Prior Publication Data

US 2022/0167099 A1 May 26, 2022

(30) Foreign Application Priority Data

Nov. 23, 2020 (EP) ..................................... 20209284

(51) Int. Cl.
*H04R 25/00* (2006.01)
*G06F 3/16* (2006.01)
*G08B 7/06* (2006.01)
*H04R 25/02* (2006.01)

(52) U.S. Cl.
CPC ........... *H04R 25/505* (2013.01); *G06F 3/165* (2013.01); *G08B 7/06* (2013.01); *H04R 25/02* (2013.01); *H04R 25/48* (2013.01); *H04R 2225/41* (2013.01); *H04R 2430/01* (2013.01); *H04R 2460/11* (2013.01)

(58) Field of Classification Search
None
See application file for complete search history.

(56) References Cited

U.S. PATENT DOCUMENTS

2016/0093207 A1\* 3/2016 Di Censo ............... G08G 1/005
340/944
2017/0188129 A1\* 6/2017 Sindia .................. H03G 3/3005
2017/0347348 A1\* 11/2017 Masaki .................... H04R 1/08
(Continued)

FOREIGN PATENT DOCUMENTS

DE 102019004867 A1 \* 1/2020
EP 3799443 3/2021
(Continued)

OTHER PUBLICATIONS

Machine translation of DE-102019004867-A1 (Year: 2019).\*
"Extended European Search Report received in EP Application No. 20209284.7-1210 dated May 12, 2021."

*Primary Examiner* — Walter F Briney, III
(74) *Attorney, Agent, or Firm* — ALG Intellectual Property, LLC

(57) ABSTRACT

A method of providing an alert for a user by a hearing device configured to be worn at an ear of the user includes providing user-related data including information about at least one of the user, an ambient environment of the user, or a property of the hearing device worn by the user; characterized by providing vehicle-related data associated with at least one vehicle in a vicinity of the user, the vehicle-related data including information about a property of the vehicle; determining, based on the user-related data and the vehicle-related data, a relevance measure indicative of a probability that the user is endangered by the vehicle; and controlling an operation of the hearing device depending on the relevance measure, the operation alerting the user about the vehicle.

19 Claims, 10 Drawing Sheets

(56) References Cited

U.S. PATENT DOCUMENTS

| | | |
|---|---|---|
| 2018/0286373 A1 | 10/2018 | O'Connell |
| 2018/0365982 A1 | 12/2018 | Kumar |
| 2019/0064344 A1 | 2/2019 | Turner |
| 2019/0215621 A1 | 7/2019 | Albahri |
| 2020/0174734 A1* | 6/2020 | Gomes .................... H04R 1/10 |
| 2021/0256952 A1* | 8/2021 | Seetharam ............... H04R 5/04 |

FOREIGN PATENT DOCUMENTS

| | | |
|---|---|---|
| WO | 2015048856 | 4/2015 |
| WO | 2020152323 | 7/2020 |
| WO | 2020152324 | 7/2020 |
| WO | 2020224914 | 11/2020 |

* cited by examiner

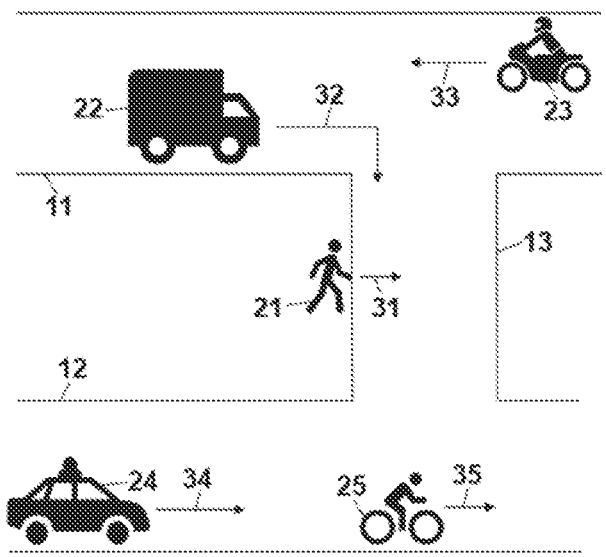
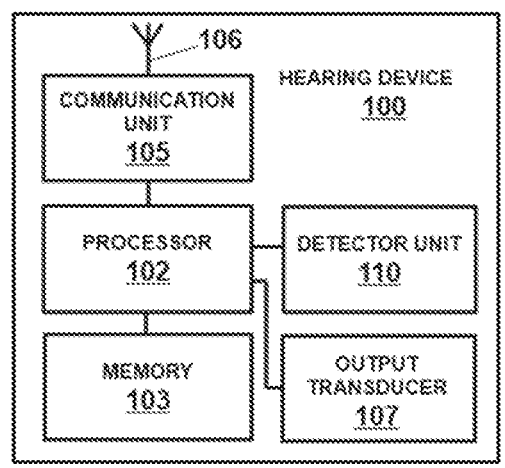
Fig. 1
Fig. 2
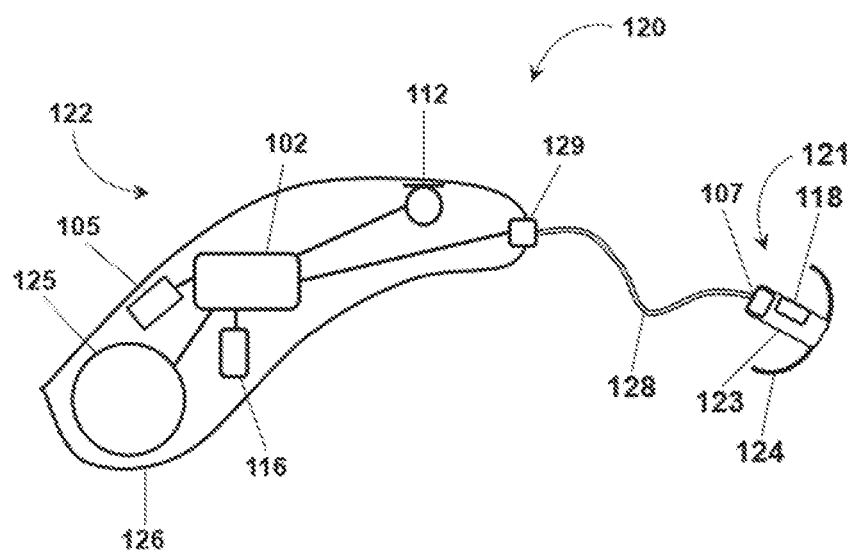
Fig. 3

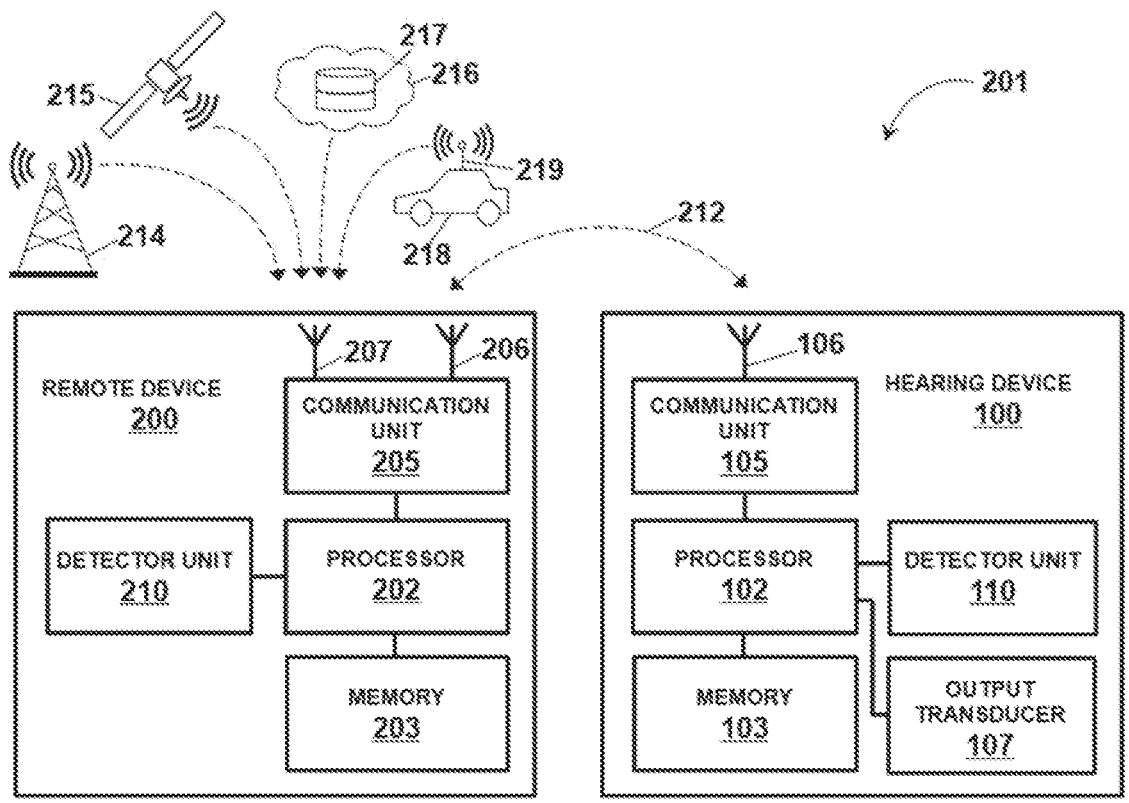
Fig. 4
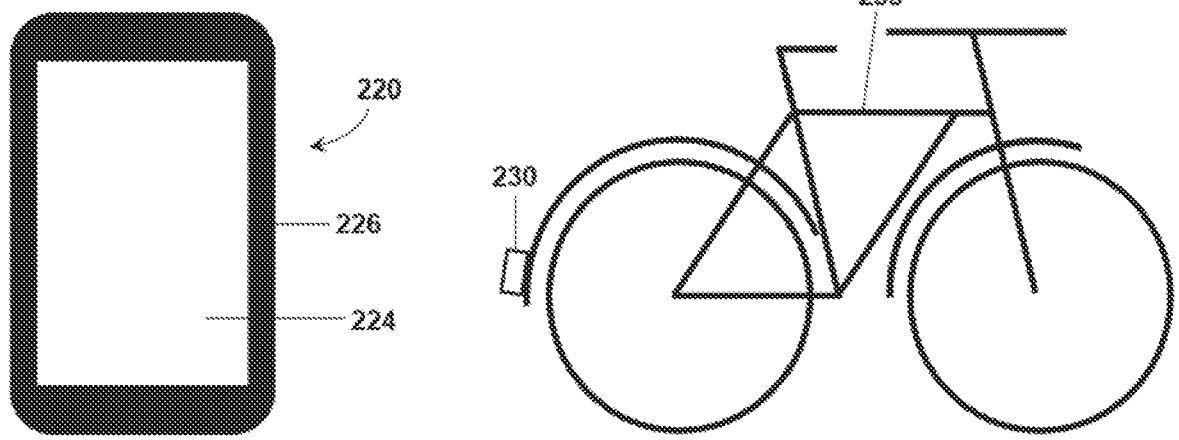
Fig. 5                    Fig. 6

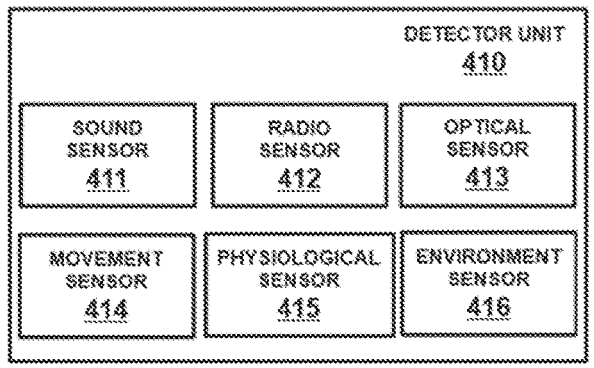
Fig. 7
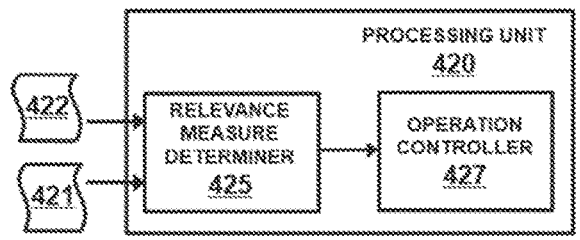
Fig. 8
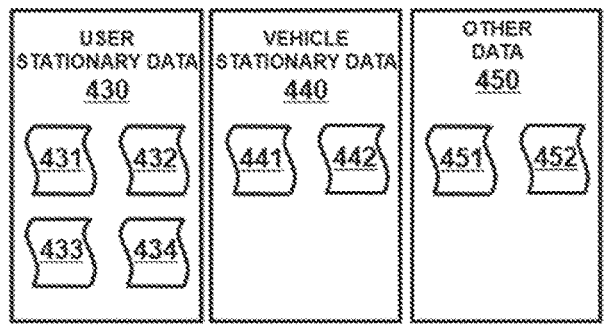
Fig. 9
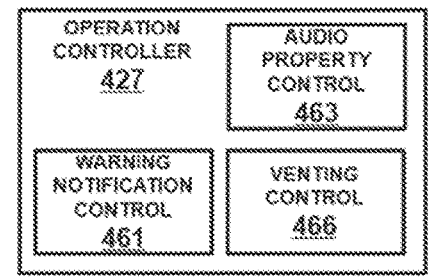
Fig. 10
Fig. 11
Fig. 12

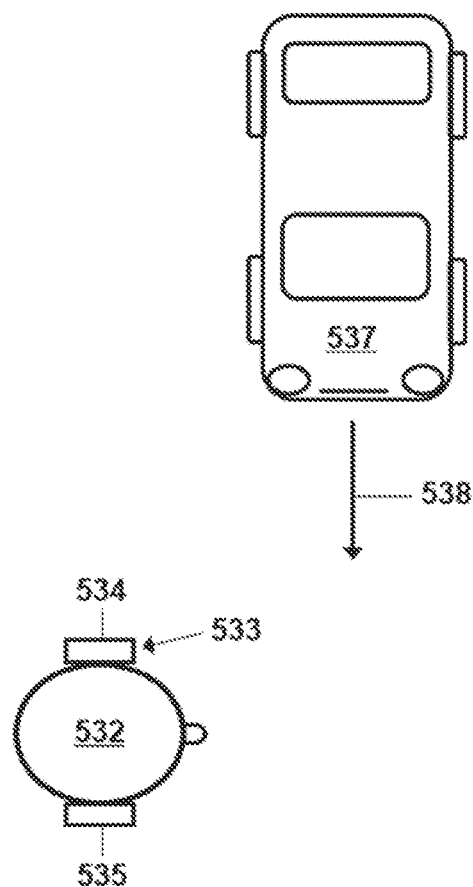
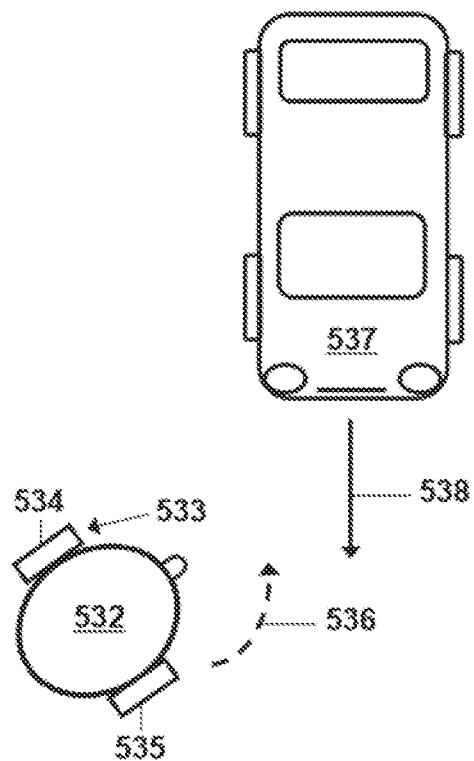
Fig. 21A  Fig. 21B
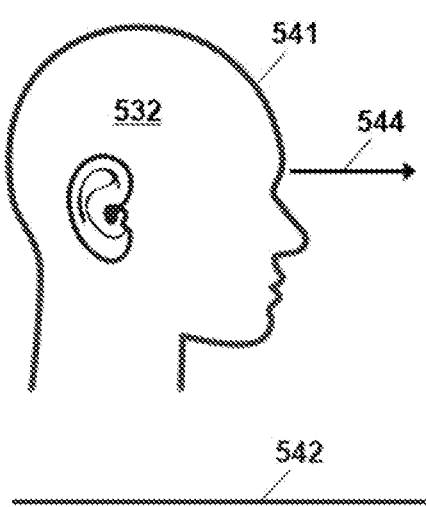
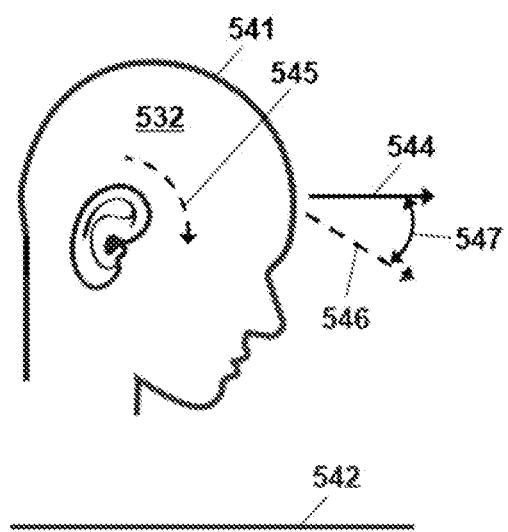
Fig. 22A  Fig. 22B

HEARING SYSTEM, HEARING DEVICE AND METHOD FOR PROVIDING AN ALERT FOR A USER

RELATED APPLICATIONS

The present application claims priority to EP Patent Application No. 20209284.7, filed Nov. 23, 2020, the contents of which are hereby incorporated by reference in their entirety.

BACKGROUND INFORMATION

Hearing devices may be used to improve the hearing capability or communication capability of a user, for instance by compensating a hearing loss of a hearing-impaired user, in which case the hearing device is commonly referred to as a hearing instrument such as a hearing aid, or hearing prosthesis. A hearing device may also be used to output sound based on an audio signal which may be communicated by a wire or wirelessly to the hearing device. A hearing device may also be used to reproduce a sound in a user's ear canal detected by a microphone. The reproduced sound may be amplified to account for a hearing loss, such as in a hearing instrument, or may be output without accounting for a hearing loss, for instance to provide for a faithful reproduction of detected ambient sound and/or to add sound features of an augmented reality in the reproduced ambient sound, such as in a hearable. Different types of hearing devices configured to be worn at an ear include earbuds, earphones, hearables, and hearing instruments such as receiver-in-the-canal (RIC) hearing aids, behind-the-ear (BTE) hearing aids, in-the-ear (ITE) hearing aids, invisible-in-the-canal (IIC) hearing aids, completely-in-the-canal (CIC) hearing aids, cochlear implant systems configured to provide electrical stimulation representative of audio content to a user, a bimodal hearing system configured to provide both amplification and electrical stimulation representative of audio content to a user, or any other suitable hearing prostheses.

Hearing devices are often employed in conjunction with communication devices, such as smartphones or tablets, for instance when listening to sound data processed by the communication device and/or during a phone conversation operated by the communication device. More recently, communication devices have been integrated with hearing devices such that the hearing devices at least partially comprise the functionality of those communication devices. A hearing system may comprise, for instance, a hearing device and a communication device.

In recent times, some hearing devices are also increasingly equipped with different sensor types. Traditionally, those sensors often include a sound sensor to detect a sound and to output an amplified and/or signal processed version of the sound to the user. In an effort to provide the user with even more information about himself and/or the ambient environment, various other sensor types are progressively implemented, in particular sensors which are not directly related to the sound reproduction and/or amplification function of the hearing device. Those sensors include inertial sensors, such as accelerometers, allowing to monitor the user's movements. Physiological sensors, such as biometric sensors, are mostly employed for monitoring the user's health.

Hearing impairment and/or wearing a hearing device for listening to an audio content can pose an increased safety risk in road traffic. A user wearing the hearing device may recognize approaching vehicles only with considerable delay or overlook the vehicles due to an adversely affected sense of hearing. Vulnerable road users include, for instance, pedestrians, bicyclists, and car drivers. Various sensing and communication capabilities of a hearing device, as mentioned above, may be employed to assess a risk for the user in a current traffic situation which may be posed by a vehicle in a vicinity of the user. Where such a risk is discovered, an appropriate alert may be provided to the user by the hearing device.

Apart from the challenge to reliably identify a potentially dangerous vehicle in a vicinity of the user, there remains another challenge of not annoying and/or overloading the user with too many and/or unnecessary alerts. In many cases, the user may already be aware of the vehicle. In such a case, the alert can be perceived as a disturbance rather than being helpful. Moreover, alerting the user about a specific vehicle may even increase the traffic risk, for instance when the user has already noticed this vehicle but the alert distracts the user from another potentially dangerous vehicle escaping the user's attention. Optimally, the alert would be restricted only to those circumstances in which it is really needed, and only to an extent which is required to catch the user's attention. Quantitatively defining such a restriction, however, which may be experienced rather subjectively and may also depend on the user's preferences and other unpredictable properties of the user and the traffic environment, can be hard to achieve in practice without compromising the user's interests of being reliably alerted and not being annoyed by the alert. It would therefore be desirable to approximate the user's interests as accurate as possible, and to satisfy the user's needs within the underlying technical constraints.

BRIEF DESCRIPTION OF THE DRAWINGS

Reference will now be made in detail to embodiments, examples of which are illustrated in the accompanying drawings. The drawings illustrate various embodiments and are a part of the specification. The illustrated embodiments are merely examples and do not limit the scope of the disclosure. Throughout the drawings, identical or similar reference numbers designate identical or similar elements. In the drawings:

FIG. 1 schematically illustrates an exemplary traffic situation;

FIG. 2 schematically illustrates an exemplary hearing device configured to be worn at an ear of a user, the hearing device including a processor, a detector unit, a communication unit, and an audio transducer;

FIG. 3 schematically illustrates some embodiments of the hearing device illustrated in FIG. 2 in the form of a RIC hearing aid;

FIG. 4 schematically illustrates an exemplary hearing system comprising the hearing device illustrated in FIG. 2, and an electronic device communicatively coupled to the hearing device;

FIGS. 5, 6 schematically illustrate some embodiments of an electronic device which may be implemented by the electronic device illustrated in FIG. 4;

FIG. 7 schematically illustrates an exemplary detector unit, which may be implemented in the hearing device illustrated in FIGS. 2, 4 and/or in the electronic device illustrated in FIG. 4;

FIG. 8 schematically illustrates some exemplary configurations of the hearing device illustrated in FIG. 2 and/or the hearing system illustrated in FIG. 4 to determine a relevance measure, and to control an operation alerting the user about a vehicle depending on the relevance measure;

FIG. 9 schematically illustrates different categories of user-related data and vehicle-related data;

FIG. 10 schematically illustrates different operations that may be performed by the hearing device illustrated in FIGS. 2, 4 to alert the user about a vehicle;

FIG. 11 schematically illustrates different properties of an audio signal that may be outputted to the user by the hearing device illustrated in FIGS. 2, 4;

FIG. 12 schematically illustrates different properties of a venting channel that may be included in the hearing device illustrated in FIGS. 2, 4;

FIGS. 21A, B schematically illustrate an exemplary traffic situation during which user-related data can be obtained by the hearing device illustrated in FIGS. 2, 4 and/or the electronic device illustrated in FIG. 4 based on a movement of the user;

FIGS. 22A, B schematically illustrate another exemplary traffic situation during which user-related data can be obtained by the hearing device illustrated in FIGS. 2, 4 and/or the electronic device illustrated in FIG. 4 based on a movement of the user;

DETAILED DESCRIPTION

Figure 13:
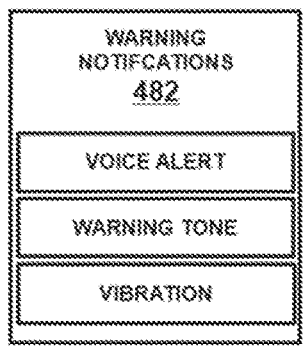
FIG. 13 schematically illustrates different warning notifications that may be outputted to the user by the hearing device illustrated in FIGS. 2, 4.

The disclosure relates to a method of providing an alert for a user by a hearing device configured to be worn at an ear of the user.

It is a feature of the present disclosure to avoid at least one of the above mentioned disadvantages and to equip a hearing device and/or a hearing system with a capability to control an alert for the user by the hearing device about a vehicle in a vicinity of the user in a convenient way, in particular to balance the user's interests of reliably becoming alerted about a potentially risky traffic situation and of not being overloaded or annoyed by too many or needless alerts. It is another feature to adapt the user's awareness evoked by the alert to a probability that the user is actually endangered by the vehicle, in particular to minimize a potential disturbance of the user caused by the alert. It is a further feature to facilitate recognition of a danger zone by the user, for instance to provide the alert in a way drawing the user's attention toward a direction from which the endangerment originates and/or to a spatial and/or a temporal distance of the danger relative to the user. It is yet another feature to allow a prioritization of a vehicle about which the user is alerted, in particular in a case in which multiple vehicles are present in the vicinity of the user. It is still another feature to allow the user and/or a third party to customize the alert operation and/or the occurrence of the alert operation in accordance with personal requirements and/or favorable boundary conditions.

Accordingly, the present disclosure proposes a method of providing an alert for a user by a hearing device configured to be worn at an ear of the user, the method comprising providing user-related data including information about the user and/or an ambient environment of the user and/or a property of the hearing device worn by the user; providing vehicle-related data associated with at least one vehicle in a vicinity of the user, the vehicle-related data including information about a property of the vehicle; determining, based on the user-related data and the vehicle-related data, a relevance measure indicative of a probability that the user is endangered by the vehicle; and controlling an operation of the hearing device depending on the relevance measure, the operation alerting the user about the vehicle.

In this way, information contained in the user-related data may be put in a mutual context with information contained in the vehicle-related data to determine a probability that the user is endangered by the vehicle, and to control an alert operation depending thereon. This may be employed, in some instances, to restrict the alert to situations in which the user is not already aware of an imminent danger and/or in which a probability of the vehicle impacting the user is high enough. This may also be employed, in some instances, to provide the alert in a way in which a disturbance of the user by the alert can be minimized depending on the probability that the user is endangered by the vehicle, in particular by still ensuring that the user becomes aware of the alert, at least when a probability of the vehicle impacting the user is high enough.

Independently, the present disclosure proposes a hearing system comprising a hearing device configured to be worn at an ear of a user; and an electronic device configured to be operated stationary with the user remote from the ear, the electronic device communicatively coupled to the hearing device, wherein the hearing system includes a processing unit configured to perform the method of providing the alert. Independently, the present disclosure proposes a hearing device configured to be worn at an ear of a user, the hearing device comprising a processing unit configured to perform the method of providing the alert. Independently, the present disclosure proposes a non-transitory computer-readable medium storing instructions that, when executed by a processing unit, cause the processing unit to perform the method of providing the alert.

Subsequently, additional features of some implementations of the method and/or the hearing system and/or the hearing device are described. Each of those features can be provided solely or in combination with at least another feature. The features can be correspondingly provided in some implementations of the method and/or the hearing system and/or the hearing device and/or the computer-readable medium.

In some implementations, the vehicle-related data and/or the user-related data is employed to determine a probability that a vehicle in a vicinity of the user will impact the user and/or a probability that the user is aware of a vehicle in its vicinity. The relevance measure may be determined based on the probability that the vehicle will impact the user and/or the probability that the user is aware of the vehicle.

The vehicle-related data may include information about a dynamic property and/or an intrinsic property of the vehicle. The dynamic property of the vehicle may comprise a location of the vehicle and/or a speed of the vehicle and/or a moving direction of the vehicle and/or an itinerary of the vehicle and/or a distance and/or proximity of the vehicle relative to the user and/or a predicted impact location of the vehicle with the user and/or a presence and/or number of vehicles in the vicinity of the user. The intrinsic property of the vehicle may comprise a type of the vehicle and/or a recognizability of the vehicle and/or a magnitude of harm the vehicle may potentially inflict on the user.

The vehicle-related data may be detected by a detector included in the hearing device and/or a detector included in the electronic device remote from the hearing device and/or may be communicated to the hearing device and/or to the electronic device from an external data source distant from the user, for instance via a radio frequency (RF) signal. The hearing device and/or the electronic device may include a communication unit to receive the data from the external data source.

User-related data may include information about a dynamic and/or intrinsic property of the user and/or the ambient environment of the user. The dynamic property of the user may comprise a location of the user and/or a speed of the user and/or a moving direction of the user and/or an itinerary of the user and/or a distance and/or proximity of the user relative to the vehicle and/or an orientation of the user relative to the vehicle. The intrinsic property of the user may comprise a property of a vehicle driven by the user, for instance a type of the vehicle and/or a recognizability of the vehicle and/or a traffic safety of the vehicle. The intrinsic property of the user may comprise a level of awareness of the user about a vehicle in its vicinity. The level of awareness may be determined based on a property of an audio signal outputted to the user by an audio transducer included in the hearing device and/or a property of an ambient environment of the user and/or a behavior of the user and/or a condition of the user.

The user-related data includes information about the user and/or an ambient environment of the user and/or a property of the hearing device worn by the user, which may comprise information about a property of the hearing device impacting the user when the hearing device is worn by the user. The user-related data may include information obtained at the ear when the hearing device is worn by the user, in particular when the hearing device is operated by the user at the ear of the user. The user-related data may also include information about an electronic device communicatively coupled to the hearing device.

For instance, the property of the audio signal may include a type and/or an origin and/or a volume and/or a directivity and/or a timing and/or a content of the audio signal and/or an amount of the content and/or a frequency of a sound represented by the audio signal and/or a noise cancelling performed by the audio signal. The property of the ambient environment may be detected by an environment sensor. The property of the ambient environment may include information about a current traffic situation and/or a road environment and/or a road condition and/or a weather and/or a visibility and/or daylight conditions and/or a volume level and/or a noise level prevailing in the ambient environment. The property of the ambient environment may also include a presence of a sound feature in a sound detected in the ambient environment, wherein the sound feature is indicative of a sound in the ambient environment suitable to affect the user's awareness.

The behavior of the user may be detected, for instance, by a movement sensor and/or a sound sensor and/or a physiological sensor, in particular a biometric sensor. The behavior of the user may include, for instance, a movement of the user, in particular a movement of the user's body and/or the user's head and/or the user's eye gaze, which may include a translational and/or a rotational movement. The movement of the user may also comprise a pattern of a movement, for instance a pattern indicative of a walking activity and/or a cycling activity and/or a skating activity and/or an activity of the user riding a scooter. The behavior of the user may also comprise information about a sound, in particular an own voice activity of the user. The behavior of the user may also be determined based on information about a biometric property, for instance a changing heart rate and/or brainwaves detected on the user.

The condition of the user may be detected, for instance, by a movement sensor and/or a sound sensor and/or a physiological sensor, in particular a biometric sensor. The condition of the user may include, for instance, a level of fatigue of the user and/or a health condition of the user. The level of fatigue may be determined based on data provided by a movement sensor and/or a physiological sensor, in particular a biometric sensor. The level of fatigue may include a level of physical fatigue and/or mental fatigue. For instance, movement data provided by the movement sensor can indicate a physical exhaustion of the user, in particular when performed for a minimum time. Biometric data provided by a biometric sensor can indicate a heart rate and/or a blood pressure and/or a heart rate variability (HRV) representing a current physical exhaustion and/or mental stress level impacting the user's fatigue. A mental status of fatigue, for instance a cognitive load and/or lack of sleep, may also be determined by biometric data provided by a biometric sensor. The level of fatigue may also be determined based on sound data provided by a sound sensor. In particular, a voice of the user may indicate a physical and/or emotional condition of the user impacting its fatigue. The sound data may be analyzed with respect to a sound feature contained in the sound data indicating the user's fatigue. The health condition of the user may comprise a hearing loss and/or a fitness level and/or a narcotization level of the user. The health condition may be determined based on a setting of the hearing device and/or physiological data, in particular biometric data.

In some instances, the user-related data comprises data indicative of a property detected on the user and/or in an ambient environment of the user. The data may be detected by a detector included in the hearing device and/or in the electronic device remote from the hearing device. Detecting the property of the user by the hearing device can offer the advantage to exploit advantageous anatomical characteristics of the ear to perform a measurement on the user, in particular when biometric and/or movement measurements are performed. Those favorable anatomical ear characteristics may comprise, for instance, a proximity to the user's brain and/or a good blood circulation and/or a rather dark environment inside the ear canal and/or a location at the head such that head movements can be accounted for. Detecting the property of the ambient environment of the user by the hearing device can offer the advantage to exploit an advantageous position at the ear to perform a measurement of the ambient environment, in particular at a rather high altitude relative to other body parts of the user. Accordingly, the hearing device may comprise a detector configured to detect a property on the user and/or in an ambient environment of the user. The detector may include a sound sensor and/or a radio sensor and/or an optical sensor and/or a movement sensor and/or a physiological sensor and/or an environment sensor. The physiological sensor may be provided as a biometric sensor. The electronic device may also comprise a detector configured to detect a property on the user and/or in an ambient environment of the user, in particular a sound sensor and/or a radio sensor and/or an optical sensor and/or a movement sensor and/or a physiological sensor and/or an environment sensor.

In some instances, the user-related data comprises data indicative of a property of the hearing device and/or the electronic device remote from the hearing device. The data indicative of a property of the hearing device may include data indicative of a property of an audio signal outputted to the user by an audio transducer included in the hearing device and/or data indicative of an effective size of a venting channel included in the hearing device, the venting channel configured to provide for venting between an inner region of an ear canal of the ear and an ambient environment outside the ear canal depending on the effective size, and/or data indicative of a current setting of the hearing device. In some instances, the user-related data comprises data communicated to the hearing device and/or the electronic device from an external data source distant from the user, for instance via an RF signal. Accordingly, the hearing device and/or electronic device may comprise a communication unit including at least one communication port to receive the communicated data.

The user-related data and the vehicle-related data may be different data. This may allow to determine the relevance measure at a higher accuracy. The user-related data and the vehicle-related data may also be the same data, wherein a different information related to a property of the vehicle and to a property of the user and/or to the ambient environment of the user may be obtained from the data. To illustrate, a detected sound may include information about a property of the vehicle, which may be based on a sound emitted by the vehicle, and information about a property of the user, for instance a voice of the user, and/or information about a property of the ambient environment, for instance a noise level of the environment.

In some implementations, the method further comprises determining whether the user-related data and/or the vehicle-related data fulfills a condition, wherein the relevance measure is determined depending on the condition being fulfilled, wherein the condition is customizable during operating the hearing device and/or an electronic device configured to be communicatively coupled to the hearing device. This can allow the user and/or a third party to customize the alert operation and/or the occurrence of the alert operation. In some instances, the condition is customizable by data provided via a user interface. The user interface can be provided stationary with the user. For instance, the hearing device and/or the electronic device may comprise the user interface. The user interface can be communicatively coupled to the processing unit. In some instances, the condition is customizable by data communicated from a data source distant from the user. The data may be communicated to the hearing device and/or electronic device. The hearing device and/or electronic device may comprise a communication unit configured to receive the data. The communication unit can be communicatively coupled to the processing unit. The condition may restrict a context in which the operation is controlled.

For instance, the condition may restrict the operation to be controlled at a specific location; and/or a time; and/or a weather; and/or a traffic volume; and/or a visibility range; and/or an audibility of sound in the environment; and/or a property of an audio signal outputted to the user by an audio transducer included in the hearing device; and/or a property of a sound detected in an environment of the user, e.g. the user's voice and/or a volume level; and/or a physiological property of the user, e.g. a level of fatigue and/or health condition; and/or an age of the user; and/or a movement property of the user; and/or a transportation means, in particular a vehicle, employed by the user; and/or an orientation and/or a distance and/or a speed of the user relative to the vehicle in the vicinity of the user; and/or a property of the vehicle in the vicinity of the user; and/or a minimum number of vehicles in the vicinity of the user.

In some implementations, the operation alerting the user about the vehicle comprises modifying, when an audio signal is outputted to the user by an audio transducer included in the hearing device, a property of the outputted audio signal; and/or adjusting an effective size of a venting channel included in the hearing device, the venting channel configured to provide for venting between an inner region of an ear canal of the ear and an ambient environment outside the ear canal depending on the effective size; and/or initiate outputting an audio signal to the user by an audio transducer included in the hearing device; and/or initiate a vibration of the hearing device evoking a tactile perception by the user. The audio signal initiated to be outputted may represent sound data indicative of a sound detected in the ambient environment of the user and/or may include a warning notification for the user.

In some implementations, the hearing device is configured to receive an audio signal communicated from an external audio source, wherein, when the audio signal is outputted to the user by an audio transducer included in the hearing device, the operation alerting the user about the vehicle comprises reducing a volume level of the outputted audio signal; and/or outputting an audio signal representative of a sound detected in the ambient environment of the user; and/or outputting a warning notification to the user;

and/or terminating outputting the audio signal to the user. In this way, a distracting effect of the audio signal communicated from the external audio source may be mitigated allowing the user to focus its attention to the current traffic situation. The hearing device and/or electronic device may comprise a communication unit configured to receive the audio signal from the external audio source, for instance via an RF signal.

In some implementations, the operation alerting the user about the vehicle comprises modifying, before an audio signal is outputted to the user by an audio transducer included in the hearing device, a directivity of the outputted audio signal such that the directivity points toward a location of the vehicle and/or a moving direction of the vehicle and/or an itinerary of the vehicle. In particular, the directivity may be modified depending on a dynamic property of the vehicle and/or a dynamic property of the vehicle relative to a dynamic property of the user. In this way, the user's attention can be drawn toward a direction from which the endangerment originates.

In some implementations, the operation alerting the user about the vehicle comprises modifying, before an audio signal is outputted to the user by an audio transducer included in the hearing device, a volume level of the outputted audio signal and/or a volume level of a sound feature contained in the outputted audio signal, the sound feature representing a sound emitted by the vehicle in the vicinity of the user, depending on a distance of the vehicle to the user and/or a type of the vehicle and/or a speed of the vehicle and/or a direction from which the vehicle is approaching the user. In this way, the user's attention may be drawn to a distance of the danger relative to the user and/or another property of the vehicle affecting the danger for the user.

In some implementations, the operation alerting the user about the vehicle comprises modifying, before an audio signal is outputted to the user by an audio transducer included in the hearing device, a frequency of a sound feature contained in the outputted audio signal, the sound feature representing a sound emitted by the vehicle in the vicinity of the user. For instance, when more than one vehicle is present in the vicinity of the user, modifying the frequency of the sound emitted by one of the vehicles can help the user to recognize this vehicle from the plurality of vehicles.

In some implementations, the operation alerting the user about the vehicle comprises attenuating, before an audio signal is outputted to the user by an audio transducer included in the hearing device, a volume level of a first sound feature in the audio signal relative to a volume level of a second sound feature in the audio signal, the second sound feature representing a sound emitted by the vehicle in the vicinity of the user. In this way, the user's awareness about a potentially dangerous situation may be evoked by emphasizing the second sound feature relative to the first sound feature.

In some implementations, the operation alerting the user about the vehicle comprises superimposing, before an audio signal containing a first sound feature is outputted to the user by an audio transducer included in the hearing device, a second sound feature to the audio signal, the second sound feature suitable to attract the user's attention from the first sound feature when perceiving the outputted audio signal. In particular, the second sound feature may augment the audio signal by including a sound alerting the user about a potentially risky traffic situation. For instance, the second sound feature may be implemented as an alarm tone, a voice alert and/or the like.

For instance, the audio signal may represent a sound detected in the ambient environment and/or an audio signal communicated from an external audio source, for example a phone call signal provider and/or a streaming media provider.

In some implementations, the operation is a first operation, the method further comprising controlling a second operation of the hearing device depending on the relevance measure, the second operation alerting the user about the vehicle, wherein the first operation is selected to be controlled when the relevance measure is determined to have a first value, and the second operation is selected to be controlled when the relevance measure is determined to have a second value, wherein the first value is indicative of a smaller probability that the user is endangered by the vehicle than the second value. In this way, a disturbance of the user by the alert can be minimized depending on the probability that the user is endangered by the vehicle.

In some implementations, the vehicle-related data is first vehicle-related data associated with a first vehicle in the vicinity of the user, and the relevance measure is a first relevance measure indicative of a probability that the user is endangered by the first vehicle, wherein the method further comprises providing second vehicle-related data associated with a second vehicle in the vicinity of the user, the second vehicle-related data including information about a property of the second vehicle; and determining, based on the user-related data and the second vehicle-related data, a second relevance measure indicative of a probability that the user is endangered by the second vehicle, wherein the operation of the hearing device is controlled depending on the first relevance measure and the second relevance measure. This may be employed to prioritize a vehicle from a plurality of vehicles about which the user is alerted. A confusion of the user about too many alerts may thus be avoided.

In some instances, when the first relevance measure is indicative of a higher value of said probability as compared to the second relevance measure, a first operation alerting the user about the first vehicle is controlled, and, when the second relevance measure is indicative of a higher value of said probability as compared to the first relevance measure, a second operation alerting the user about the second vehicle is controlled. Controlling the first operation may comprise executing the first operation and/or preventing the second operation from being executed, and controlling the second operation may comprise executing the second operation and/or preventing the first operation from being executed.

In some instances, a prioritization measure may be determined depending on the first relevance measure and the second relevance measure. The prioritization measure may include information which vehicle from a plurality of vehicles shall be prioritized when the operation is controlled. The operation may then be controlled depending on the prioritization measure. In some instances, the operation may further be controlled depending on the relevance measure determined for the prioritized vehicle. In particular, a first operation alerting the user about the first vehicle and a second operation alerting the user about the second vehicle may be controlled depending on the prioritization measure and the relevance measure. For instance, when the first and second relevance measure are both indicative of a rather low value of said probability, neither the first operation may be controlled nor the second operation may be controlled to be executed irrespective of the prioritization measure.

In some implementations, the user-related data comprises movement data indicative of a movement of the user and/or physiological data indicative of a physiological property of the user and/or sound data indicative of a detected sound, wherein the method further comprises determining a probability that the user is aware of the vehicle based on the user-related data, wherein the relevance measure is determined depending on the probability that the user is aware of the vehicle. In some instances, the method may comprise determining a level of fatigue of the user based on the user-related data, wherein the probability that the user is aware of the vehicle is determined depending on the level of fatigue. In some instances, the method may comprise determining a health condition of the user based on the user-related data, wherein the probability that the user is aware of the vehicle is determined depending on the health condition. In some instances, the method may comprise determining a behavior of the user based on the user-related data, wherein the probability that the user is aware of the vehicle is determined depending on the behavior.

In some implementations, the vehicle-related data comprises sound data including information about a sound emitted by the vehicle and/or data obtained from an RF-signal communicated from the vehicle. The hearing device and/or remote device may include a communication unit configured to receive the RF-signal. In some instances, the sound data may be detected stationary with the user. The hearing device and/or remote device may include a sound sensor configured to detect the sound in an ambient environment of the user. In some instances, the sound data may be detected stationary with the vehicle, wherein the RF-signal contains data representative of the sound data. In some implementations, a dynamic property of the vehicle is determined from the sound data and/or the data obtained from the RF-signal. In some instances, a received signal strength indicator (RSSI) of the RF-signal may be determined. In some instances, the sound data may be detected stationary with the user at both ears of the user, wherein an interaural phase difference (IPD) and/or an interaural time difference (ITD) and/or an interaural level difference (ILD) may be determined. In some instances, the sound data detected stationary with the user may be compared with the sound data detected stationary with the vehicle, based on the received RF-signal.

In some implementations, the vehicle-related data comprises information about a location of the vehicle and/or a speed of the vehicle and/or a moving direction of the vehicle and/or an itinerary of the vehicle and/or a distance of the vehicle relative to the user, wherein the relevance measure is determined depending on the location of the vehicle and/or the speed of the vehicle and/or the moving direction of the vehicle and/or the itinerary of the vehicle and/or the distance of the vehicle relative to the user, and/or the relevance measure is determined depending on a probability that a future location of the vehicle is likely to coincide with a future location of the user. In some instances, an impact location is defined as a location at which a future location of the vehicle is likely to coincide with a future location of the user, wherein the method further comprises predicting the impact location. For instance, the prediction may be based on the intercept theorem.

In some implementations, the user-related data comprises rotation data indicative of a rotation of the user and/or ocular data indicative of an eye gaze movement of the user and/or orientation data indicative of an orientation of the user, wherein the method further comprises determining a direction of the rotation and/or the eye gaze movement and/or the orientation relative to a location of the vehicle and/or a moving direction of the vehicle and/or an itinerary of the vehicle, wherein the relevance measure is determined to be indicative of a reduced value of said probability when said direction points toward the location of the vehicle and/or the moving direction of the vehicle and/or the itinerary of the vehicle.

In some implementations, the user-related data comprises orientation data indicative of an orientation of the user's head, wherein the method further comprises determining a direction of the orientation of the user's head relative to the surface of the earth, wherein the relevance measure is determined to be indicative of an increased value of the probability that the user is endangered by the vehicle when said direction deviates from a direction parallel to the surface of the earth by more than a predefined angle.

In some implementations, the user-related data comprises movement data indicative of a movement of the user, in particular a translational movement, wherein the method further comprises determining a direction and/or a speed of the movement, wherein the relevance measure is determined to be indicative of a reduced value of the probability that the user is endangered by the vehicle when said direction and/or speed changes.

In some implementations, the user-related data comprises movement data indicative of a movement of the user, in particular a translational movement, wherein the method further comprises determining a speed of the movement, wherein the relevance measure is determined to be indicative of an increased value of said probability when said speed is determined to have a larger value as compared to when said speed is determined to have a smaller value.

In some implementations, the user-related data comprises walking data indicative of a walking activity of the user and/or cycling data indicative of a cycling activity of the user and/or skating data indicative of a skating activity of the user and/or scooter data indicative of an activity of the user riding a scooter, wherein the method further comprises determining a pattern of the walking activity and/or cycling activity and/or skating activity and/or activity of riding a scooter, wherein the relevance measure is determined to be indicative of a reduced value of said probability when said pattern changes.

In some implementations, the vehicle-related data and/or user-related data comprises sound data indicative of a sound detected in the ambient environment of the user, wherein the method further comprises determining whether the sound data contains a sound feature associated with a property of a vehicle and/or a property of the user, wherein the relevance measure is determined depending on the sound data containing the sound feature. In some instances, the relevance measure can be indicative of an increased value of said probability when the sound data contains the sound feature. For instance, the sound feature may be indicative of a type of a vehicle posing a potential danger to the user.

In some implementations, the sound feature is indicative of a sound emitted by the vehicle as detected by a sound detector stationary with the user, the method further comprising determining a frequency of said sound, wherein the relevance measure is determined depending on the frequency of said sound. To illustrate, the sound emitted by the vehicle, as perceived by a person stationary with the vehicle, can be frequency-shifted relative to the corresponding sound detected by the sound detector stationary with the user depending on a velocity of the vehicle relative to the user. The phenomenon can be understood in terms of the Doppler effect referring to a change in frequency of a wave in relation to an observer who is moving relative to the wave source. Thus, the frequency of the sound emitted by the vehicle as detected by the sound detector stationary with the user can indicate the velocity of the vehicle relative to the user. For instance, the sound feature may be identified based on determining whether the sound detected by the sound detector stationary with the user matches a sound pattern characteristic for the sound emitted by the vehicle. The sound pattern may include any characteristic variations of the sound in time and/or frequency which can be recognized irrespective of a frequency shift caused by a movement of the vehicle relative to the user, in particular by the Doppler effect. Such a sound pattern may be recognized by any sound recognition algorithm, for instance an algorithm in which the sound pattern is predetermined and/or adaptively changed. For instance, a machine learning algorithm may be employed, which may be trained based on the sound emitted by the vehicle recorded at different velocities of the vehicle relative to the reference frame in which the sound is recorded. To give a specific example, the sound feature may correspond to a sound of a siren of an emergency vehicle. The sound pattern may then be characteristic for acoustic variations of the siren in time and/or frequency which can be recognized irrespective of a frequency shift caused by the Doppler effect.

In some implementations, the method further comprises comparing the frequency of the sound emitted by the vehicle as detected by the sound detector stationary with the user with a reference frequency, wherein the relevance measure is determined depending on the comparison. To illustrate, the reference frequency may correspond to a frequency of the sound emitted by the vehicle as detected by a sound detector stationary with the vehicle and/or moving with a known velocity relative to the vehicle. A comparison of the frequency of the sound emitted by the vehicle as detected by the sound detector stationary with the user with the reference frequency can thus indicate a velocity of the vehicle relative to the user. The method may further comprise determining, based on the comparing, a velocity of the vehicle relative to the user, wherein the relevance measure is determined depending on said velocity. In some implementations, said frequency of the sound is a first frequency, the method further comprising determining a second frequency of said sound different of the first frequency, wherein the relevance measure is determined depending on a difference between the first frequency and the second frequency. To illustrate, an amount of the frequency-shifting of the sound emitted by the vehicle as detected by the sound detector stationary with the user, which is caused by a movement of the vehicle relative to the user, can depend on the frequency of emitted by the vehicle. In particular, a frequency dispersion in the medium in which the sound waves propagate can cause such a difference in the frequency shift of the sound detected by the sound detector stationary with the user. The difference of the first frequency and the second frequency of the sound detected by the sound detector stationary with the user can thus also indicate a velocity of the vehicle relative to the user. The method may further comprise determining, based on said difference, a velocity of the vehicle relative to the user, wherein the relevance measure is determined depending on said velocity.

In some implementations, the user-related data is first user-related data and the relevance measure is a first relevance measure, wherein the method further comprises providing second user-related data after controlling the operation, the second user-related data indicative of a reaction of the user to the operation; and determining, based on the second user-related data, a second relevance measure indicative of a probability that the user is endangered by the vehicle. This may be employed to determine whether the user has become aware of the potential danger posed by vehicle after the operation has been controlled. In particular, the operation may be a first operation and a second operation may be controlled depending on the second relevance measure. The second operation may be selected to evoke a higher level of awareness of the user than the first operation. In particular, the second relevance measure may then be determined to be indicative of a higher probability that the user is endangered by the vehicle than the first relevance measure. In this way, a disturbance of the user by the alert may be minimized depending on the probability that the user is endangered by the vehicle.

FIG. 1 illustrates an exemplary traffic situation occurring on two parallel roads 11, 12 interconnected by a crossroad 13. The situation involves a pedestrian 21 and four vehicles 22, 23, 24, 25 driven by other road users. The vehicles comprise a van 22, a motorcycle 23, a car 24, and a bike 25. Car 24 is an emergency vehicle equipped with a siren and a flashing light, for instance a police car, an ambulance, a fire-fighting vehicle, or the like. Pedestrian 21 intends to walk over crossroad 13. At the same time, the driver of van 22 intends to take a turn to the right on first parallel road 11 to crossroad 13. Van 22 may thus pose a danger to pedestrian 21 depending on whether pedestrian 21 is unaware of van 22 and/or van 22 is unaware of pedestrian 21. Motorcycle 23 is also driven on first parallel road 11 in an opposed direction as compared to van 22, but its rider has no intention to turn to crossroad 13. Therefore, pedestrian 21 is not threatened by motorcycle 23. Similarly, bike 25 and car 24 moving on second parallel road 12 are not steered toward crossroad 13 and therefore do not pose a risk to pedestrian 21. However, car 24 following bike 25 at a higher speed may endanger the rider of bike 25 depending on whether car 24 notices bike 25 and/or the bike rider is able to anticipate car 24 approaching behind him, for instance by perceiving a sound emitted by car 24 such as an engine noise or a siren.

The above described movements of pedestrian 21 and vehicles 22-25 are indicated in FIG. 1 by a respective arrow 31, 32, 33, 34, 35 each illustrating a trajectory of the respective road user. Trajectories 31-35 may be defined by a position and/or a speed and/or a moving direction and/or an itinerary of road users 21-25. Any of these quantities may be employed to estimate a risk posed by one of the road users to another. In the context of this application, speed is a scalar quantity. A velocity, as used herein, is defined as a vector quantity including information about the moving direction and the speed.

Pedestrian 21 or any other road user driving vehicle 22-25 may by a user of a hearing device. The hearing device can be employed to alert the user about a vehicle in its vicinity. The user, however, may feel disturbed by such an alert, in particular when the user is already aware of the approaching vehicle. In a rather crowded traffic situation, the user may also be easily irritated by too many alerts and then may lose track about the vehicles having the highest danger potential. It would therefore be desirable to restrict the alert to those circumstances and/or to those vehicles for which it can be assumed that the hearing device user is not aware of a potential threat and/or which represent the highest danger potential for the user.

Devices, systems, and methods for providing an operation of a hearing device alerting the user about a vehicle in a vicinity of the user are described herein. The operation may be controlled depending on a relevance measure indicative of a probability that the user is endangered by the vehicle. The relevance measure may be determined based on user-related data including information about the user and/or an ambient environment of the user and/or a property of the hearing device; and on vehicle-related data associated with at least one vehicle in a vicinity of the user. These and other operations, which may be performed by a processing unit included in the hearing device and/or an electronic device configured to be operated stationary with the user remote from the ear at which the hearing device is worn, are described in more detail in the description that follows.

FIG. 2 illustrates an exemplary hearing device 100 configured to be worn at an ear of a user. Hearing device 100 may be implemented by any type of hearing device configured to enable or enhance hearing by a user wearing hearing device 100. For example, hearing device 100 may be implemented by a hearing aid configured to provide an audio content such as an amplified version of a detected ambient sound to a user, a sound processor included in a cochlear implant system configured to provide electrical stimulation representative of audio content to a user, a sound processor included in a bimodal hearing system configured to provide both amplification and electrical stimulation representative of audio content to a user, or any other suitable hearing prosthesis. As another example, hearing device 100 may be implemented by an earbud or an earphone or a hearable configured to reproduce an audio content communicated by a wire or wirelessly to hearing device 100 and/or to reproduce a detected ambient sound with or without altering the ambient sound and/or adding sound features to the ambient sound.

In the illustrated example, hearing device 100 includes a processor 102 communicatively coupled to a memory 103, an output transducer 107, a detector unit 110, and a communication unit 105. Hearing device 100 may include additional or alternative components as may serve a particular implementation.

Output transducer 107 may be implemented by any suitable audio transducer configured to output an audio signal to the user, for instance a receiver of a hearing aid, an output electrode of a cochlear implant system, or a loudspeaker of an earbud. The audio transducer may be implemented as an acoustic transducer configured to generate sound waves when outputting the audio signal. Processor 102 may be configured to obtain data indicative of a property of the audio signal outputted to the user. The property may comprise, for instance, information about the origin of the audio signal, for example information whether the audio signal is representative of a sound detected in the ambient environment and/or whether the audio signal is based on data communicated to hearing device 100 from an external data source, for instance via a radio frequency (RF) signal. RF, as used herein, may include any oscillation rate of an alternating electric current and/or voltage and/or of a magnetic and/or electric and/or electromagnetic field and/or mechanical system, for instance within a frequency range between 1 kHz and 1 THz, more particularly between 20 kHz and 300 GHz. The property may also comprise information about a quality of the outputted audio signal, for instance a volume and/or a sound processing parameter applied in a processing of the audio signal.

Detector unit 110 may include any suitable detector configured to provide data indicative of a property detected on the user and/or in an ambient environment of the user. Detector unit 110 may further include any suitable detector configured to provide data including information about a property of a vehicle.

Communication unit 105 may be implemented by any data receiver and/or data transmitter and/or data transducer configured to receive and/or transmit and/or exchange data with a remote data source via a communication link. The communication link may be established via a communication port 106 included in the communication unit 105, which may provide for wireless and/or wired communication with the external data source. For instance, data may be communicated in accordance with a Bluetooth™ protocol and/or by a mobile phone network such as 4G or 5G and/or by any other type of RF communication such as, for example, data communication via an internet connection and/or data communication at a frequency in a GHz range.

The remote data source may be any data source remote from hearing device 100, in particular any data source operative remote from the ear at which hearing device 100 is worn and/or any data source remote from the user's ears. In some instances, the data source can be included in an electronic device stationary with the user remote from hearing device 100. In particular, the device may be stationary with respect to movements of the user, for instance stationary with the user when the user is walking and/or stationary with a vehicle driven by the user. The remote device stationary with the user may be provided at the location of the user, for example a device worn by the user and/or a device included in a vehicle which can be driven by the user. In some instances, the remote data source can be a data source stationary with the earth such as, for instance, a cellular data network and/or a computer network and/or a central data server and/or an internet cloud storing data, and/or stationary relative to a global positioning system (GPS) comprising satellites orbiting the earth. In some instances, the remote data source can included in a device stationary with a vehicle moveable relative to the hearing device user, for instance a vehicle driven by another road user. Such a vehicle may be distant from the user and/or located in a vicinity of the user.

Memory 103 may be implemented by any suitable type of storage medium and is configured to maintain, e.g. store, data controlled by processor 102, in particular data generated, accessed, modified and/or otherwise used by processor 102. For example, processor 102 may control memory 103 to maintain a data record based on data provided by detector unit 110 and/or communication unit 105. Memory 103 may also be configured to store instructions for operating hearing device 100 that can be executed by processor 102, in particular an algorithm and/or a software that can be accessed and executed by processor 102.

Processor 102 is configured to access user-related data including information about the user and/or an ambient environment of the user and/or a property of the hearing device worn at the ear of the user. The user-related data may include information obtained at the ear when hearing device 100 is worn by the user. The user-related data may comprise data provided by detector unit 110 and/or data indicative of a property of the audio signal outputted by output transducer 107. Processor 102 may also be configured to access user-related data including other information than the information obtained at the ear when hearing device 100 is worn by the user. The other information may be received via communication unit 105.

Processor 102 is further configured to control an operation of hearing device 100 depending on a relevance measure indicative of a probability that the user is endangered by a vehicle, the operation alerting the user about the vehicle. A processing unit comprises processor 102. In some implementations, as further illustrated below, the processing unit may further comprise a processor included in an electronic device configured to be operated remote from the ear at which hearing device 100 is worn. Processing unit 102 is configured to determine the relevance measure based on the user-related data and on vehicle-related data associated with at least one vehicle in a vicinity of the user, the vehicle-related data including information about a property of the vehicle. The vehicle-related data may comprise data provided by detector unit 110 and/or data provided by communication unit 105.

Hearing device 100 may further include a user interface. The user interface may allow the user to adjust a property of an audio signal outputted by output transducer 107 and/or to modify an operational mode of hearing device 100 and/or to enter user-specific information. The user-specific information can be employed, for instance, to customize a condition depending on which the relevance measure is determined.

Hearing device 100 may be configured to provide the audio signal outputted by audio transducer 107 with a directivity. In particular, processor 102 may be configured to provide sound data received from multiple audio channels, for instance from a microphone array, with a directivity by performing an acoustic beamforming.

Hearing device 100 may further include a venting channel providing for a venting between an inner region of an ear canal of the ear at which hearing device 100 is worn and an ambient environment outside the ear canal. Ambient sound may thus enter the ear canal from the ambient environment into the ear canal through the venting channel which may be perceived by the user as a natural sound. The natural sound may be perceived by the user in addition to a sound produced by audio transducer 107. An amount of the natural sound entering the ear canal from the ambient environment can depend on an effective size of the venting channel.

Hearing device 100 may include an active vent. The active vent may comprise an acoustic valve allowing to adjust the effective size of the venting channel, and an actuator allowing to electronically actuate the adjustment of the effective size of the venting channel by the acoustic valve. The venting channel can thus be modified in between different effective sizes providing for a different acoustic impedance. The different acoustic impedance can provide for a different amount of natural sound entering the ear canal through the venting channel. An example of such an active vent is disclosed in European patent application No. EP19199184.3. In this way, an amount of the natural sound perceivable by the user exclusive of and/or in addition to the audio signal output by audio transducer 107 can be adjusted by the active vent. In particular, a sound emitted by a vehicle in a vicinity of the user, which may be contained in the natural sound, may be made perceivable to the user depending on the effective size of the venting channel.

Hearing device 100 may be configured to provide for an active noise cancelling (ANC). ANC may be provided by an audio signal output by audio transducer 107. To this end, audio transducer 107 may be connected to a microphone via a control circuit. The control circuit can be configured to control superimposing a sound detected by the microphone with a sound generated by audio transducer 107 by outputting the audio signal. The control circuit may comprise a feedback control circuit. The microphone may then be an ear-canal microphone provided inside an ear canal at which hearing device 100 is worn. The control circuit may comprise a feedforward control circuit. The microphone may then be configured to detect a sound in the ambient environment of the user wearing hearing device 100. An example of a hearing device configured to provide for ANC is disclosed in U.S. patent application Ser. No. 15/473,889.

Hearing device 100 may further include a vibrator configured to produce a vibration of the hearing device which can evoke a tactile perception by the user at the ear. The vibration may be produced, for instance, by generating periodic movements of a massive feature movably coupled with the hearing device. An example of such a vibrator is disclosed in European patent application No. EP19199184.3. The vibration may be employed, for instance, to provide a warning signal to the user in the form of a tactile sensation at the ear.

Different types of hearing device 100 can also be distinguished by the position at which they are worn at the ear. Some hearing devices, such as behind-the-ear (BTE) hearing aids and receiver-in-the-canal (RIC) hearing aids, typically comprise an earpiece configured to be at least partially inserted into an ear canal of the ear, and an additional housing configured to be worn at a wearing position outside the ear canal, in particular behind the ear of the user. Some other hearing devices, as for instance earbuds, earphones, hearables, in-the-ear (ITE) hearing aids, invisible-in-the-canal (IIC) hearing aids, and completely-in-the-canal (CIC) hearing aids, commonly comprise such an earpiece to be worn at least partially inside the ear canal without an additional housing for wearing at the different ear position. In some instances, hearing device 100 is a binaural hearing device configured to be worn at a second ear of the user in addition to the first ear of the user.

FIG. 3 illustrates an exemplary implementation of hearing device 100 as a RIC hearing aid 120, in accordance with some embodiments of the present disclosure. RIC hearing aid 120 comprises a BTE part 122 configured to be worn at an ear at a wearing position behind the ear, and an ITE part 121 configured to be worn at the ear at a wearing position at least partially inside an ear canal of the ear.

ITE part 121 is an earpiece comprising a housing 123 at least partially insertable in the ear canal. Housing 123 encloses output transducer 107 and a detector 118. Detector 118 is an ITE detector configured to provide user-related data including information obtained in the ear canal and/or at the concha of the ear when hearing device 120 is worn by the user. In some instances, ITE detector 118 comprises an ear-canal microphone configured to detect sound inside the ear canal. In some instances, ITE detector 118 comprises a physiological sensor configured to detect a physiological property of the user. In some instances, ITE detector 118 comprises a movement sensor configured to detect a movement of the user.

Housing 123 may further comprise a flexible member 124 adapted to contact an ear canal wall when housing 123 is at least partially inserted into the ear canal. An acoustical seal with the ear canal wall may thus be provided at the housing portion contacting the ear canal wall. The acoustic seal may at least partially block ambient sound from entering the ear canal. This can lead to an increased risk in a traffic situation, when the user is not able to notice a sound emitted from an approaching vehicle. The risk can be mitigated by outputting an audio signal representative of the ambient sound, which may be detected by a microphone, to the user via output transducer 107. Minimization of the risk may be further improved, even as compared to a traffic participant not wearing a hearing device, by modifying the detected ambient sound in the outputted audio signal in order to focus the user's attention to the approaching vehicle and/or by including a dedicated warning notification in the outputted audio signal.

Housing 123 is a first housing. BTE part 122 comprises a second housing 126 configured to be worn behind the ear. Second housing 126 accommodates processor 102 communicatively coupled to communication unit 105 and two detectors 112, 116. Detectors 112, 116 are BTE detectors configured to provide user-related data including information obtained behind the ear when hearing device 120 is worn by the user. First BTE detector 112 comprises a microphone configured to detect sound in an ambient environment of the user. In some instances, first BTE detector 112 comprises a microphone array comprising a plurality of spatially separated microphones for detecting the sound. In some instances, second BTE detector 116 comprises a physiological sensor configured to detect a physiological property of the user. In some instances, second BTE detector 116 comprises a movement sensor configured to detect a movement of the user. In some instances, second BTE detector 116 comprises an optical sensor configured to detect optical information in the ambient environment. For example, the optical sensor may comprise a camera configured to provide image information of the ambient environment. In some instances, second BTE detector 116 comprises a radar sensor configured to detect information about features in the ambient environment based on emitting and receiving radio waves. Detector unit 110 may thus be implemented by ITE detector 118 and/or first BTE detector 112 and/or second BTE detector 116.

BTE part 122 and ITE part 121 are interconnected by a cable 128. Processing unit 102 is communicatively coupled to output transducer 107 and BTE detector 118 via cable 128 and a cable connector 129 provided at second housing 122. Processor 102 can thus be configured to receive user-related data from ITE detector 118 and/or first BTE detector 112 and/or second BTE detector 116 and/or communication unit 105. The received data may also comprise vehicle-related data including information about a property of a vehicle. BTE part 122 may further include a battery 125 as a power source for the above described components.

FIG. 4 illustrates an exemplary hearing system 201 comprising hearing device 100 and an electronic device 200 configured to be operated remote from the ear at which hearing device 100 is worn. Remote device 200 can be configured to be operated stationary with respect to movements of the user, in particular translational movements and/or rotational movements of the user. For example, the remote device stationary with the user may be a device worn by the user, in particular on the user's body, and/or a device included in a vehicle which can be driven by the user. The remote device stationary with the user may be provided at the location of the user. Remote device 200 is communicatively coupled to hearing device 100. In the illustrated example, remote device 200 includes a processor 202 communicatively coupled to a memory 203, a detector unit 210, and a communication unit 205. Remote device 200 may include additional or alternative components as may serve a particular implementation. In some other implementations, remote device 200 may not include detector unit 210. In some other implementations, remote device 200 may not include processor 202 and/or memory 203.

Detector unit 210 may include any suitable detector configured to provide user-related data indicative of a property detected on the user and/or in an ambient environment of the user and/or vehicle-related data including information about a property of a vehicle.

Communication unit 205 is configured to receive data from and/or transmit data to and/or exchange data with communication unit 105 of hearing device 100. For this purpose, a communication link 212 may be established between a communication port 206 of communication unit 205 and communication port 106 of communication unit 105. Communication link 212 may be wired or wireless. For instance, data may be communicated in accordance with a Bluetooth™ protocol and/or by any other type of RF communication.

As illustrated, communication port 206 may be a first communication port and communication unit 205 may comprise a second communication port 207. Second communication port 207 is configured to receive data from a remote data source different from hearing device 100, in particular a data source external from hearing system 201, as exemplified hereafter. In some instances, data can be received via a communication network 214 from the external data source transmitting external data. The communication network 214 may comprise, for instance, a cellular data network and/or a computer network. For example, the cellular data network may be based on a global system for mobile communications (GSM) and/or a universal mobile telecommunications system (UMTS). The computer network may comprise, for instance, a local area network (LAN) and/or a personal area network (PAN) and/or a metropolitan area network (MAN) and/or a wide area network (WAN). The computer network may also comprise a wireless network such as WLAN and/or WPAN. In some instances, the external data can be received from a global positioning system (GPS) 215 in the form of GPS data. In some instances, the external data can be received from an external data source stationary with the earth such as a central server and/or a cloud 216 comprising a database 217 storing the external data. For example, the external data may be received from the external data source stationary with the earth via a computer network and/or a cellular data network. In some instances, the external data can be received from an external device 219 stationary with a vehicle 218 moveable relative to the user. External device 219 stationary with vehicle 218 may be provided at the location of vehicle 218, for example a device included in a vehicle moveable relative to the user, which may be distant from the user and/or located in a vicinity of the user. For instance, the external data may be received from external device 219 via a RF signal emitted from external device 219. External device 219 may be included in a vehicle moving independently from the user, in particular a vehicle of a traffic participant different from the user.

In some other implementations, communication unit 105 of hearing device 100 is provided with second communication port 207 in addition to first communication port 106. In some other implementations, communication unit 105 of hearing device 100 and communication unit 205 of remote device 200 each are provided with second communication port 207. In particular, communication unit 105 of hearing device 100 and communication unit 205 of remote device 200 may be configured to receive data from different external data sources, as exemplified above. In some implementations of hearing device 100, as illustrated in FIG. 1, communication port 106 of communication unit 105 is implemented as communication port 207.

A processing unit may comprise processor 102 of hearing device 100 and/or processor 202 of remote device 200. Processing unit 102, 202 is configured to access user-related data including information about the user and/or an ambient environment of the user and/or a property of the hearing device worn by the user, which may include information obtained by hearing device 100 at the ear when hearing device 100 is worn by the user. The user-related data may comprise data provided by detector unit 110 and/or data indicative of a property of the audio signal outputted by output transducer 107 and/or data provided by communication unit 105. Processing unit 102, 202 may be further configured to access user-related data including information obtained remote from the ear when hearing device 100 is worn by the user. The user-related data obtained remote from the ear may comprise data provided by detector unit 110 and/or data provided by communication unit 105. Processing unit 102, 202 is also configured to access vehicle-related data including information about a property of a vehicle. The vehicle-related data may comprise data provided by detector unit 110 and/or data provided by detector unit 210 and/or data provided by communication unit 105 and/or data provided by communication unit 205. Processing unit 102, 202 is further configured to determine a relevance measure indicative of a probability that the user is endangered by the vehicle based on the user-related data and on the vehicle-related data. Processing unit 102, 202 is also configured to control an operation of hearing device 100 depending on the relevance measure.

In some implementations, each of those operations can be performed independently by at least one of processor 102 and processor 202 of the processing unit. In some implementations, those operations can be shared between processors 102 and processor 202. For instance, at least one of the operations may be performed by one of processors 102, 202, and the remaining operations may be performed by the other of processors 102, 202. In some implementations, at least one those operations can be performed jointly by processor 102 and processor 202, for instance by performing different tasks of the operation. Processing unit 102, 202 may be implemented, for instance, as a distributed processing system of processors 102, 202 and/or in a master/slave configuration of processors 102, 202. In some other implementations, the processing unit configured to perform those operations consists of processor 102 included in hearing device 100 or processor 202 included in remote device 200.

In some implementations, as illustrated, remote device 200 comprises a memory 203 which may be implemented by any suitable type of storage medium. A memory unit may comprise memory 103 and/or memory 203. Processing unit 102, 202 may control memory unit 103, 203 to maintain a data record based on data provided by detector unit 110 and/or detector unit 210 and/or communication unit 105 and/or communication unit 205. Memory unit 103, 203 may also be configured to store instructions for operating hearing system 201 that can be executed by processing unit 102, 202, in particular an algorithm and/or a software that can be accessed and executed by processing unit 102, 202.

In some implementations, remote device 200 further comprises a user interface. The user interface may allow the user to adjust a property of an audio signal outputted by output transducer 107 of hearing device 100 and/or to modify an operational mode of hearing device 100 and/or remote device 200 and/or to enter user-specific information. The user-specific information can be employed, for instance, to customize a condition depending on which the relevance measure is determined.

FIG. 5 illustrates exemplary implementations of electronic device 200 stationary with the user and operable at a position remote from the ear at which hearing device 100 is worn as a wearable device 220, in accordance with some embodiments of the present disclosure. Wearable device 220 comprises a housing 226 configured to be worn by the user on the user's body at a position remote from the ear at which hearing device 100 is worn. In the illustrated example, wearable device 220 is implemented as a communication device, for example a smartphone, a tablet, a smartwatch, and/or the like. Wearable device 220 further comprises a screen 224 configured to display information to the user and/or as a touchscreen operable as a user interface. Various sensor types, such as a camera, a microphone, a magnetometer, a movement sensor, a physiological sensor, etc., may be implemented in a detector unit of wearable device 220. Further conceivable are other implementations of wearable device 220 such as, for instance, smart glasses. When the user is driving a vehicle, wearable device 220 can also be stationary with the vehicle. Wearable device 220 may then also be operated remote from the user's body. For instance, the user may mount wearable device 220 on a steering rod of a bike and/or put wearable device 220 in a glove compartment or a passenger seat of a car.

FIG. 6 illustrates exemplary implementations of electronic device 200 stationary with the user and operable at a position remote from the ear at which hearing device 100 is worn as a vehicle-included device 230. Vehicle-included device 230 is implemented in a vehicle that can be driven by the user. In the illustrated example, vehicle-included device 230 is mounted on a frame or a mudguard of a bike 233. Vehicle-included device 230 may also be mounted, on a chassis of a car or a motorbike, for instance on a rooftop of a car. As illustrated, vehicle-included device 230 may be disposed at a rear end of vehicle 230 which can be advantageous to provide vehicle-related information from a direction different from a viewing direction of the user. In other implementations, vehicle-included device 230 may be provided in proximity to the user which can be advantageous to provide user-related information and/or to provide a user interface allowing the user to interact with vehicle-included device 230. For instance, vehicle-included device 230 may be implemented as a board computer and/or a navigation system included in a vehicle such as a car.

Vehicle-included device 230 may comprise detector unit 210. Detector unit 210 may comprise a sensor configured to detect a property of another vehicle in a vicinity of vehicle 233 when driven by the user. For instance, the sensor may be configured to detect a property of the other vehicle when approaching vehicle 233 from behind. To this end, detector unit 210 may comprise a sound sensor and/or an optical sensor and/or a radar sensor and/or an ultrasonic sensor and/or a geomagnetic sensor, as further described below. Vehicle-included device 230 may further comprise processor 202 to process the information detected by detector unit 210. The information detected by detector unit 210 may also be transmitted to hearing device 100 by communication unit 205 of vehicle-included device 230 in order to be processed by processor 102 of hearing device 100.

In some implementations, the hearing system comprises hearing device 100 and a plurality of electronic devices 200 operable remote from the ear stationary with the user. For instance, the hearing system may comprise wearable device 220 and vehicle-included device 230. In particular, wearable device 220 may be a communication device communicatively coupled with hearing device 100 and vehicle-included device 230.

FIG. 7 illustrates an exemplary detector unit 410 comprising a sound sensor 411 and/or a radio sensor 412 and/or an optical sensor 413 and/or a movement sensor 414 and/or a physiological sensor 415 and/or an environment sensor 416. Detector unit 110 of hearing device 100 and/or detector unit 210 of remote device 200 may be implemented as detector unit 410. In some instances, detector unit 110 may comprise at least one of sensors 411-416 and detector unit 210 may comprise at least another one of sensors 411-416 in order to provide different user-related data and/or vehicle-related data which may be employed as complementary information for determining the relevance measure. In some instances, detector unit 110 may comprise at least one of sensors 411-416 and detector unit 210 may comprise the same type of sensors 411-416. This can be useful to provide different user-related data and/or vehicle-related data as complementary information and/or to provide equivalent user-related data and/or vehicle-related data as redundant information for determining the relevance measure with a higher reliability.

Sound sensor 411 can be implemented as any device configured to detect a sound in an ambient environment of the user and/or inside the ear-canal and to provide sound data representative of the detected sound, in particular a microphone and/or a microphone array and/or a VAD and/or a speaker recognition detector and/or a speech type detector and/or a body sound detector. In some implementations, sound sensor 411 can be configured to detect a sound emitted from a vehicle in a vicinity of the user which may be employed as vehicle-related data including information about a property of the vehicle. The vehicle-related data may include information about a dynamic property and/or an intrinsic property of the vehicle. In some instances, an increasing level of the detected sound and/or a sound level exceeding a threshold may be employed to indicate a proximity of the vehicle relative to the user. In some instances, sound data representative of the detected sound may be compared with a sound feature representative of a sound typically emitted by a vehicle. This may be employed to indicate a presence and/or a type of a vehicle in a vicinity of the user. To illustrate, the sound data representative of the detected sound may be compared with a sound feature typical for a siren of an emergency vehicle and/or a sound feature typical for an electric vehicle (EV) or hybrid vehicle (HV).

In some instances, a frequency characteristics of the detected sound may be employed to indicate a property of the vehicle in the vicinity of the user. Employing the frequency characteristics of the detected sound may be particularly advantageous for vehicles that can be hardly noticed by the user by their natural sound properties such as EVs or HVs. To illustrate, a motor of EVs and HVs can be running relatively quiet making it difficult for other traffic participants to recognize those vehicles based on the emitted sound. This increases the potential hazard of those vehicles for other road users, in particular during poor visibility conditions and/or when the other road users are approached from behind by such a vehicle. Often, however, a sound emitted by those vehicles comprises a typical frequency characteristics. For instance, current motors of EVs and HVs generate a switching noise at higher frequencies, such as in a frequency range between 5 and 30 kHz, which is caused by the internal electrical propulsion system. In particular, the speed of an interior permanent magnet (IPM) synchronous motor included in those vehicles is usually controlled by changing a frequency of an input alternating current (AC), for instance by a pulse-width modulation (PWM), which in turn can generate a sound released into the air outside the vehicle at the respective frequency. As a result, determining the frequency characteristics of the detected sound can not only provide information about a presence and/or proximity and/or distance and/or type of such a vehicle in a vicinity of the user but also other vehicle-related information such as the vehicle speed. In practice, the frequency characteristics may be identified in the detected sound by a machine learning (ML) algorithm that has been trained based on sound data including the respective frequency characteristics labelled with the corresponding vehicle type.

The frequency characteristics may also be employed to determine a Doppler shift in the detected sound which can indicate a moving direction and/or speed and/or itinerary of a vehicle in a vicinity of the user. To illustrate, a sound emitted by a vehicle, as perceived by a person stationary with the vehicle, can be frequency-shifted relative to the corresponding sound detected by sound sensor 411 stationary with the user depending on a velocity of the vehicle emitting the sound relative to the user. Thus, the frequency of the sound emitted by the vehicle as detected by sound sensor 411 stationary with the user can indicate a property of the vehicle relative to the user, in particular the moving direction and/or speed and/or itinerary of a vehicle in the vicinity of the user. For instance, the sound detected by sound sensor 411 stationary with the user can be compared to a reference frequency corresponding to a frequency of the sound emitted by the vehicle as detected by a sound detector stationary with the vehicle and/or moving with a known velocity relative to the vehicle. As another example, a difference of a first frequency and a second frequency of the sound detected by sound sensor 411 stationary with the user can be determined, wherein the difference can be indicative of the property of the vehicle, for instance the moving direction and/or speed and/or itinerary of the vehicle in the vicinity of the user.

In some instances, a spatial characteristics of the detected sound may be employed to indicate a property of a vehicle in a vicinity of the user. To this end, the sound detector may comprise a plurality of spatially distributed microphones allowing to spatially resolve the detected sound. The microphones may be implemented in a single ear unit of a hearing device worn at one ear and/or in two ear units of a binaural hearing device worn at both ears and/or in an electronic device remote from the ear at which the hearing device is worn. The multiple microphones can each provide sound data representative of a sound emitted from a vehicle in the vicinity of the user. Differences in the sound data provided by the different microphones can then be evaluated. The differences may comprise a different time of arrival and/or a different sound level and/or a different phase and/or a different frequency and/or a different signal propagation delay of the detected sound associated with the vehicle in the vicinity of the user. In a binaural hearing device, the microphones of sound sensor 411 may be distributed in two ear units worn at different ears of the user. The differences in the sound data provided by the microphones may then comprise an interaural phase difference (IPD) and/or an interaural time difference (ITD) and/or an interaural level difference (ILD). Determining those differences can be exploited, for instance, to gain information about a presence and/or type and/or proximity and/or distance and/or location and/or speed and/or moving direction and/or itinerary of the vehicle. In some instances, a triangulation and/or a Doppler analysis of the sound data from the different positions may be employed.

In some instances, a sound sensor may be implemented stationary with the vehicle in a vicinity of the user, wherein the sound sensor is configured to provide sound data representative of a sound emitted from the vehicle. The sound data may be transmitted from the vehicle in the vicinity of the user to hearing device 100 and/or remote device 200, in particular to communication unit 105, 205, for instance as an RF signal. The transmitted sound data may then be compared to the sound data provided by sound sensor 411. Differences between the sound data provided by the sound sensor stationary with the vehicle and the sound data provided by sound sensor 411 stationary with the user can then be evaluated. Determining those differences can be also be exploited, for instance, to gain information about a presence and/or type and/or proximity and/or distance and/or location and/or speed and/or moving direction and/or itinerary of the vehicle.

In some implementations, sound sensor 411 can be configured to detect a sound emitted from the user and/or a sound emitted in the ambient environment of the user which may be employed as user-related data indicative of a property detected on the user and/or in an ambient environment of the user. The user-related data may include information about a dynamic and/or intrinsic property of the user and/or the ambient environment of the user. The user-related data indicative of a property detected on the user may include sound data representative of a voice activity of the user, in particular a speech of the user, and/or chewing sounds and/or swallowing sounds of the user. This may indicate the user being involved in a conversation and/or the user eating. In a traffic situation, those activities can distract the user from noticing potentially dangerous vehicles and thus may increase the risk of the user. The user-related data indicative of a property detected on the user may also include sound data representative of a breathing sound of the user. An increased breathing rate, in particular hyperventilation, may indicate an increased level of fatigue of the user and therefore an increased risk in traffic. The relevance measure may thus be determined to be indicative of an increased probability that the user is endangered by an vehicle in its vicinity.

The user-related data indicative of a property detected in the ambient environment of the user may include, for instance, sound data representative of a noise level prevailing in the ambient environment. Exposure to noise can make it more difficult to hear approaching vehicles enhancing the traffic risk for the user. The user-related data indicative of a property detected in the ambient environment may also include sound data representative of a current weather, such as wind noise and/or splashing rain drops, which can impact the risk of the user on the road. The user-related data indicative of a property detected in the ambient environment may also include sound data representative of a current traffic situation, such as a highly busy traffic or rather low traffic, which can impact the risk of the user on the road.

In some implementations, the sound sensor 411 may be configured to detect ultrasonic sound. Sound sensor 411 may further comprise an ultrasonic transmitter configured to emit ultrasonic waves and to detect a portion of the emitted waves after they have been reflected by a feature. The data provided by the ultrasonic sensor may comprise vehicle-related data, for instance data containing information about a presence and/or type and/or location and/or speed and/or moving direction and/or itinerary and/or distance and/or proximity of a vehicle relative to the user. The data provided by the ultrasonic sensor may also comprise user-related data, for instance information about a visibility range of the user and/or obstacles in the ambient environment of the user.

In some implementations, the sound detected by sound sensor 411 may be employed as vehicle-related data including information about a property of the vehicle and as user-related data indicative of a property detected on the user and/or in an ambient environment of the user. To this end, a sound classifier may be employed which may be configured to classify the sound data provided by sound sensor 411 as vehicle-related data or as user-related data. An ML algorithm may employed by the processing unit configured to perform the classification. It may also be that the ML algorithm is configured to separate and/or extract different sound features from the sound data provided by sound sensor 411, wherein each of the sound features may be associated with vehicle-related data and/or user-related data. To illustrate, the sound detected by sound sensor 411 may contain a sound feature associated with a motor of an approaching car, and a sound feature associated with a voice activity of the user, and a sound feature associated with background noise.

Radio sensor 412 may be implemented as any device configured to detect radio waves. In some implementations, radio sensor 412 can be implemented with communication unit 105, 205 of hearing device 100 and/or remote device 200. For instance, communication port 106, 206, 207 can be implemented as an antenna detecting the radio waves. In some instances, a RF emitter may be provided stationary with the vehicle in a vicinity of the user, the RF emitter configured to emit an RF signal. Radio sensor 412 may comprise a plurality of spatially separated RF receiving ports each configured to receive the RF signal at different locations. Differences in the RF signals detected by the different RF receiving ports can then be evaluated. The differences may comprise a different time of arrival and/or a different intensity of the received RF signals. This can also be exploited to gain information about a presence and/or type and/or location and/or speed and/or moving direction and/or itinerary and/or distance and/or proximity of the vehicle. In particular, an analysis of the received signal strength indication difference (RSSID) may be employed.

In some instances, radio sensor 412 comprises a radar sensor configured to emit electromagnetic waves and to detect a portion of the emitted waves after they have been reflected by a feature. For instance, the radar sensor may be implemented in vehicle-included device 230, as illustrated in FIG. 6. Radar data provided by the radar sensor may comprise vehicle-related data, for instance data containing information about a presence and/or type and/or location and/or speed and/or moving direction and/or itinerary and/or distance and/or proximity of a vehicle relative to the user. The radar data provided by the radar sensor may also comprise user-related data, for instance information about a visibility range of the user and/or obstacles in the ambient environment of the user.

Optical sensor 413 may be implemented as any device configured to detect light waves. In some instances, optical sensor 413 comprises a camera configured to provide image data representative of the detected light. The image data may comprise vehicle-related data. For instance, the image data can be indicative of a presence and/or type and/or location and/or speed and/or moving direction and/or itinerary and/or distance and/or proximity of a vehicle in a vicinity of the user. The image data provided by the camera may also comprise user-related data. For instance, the image data can be indicative of a visibility range and/or a weather and/or light conditions of the ambient environment of the user. These parameters can influence the risk for the user in a traffic situation. In some instances, optical sensor 413 comprises a camera. In some instances, optical sensor 413 comprises a light emitter and a light receiver. Optical sensor 413 can thus be configured to emit electromagnetic waves and to detect a portion of the emitted waves after they have been reflected by a feature. Optical sensor 413 may thus be applied corresponding to the radar sensor described above.

Movement sensor 414 may be implemented by any suitable device configured to provide movement data indicative of a movement of the user and/or a vehicle stationary with the user. The movement data may comprise acceleration data indicative of an acceleration and/or velocity data indicative of a velocity and/or displacement data indicative of a displacement and/or rotation data indicative of a rotation. Movement sensor 414 may also be implemented as an orientation sensor configured to provide orientation data indicative of an orientation of the user and/or a vehicle stationary with the user relative to a reference frame. For instance, the reference frame may be a direction of the gravitational force and/or a direction of the earth's magnetic field. In this way, orientational displacements of the user and/or a vehicle stationary with the user may be determined. Movement sensor 414 may also be implemented as a location sensor configured to provide location data indicative of a location of the user and/or a vehicle stationary with the user relative to a reference frame. For instance, the reference frame may be stationary with the earth. In this way, translational and/or orientational displacements of the user and/or a vehicle stationary with the user may be determined.

In particular, movement sensor 414 may comprise at least one inertial sensor. The inertial sensor can include, for instance, an accelerometer configured to provide the movement data representative of an acceleration and/or displacement and/or rotation, and/or a gyroscope configured to provide the movement data representative of a rotation. An accelerometer can further be configured to provide orientation data indicative of an orientation relative to the gravitational force. Movement sensor 414 may can also include a magnetometer, in particular an electronic compass, configured to measure the direction of an ambient magnetic field. Movement sensor 414 may also comprise a navigation sensor such as a GPS sensor. Movement sensor 414 can be mechanically coupled to a housing of hearing device 100 such that it remains in a fixed position relative to the housing upon a translational and/or rotational displacement of the housing. Movement sensor 414 can also be mechanically coupled to a housing of remote device 200.

Movement sensor 414 can thus be employed to provide user-related data indicative of a property detected on the user and/or in an ambient environment of the user. The user-related data may comprise, for instance, rotation data indicative of a rotation of the user. The rotation data may comprise head rotation data indicative of a head rotation of the user. Movement sensor 414 may be included in hearing device 100 wearable at the ear in order to provide the head rotation data. The rotation data may also comprise body rotation data indicative of a body rotation of the user. Movement sensor 414 may be included in remote device 200 wearable at the user's body in order to provide the body rotation data. Movement sensor 414 may also be included in hearing device 100 and in remote device 200 in order to determine a head rotation of the user relative to the user's body. In some instances, the rotation of the user may be evaluated relative to a location of a vehicle in a vicinity of the user and/or a moving direction of the vehicle and/or an itinerary of the vehicle and/or a predicted impact location of the user with the vehicle. A rotation of the user toward the vehicle can indicate the user's awareness about the vehicle. A risk for the user posed by the vehicle can thus be assumed to be reduced.

The user-related data may also comprise orientation data indicative of an orientation of the user. The orientation data may comprise head rotation data indicative of an orientation of the user's head and/or body orientation data indicative of an orientation of the user's body. In some instances, the orientation of the user may be evaluated relative to a location of a vehicle in a vicinity of the user and/or a moving direction of the vehicle and/or an itinerary of the vehicle and/or a predicted impact location of the user with the vehicle. An orientation of the user toward the vehicle can indicate the user's awareness about the vehicle. A risk for the user posed by the vehicle can thus be assumed to be reduced. In some instances, the orientation of the user's head may be evaluated relative to the earth's surface. For instance, an accelerometer may be employed to determine the orientation of the user's head relative to the gravitational force. An increased risk for the user in a traffic situation may be determined when the orientation of the user's head deviates from a direction parallel to the surface of the earth by more than a predefined angle. For instance, the user may look on a handheld device during walking and/or may be fallen asleep during driving when his head points toward the surface of the earth. Therefore, it can be assumed that the user is not fully aware of potentially dangerous vehicles in his vicinity.

The user-related data may also comprise movement data indicative of a translational movement of the user and/or walking data indicative of a walking activity of the user and/or cycling data indicative of a cycling activity of the user and/or skating data indicative of a skating activity of the user and/or scooter data indicative of an activity of the user riding a scooter. In particular, a recurring pattern in the movement data typical for the walking activity and/or cycling activity and/or skating activity and/or scooter riding activity may be identified in the movement data. This can be exploited to determine whether the user is involved in such an activity or not, which may increase the traffic risk for the user. In some instances, at least one of those activities may be estimated to be more dangerous than another one such that the risk can be determined depending on the activity. In some instances, a pattern of the walking activity and/or cycling activity and/or skating activity and/or activity of riding a scooter may be determined and the risk is estimated to be reduced when the pattern changes. In particular, it can be assumed that the user will change the pattern of his activity when he notices a potentially dangerous vehicle in order to avoid the risk of colliding with the vehicle. The relevance measure may thus be determined depending on user-related data indicative of a movement of the user and/or a vehicle stationary with the user.

Movement sensor 414 may also be employed to provide vehicle-related data including information about a property of a vehicle in a vicinity of the user. For instance, movement sensor 414 may comprise a magnetometer which may determine a change of an ambient magnetic field when a vehicle, in particular a car, approaches the user. This may be exploited to gain information about a presence and/or type and/or location and/or speed and/or moving direction and/or itinerary of the vehicle.

Physiological sensor 415 may be implemented by any suitable device configured to provide physiological data indicative of a physiological property of the user. The physiological property can include, for instance, a heart rate, resting heart rate (RHR), heart rate recovery time, heart rate variation and/or arrhythmia, blood pressure, elevated blood pressure (hypertension), saturation pressure of blood oxygen (SpO2), maximum oxygen consumption (VO$_2$ max), blood glucose level, blood alcohol level, blood composition, cardiovascular health, endurance level, aerobic fitness level, biorhythm, body temperature, sweat rate, respiratory rate, cognitive load, listening intention, listening effort, cognitive decline, breakdown of neural activity over time, sleeping or waking state, distraction level, concentration level, relaxation level, physical exhaustion level, physiological stress, and/or the like. Any of those properties may be indicative of a level of fatigue of the user and/or a health condition of the user.

In some implementations, physiological sensor 415 comprises a biometric sensor. A biometric sensor, as used herein, may be any device configured to measure a biological characteristic intrinsic to a living organism, in particular a human body and to provide biometric data indicative of the biological characteristic. For instance, the biological characteristic may be a measured blood or molecular characteristic, in particular a varying light absorption and/or reflection, and/or an amount and/or density of a molecular content in biological tissue, and/or a measured electromagnetic signal generated by the living organism and/or a measured temperature characteristic for thermal energy produced by the living organism. In some examples, the biometric sensor comprises a photoplethysmography (PPG) sensor and/or an electrocardiography (ECG) sensor and/or an electroencephalography (EEG) sensor and/or an electrooculography (EOG) sensor and/or a temperature sensor and/or a skin conductance sensor and/or a RF sensor and/or a pupillometry sensor. The biometric sensor may be included in hearing device 100 and/or remote device 200. Implementing the biometric sensor in hearing device 100 can offer the advantage of a higher accuracy and/or reproducibility of the biometric data due to a particularly suitable measurement position for the biological characteristic at the user's ear.

The biometric sensor may be configured to provide an acute measurement of the biological characteristic, for instance by directly detecting energy and/or matter from the living organism, and/or a processed collection of acute measurements of the biological characteristic, for example by recording the biological characteristic over time such as in a PPG waveform and/or a recorded EEG signal. Biometric data may be any data provided by the biometric sensor representative for the measured biological characteristic. A physiological property of the user may be determined based on the biometric data. For instance, a heart rate and/or blood pressure and/or heart rate variability (HRV) and/or $VO_2$ max and/or aerobic fitness level and/or blood content and/or level of fatigue may be determined based on biometric data provided by a PPG sensor and/or an ECG sensor. A cognitive load and/or listening effort and/or concentration level and/or biorhythm and/or physiological stress and/or distraction level and/or level of fatigue may be determined based on biometric data provided by an EEG sensor and/or a pupillometry sensor. An eye gaze movement may be determined based on biometric data provided by an EOG sensor.

In some implementations, the physiological property may be determined by an assessment of data provided by a sensor or detector other than a biometric sensor. For instance, the physiological property may be determined based on movement data of movement sensor 414 which can indicate a level of fatigue such as a physical exhaustion level and/or relaxation level of the user. To illustrate, an evaluation of the movement data yielding that little or no movements have been performed by the user for a prolonged time can indicate a small physical exhaustion level of the user and/or a high relaxation level of the user. As another example, the physiological property may be determined based on sound data of sound sensor 411 which may also serve as a physiological indicator, e.g. for a level of fatigue and/or a distraction level of the user. To illustrate, an evaluation of the sound data revealing silence to a certain degree for a while in the ambient environment of the user can indicate a high relaxation level indicating small level of fatigue of the user and/or can indicate a small distraction level of the user. The sound may comprise a microphone, in particular a microphone array, and/or a VAD and/or a speaker recognition detector and/or a speech type detector and/or a body sound detector. The body sound detector may be sensitive for body sounds, which may include at least one of gulping, eating, burping, and digestion sounds. An evaluation of the sound data revealing a speech near the user and/or an eating activity of the user can indicate a high distraction level and/or a high level of fatigue of the user.

Physiological sensor 415 can thus be employed to provide user-related data indicative of a property detected on the user. In some instances, the user-related data can comprise physiological data indicative of a level of awareness of the user about a vehicle in his vicinity. For instance, a rather high distraction level and/or a rather high level of fatigue can indicate a rather low awareness of the user about the potential danger coming from a vehicle in his vicinity. A rather high heart rate, which may be determined based on biometric data provided by a PPG sensor and/or an EEG sensor, can be an indication of a physical exhaustion which can also limit the user's awareness. A rather high blood pressure and/or body temperature can indicate a level of fatigue and/or health condition of the user affecting his awareness about the traffic situation. A certain blood content, for instance a blood alcohol level, can also be indicative of a decreased awareness level. On the other hand, a small distraction level and/or a small level of fatigue of the user can be an indication of a high awareness about the current traffic situation. A current phase of the user's biorhythm can further indicate the user's awareness. In some instances, a correlation between the user-related data and the vehicle-related data may be employed to determine a level of the user's awareness about the vehicle in his vicinity. For instance, a change in brain wave data provided by an EEG sensor may be employed as an indication of the user's awareness when the change is temporally correlated with a vehicle appearing in the vicinity of the user. The relevance measure may thus be determined depending on user-related data indicating the user's awareness based on a physiological property.

Environment sensor 416 may be implemented by any suitable device configured to provide environmental data indicative of a property of an ambient environment of the user. For instance, the environmental data detected in the ambient environment can be indicative of a sound in the environment, such as a sound level and/or voices of people surrounding the user and/or traffic noise, ambient temperature, humidity, barometric pressure, altitude, weather, climate, solar energy, wind, smog, rain, hail, snow, ice, daylight, darkness, visibility conditions, airborne particle density, pollution, traffic, exhaust from vehicle engines, and/or the like. Environment sensor 416 may comprise sound sensor 411 and/or radio sensor 412 and/or optical sensor 413 and/or a temperature sensor and/or a barometric sensor and/or a humidity sensor and/or a particle sensor and/or a proximity sensor. For instance, a current weather may be determined based on data provided by sound sensor 411 and/or optical sensor 413 and/or the temperature sensor and/or the barometric sensor and/or the humidity sensor. A situation in which the user is involved in a conversation and/or surrounded by other people may be determined based on data provided by sound sensor 411 and/or optical sensor 413. A current level of traffic may be determined based on data provided by sound sensor 411 and/or optical sensor 413 and/or the particle sensor and/or the proximity sensor. Momentary visibility conditions may be determined based on data provided by optical sensor 413 and/or radio sensor 412 and/or sound sensor 411.

Environment sensor 416 can thus be employed to provide user-related data indicative of a property detected in an ambient environment of the user. In some instances, the user-related data can comprise environmental data indicative of risk factors in a traffic situation. The risk factors can comprise current weather conditions and/or current visibility conditions and/or a current traffic level. The risk factors can also comprise distracting and/or disturbing sounds such as people talking to the user and/or a high level of background noise. The relevance measure may thus be determined depending on user-related data indicating such a risk factor in the ambient environment.

FIG. 8 illustrates a functional block diagram of an exemplary sensor data processing algorithm that may be executed by a processing unit 420. Processing unit 420 may comprise processor 102 of hearing device 100 and/or processor 202 of remote device 200. As shown, the algorithm is configured to be applied to user-related data 421 including information about the user and/or an ambient environment of the user and/or a property of the hearing device worn by the user, in particular information obtained at the ear when hearing device 100 is worn by the user, and vehicle-related data 422 associated with at least one vehicle in a vicinity of the user. Vehicle-related data 422 includes information about a property of the vehicle which may comprise information about a dynamic and/or intrinsic property of the vehicle. User-related data 421 includes information about a property of the user and/or an ambient environment of the user. User-related data 421 may comprise data indicative of a property detected by detector unit 110 on the user and/or in an ambient environment of the user and/or data received by communication unit 105, 205. Alternatively or additionally, user-related data 421 may comprise data indicative of a property of the hearing device 100 and/or remote device 200 operated by the user, for instance data indicative of a property of an audio signal outputted to the user by output transducer 107 and/or a current setting of hearing device 100 and/or remote device 200 and/or a property of detector unit 410. User-related data 421 and vehicle-related data 422 is inputted to processing unit 420. The algorithm comprises a relevance measure determining module 425, and an operation control module 427. Relevance measure determining module 425 can determine a relevance measure indicative of a probability that the user is endangered by the vehicle. Operation control module 427 can control an operation of hearing device 100 depending on the relevance measure, the operation alerting the user about the vehicle. In particular, operation control module 427 may be configured to control the operation when the relevance measure is determined to exceed a threshold of the probability that the user is endangered by the vehicle.

FIG. 9 illustrates different categories of user-related data 421 and vehicle-related data 422. In particular, user-related data 421 may comprise user-related data 431 and may further comprise any of user-related data 433, 441, 451. Vehicle-related data 422 may comprise any of vehicle-related data 432, 434, 442, 452. A first data category 430 comprises data obtained stationary with the user. User-stationary data 430 comprises user-related data 431 obtained by hearing device 100 when worn at the ear of the user. User-related data 431 may comprise data indicative of a property detected on the user and/or in an ambient environment of the user and/or data indicative of a property of an audio signal outputted to the user by output transducer 107. User-stationary data 430 may further comprise vehicle-related data 432 obtained by hearing device 100 when worn at the ear of the user. Vehicle-related data 432 may be obtained by detector unit 110 of hearing device 100. User-stationary data 430 may further comprise user-related data 433 obtained by electronic device 200 remote from the ear of the user and/or vehicle-related data 434 obtained by electronic device 200 remote from the ear of the user. User-related data 433 and/or vehicle-related data 434 may be obtained by detector unit 210 of remote device 200. User-related data 431, 433 and/or vehicle-related data 432, 434 may be communicated between hearing device 100 and remote device 200 via communication units 105, 205.

A second data category 440 comprises data obtained stationary with a vehicle in a vicinity of the user. Vehicle-stationary data 440 can comprise user-related data 441 and/or vehicle-related data 442 obtained stationary with the vehicle moving relative to the user in the user's vicinity. The vehicle may comprise a detector unit configured to obtain user-related data 441 and/or vehicle-related data 442. For instance, the vehicle may include a sound sensor configured to detect a sound emitted by the vehicle, wherein an audio signal representative of the detected sound may be employed as vehicle-related data 442. Vehicle-stationary data 440 may be transmitted to hearing device 100 and/or to remote device 100 stationary with the user. For instance, vehicle 218 may broadcast an RF signal including the vehicle-stationary data 440 in its vicinity and/or transmit vehicle-stationary data 440 to hearing device 100 and/or remote device 200 via a monodirectional or bi-directional communication link. Vehicle-stationary data 440 may be received by communication unit 105, 205 of hearing device 100 and/or remote device 100. A third data category 450 comprises user-related data 451 and/or vehicle-related data 452 obtained external from the user and/or a vehicle stationary with the user and/or a vehicle in a vicinity of the user. For instance, external data 450 may be obtained by a detector unit stationary with the earth. External data 450 may be broadcast and/or transmitted to hearing device 100 and/or remote device 200 via a monodirectional or bi-directional communication link.

User-related data 421, 431, 433, 441, 451, as used herein, may be any data indicative of a property associated with the user and/or an ambient environment of the user that is potentially suitable to have an impact on the user being endangered by a vehicle in the vicinity of the user. Vehicle-related data 422, 432, 434, 442, 452, as used herein, may be any data indicative of a property associated with a vehicle in a vicinity of the user that is potentially suitable to have an impact on the user being endangered by the vehicle.

In some instances, data provided by detector unit 110 of hearing device 100 and/or detector unit 210 of remote device 200 can be indicative of both a property associated with the user and/or an ambient environment of the user and a property associated with a vehicle in a vicinity of the user having an impact on the user being endangered by the vehicle. For example, a sound emitted by a vehicle in the vicinity of the user detected by sound sensor 411 may, on the one hand, indicate a property associated with the ambient environment of the user impacting the danger for the user. To illustrate, a rather loud sound emitted by the vehicle may reduce the risk for the user since the user may be prone to be alerted by the emitted sound. On the other hand, the sound emitted by the vehicle in the vicinity of the user may also indicate a property associated with the vehicle impacting the danger for the user. For instance, the sound emitted by the vehicle may indicate a type and/or location and/or moving direction and/or speed and/or distance and/or itinerary of the vehicle relative to the user. The data provided by detector unit 110 of hearing device 100 and/or detector unit 210 of remote device 200 may thus be employed as user-related data 421 and/or vehicle-related data 422. In particular, the relevance measure may then be determined based on the same data employed as user-related data 421 and vehicle-related data 422.

In some instances, the relevance measure is determined based user-related data 421 and vehicle-related data 422 differing from one another. For example, user-related data 421 may comprise data indicative of a movement of the user, which may be provided by movement sensor 414, and/or a physiological property of the user, which may be provided by physiological sensor 415, and/or a property of the ambient environment of the user, which may be provided by environment sensor 416, and vehicle-related data 422 may comprise data indicate of a type and/or location and/or moving direction and/or speed and/or distance and/or itinerary of the vehicle relative to the user, which may be provided by sound sensor 411 and/or radio sensor 412 and/or optical sensor 413. As another example, user-related data 421 may comprise data indicative of a property of an audio signal outputted to the user by an audio transducer included in the hearing device, and vehicle-related data 422 may comprise data indicate of a type and/or location and/or moving direction and/or speed and/or distance and/or itinerary of the vehicle relative to the user. Determining the relevance measure based user-related data 421 and vehicle-related data 422 differing from one another can have the advantage to provide the relevance measure with a higher accuracy and/or increased reliability. This can be vital to avoid a needless alert to the user in cases in which a featureive probability that the user is endangered by a vehicle is rather low and/or the user is already aware of a potentially dangerous situation.

FIG. 10 illustrates exemplary operations that may be controlled by operation controller 427 depending on the relevance measure determined by relevance measure determiner 435. Operation controller 427 comprises a warning notification control module 461 and/or an audio property control module 463 and/or a venting control module 466. Warning notification control module 461 is configured to initiate a warning notification output by the hearing device to the user. Audio property control module 463 is configured to modify a property of an audio signal output to the user by audio transducer 107. Venting control module 466 is configured to modify an effective size of a venting channel included in the hearing device. Any of operations 461, 463, 466 controlled by operation controller 427 can be suitable to alert the user about a vehicle by which the user may be endangered.

FIG. 11 illustrates examples of different properties of an audio signal which may be outputted to the user by audio transducer 107. Any of those properties may be determined by processing unit 420. For instance, the properties may be identified based on a signal processing performed by processing unit 420 on the audio signal and/or information provided by sound sensor 411 and/or by identifying a source from which the audio signal has been received by the processing unit. To illustrate, when the audio signal is received via communication unit 105, 205 and/or via sound sensor 202 as a source, the processing unit may identify properties of the audio signal which may be associated with the source. As illustrated, different properties of an audio signal may comprise a type 471 and/or an origin 472 and/or a volume 473 and/or a directivity 474 and/or a timing 475 of the audio signal and/or a content 477 represented by the audio signal and/or an amount 478 of the respective content 477 represented by the audio signal. The audio properties may further comprise an active noise cancelling (ANC) 478, which may be performed by outputting the audio signal. The audio properties may further comprise a frequency 479 of a sound represented by the outputted audio signal.

Audio type 471 may comprise information whether the outputted audio signal is based on a sound that has been detected by sound sensor 411 and/or whether the outputted audio signal is based on an audio signal that has been communicated to hearing device 100 and/or remote device 200 via communication unit 105, 205. The detected sound may be representative of a sound detected in an ambient environment of the user. The communicated audio signal may be communicated from an external audio source, for instance via an RF signal. For example, the communicated audio signal may comprise a phone call signal and/or a streaming signal which may be constantly received and outputted to the user while delivered from an audio provider, such as a phone call signal provider and/or a streaming media provider. The audio signal may also be communicated from remote device 200 to hearing device 100 via communication units 105, 205. For instance, the communicated audio signal may be based on sound data which may be stored in a memory and/or a medium implemented in remote device 200 and/or an audio signal received by communication unit 205 of remote device 200 from an external audio source.

A risk for the user to be endangered by a vehicle in its vicinity can depend on audio type 471 of the audio signal outputted to the user. To illustrate, on the one hand, an audio signal based on sound detected by sound sensor 411 can comprise an audio feature that may alert the user about the vehicle such as a sound emitted by the vehicle in the ambient environment of the user. On the other hand, an audio signal communicated from an external audio source may distract the user from the sounds in his ambient environment and/or may render a sound emitted by a vehicle less noticeable. The relevance measure may be determined to be indicative of a higher probability that the user is endangered by a vehicle when the outputted audio signal as at least partially based on a communicated audio signal as compared to the outputted audio signal solely based on detected sound.

Audio origin 472 may comprise information whether the outputted audio signal is representative of a sound detected at the location of the user and/or a sound detected at a different location. For instance, a locally detected sound may comprise a sound detected by sound sensor 411 implemented in hearing device 100 worn by the user and/or in remote device 200 stationary with the user. A non-locally detected sound may comprise a sound detected by a sound sensor distant from hearing device 100 and/or remote device 200. For instance, the non-locally detected sound may be detected by a sound sensor worn by a significant other of the user and/or a sound sensor stationary with the earth. The relevance measure may be determined to be indicative of a higher probability that the user is endangered by a vehicle when the outputted audio signal is at least partially representative of a non-locally detected sound as compared to the outputted audio signal solely representative of locally detected sound.

Audio volume 473 may comprise information about a volume level of the outputted audio signal. In some instances, the relevance measure may be determined to be indicative of a lower probability that the user is endangered by a vehicle when the outputted audio signal has a higher level as compared to the outputted audio signal having a lower level. For instance, when the outputted audio signal is indicative of a sound of emitted by a vehicle in a vicinity of the user such as a sound detected in an ambient environment of the user, the probability may be determined lower when the volume is higher. In some instances, the relevance measure may be determined to be indicative of a higher probability that the user is endangered by a vehicle when the outputted audio signal has a higher level as compared to when the outputted audio signal has a lower level. For instance, when the outputted audio signal does not represent a sound emitted by a vehicle in a vicinity of the user, for example an audio signal communicated from an external audio source, the probability may be determined higher when the volume is higher.

Audio directivity 474 may comprise information about a directivity of the outputted audio signal. The directivity may be provided by an acoustic beamforming performed by processing unit 420 based on a sound detected at multiple spatial locations. The directivity may be provided in an adaptive manner, for instance depending on a noise level prevailing in the ambient environment, and/or in a fixed manner, for instance during fitting of the hearing device and/or according to a setting of the hearing device selected by the user. In some instances, the relevance measure may be determined to be indicative of a higher probability that the user is endangered by a vehicle when the outputted audio signal has a higher directivity as compared to when the outputted audio signal has a lower directivity and/or substantially no directivity, for instance when the outputted audio signal is omnidirectional. To illustrate, when the directivity of the outputted audio signal is prone to suppress a sound emitted by a vehicle in a vicinity of the user, for instance when the directivity is directed toward a front of the user and/or a conversation partner talking with the user, the user may be at a higher risk of ignoring a potentially dangerous vehicle. In some instances, processing unit 420 may be configured to evaluate the directivity of the outputted audio signal relative to a location and/or moving direction and/or itinerary of a vehicle in a vicinity of the user and/or a predicted impact location of the vehicle with the user. The relevance measure may then be determined to be indicative of a higher probability that the user is endangered by a vehicle when the directivity of the outputted audio signal points away from the location and/or moving direction and/or itinerary of the vehicle and/or the predicted impact location as compared to when the directivity points in this direction.

Audio timing 475 may comprise information about a time at which the audio signal is output by audio transducer 107. In particular, some audio signals may be scheduled by processing unit 420 to be outputted immediately after a signal processing performed by processing unit 420 and/or a sound has been detected by sound sensor 411 and/or an audio signal has been received by communication unit 105, 205. Other audio signals may be scheduled by processing unit 420 to be outputted at a specific event such as, for instance, a sound indicating an operational state of the hearing device to the user such as a battery status and/or a ring tone of an incoming phone call. In some instances, the relevance measure may be determined to be indicative of a higher probability that the user is endangered by a vehicle when the time of outputting the audio signal coincides with a time at which a potentially dangerous vehicle has be identified by processing unit 420 and/or with a time at which other user-related data and/or vehicle-related date indicates an increased risk for the user in a current traffic situation. To illustrate, the user may be distracted by an incoming phone call and/or a battery status indication message and overlook a potentially dangerous traffic situation. In some instances, the relevance measure may be determined to be indicative of a lower probability that the user is endangered by a vehicle when the time of outputting the audio signal coincides with a time at which a potentially dangerous vehicle has be identified by processing unit 420 and/or with a time at which other user-related data and/or vehicle-related date indicates an increased risk for the user in a current traffic situation. To illustrate, the outputted audio signal scheduled at the time may be suitable to alert the user about a potentially dangerous traffic situation resulting in a reduced risk.

Audio content 476 may comprise information about a content of the outputted audio signal. In particular, the outputted audio signal may contain sound data representing an audio content of an ambient sound, in particular a sound presented to the user in an ambient environment of the user. For example, the ambient sound may be detected by sound sensor 411. The outputted audio signal may also contain a sound that is not representative of a sound in the ambient environment of the user, for instance a sound represented by an audio signal received by communication unit 105, 205 from an external audio source and/or an artificial sound such as a ring tone of an incoming phone call and/or a music content. In some instances, the relevance measure may be determined to be indicative of a lower probability that the user is endangered by a vehicle when the content of the outputted audio signal only includes an ambient sound as compared to when the content also includes a non-ambient sound, in particular when audio content 476 consists of non-ambient sound. The ambient sound contained in the outputted audio signal may also comprise various content. For instance, the ambient sound may contain a voice sound of the user and/or a person in proximity to the user. The ambient sound may also contain a background sound representing a sound prevailing in the ambient environment of the user such as a background noise. The background sound may be reduced, at least to a certain extent, when a noise reducing signal processing is performed on the audio signal. Information about audio content 476 may thus comprise information whether noise is reduced or not in the audio signal, for instance by a signal processing. The ambient sound may also contain a wind noise and/or not contain a wind noise when a wind noise canceller is activated. Information about audio content 476 may thus comprise information whether a wind noise cancellation is activated or not. The ambient sound may also contain a vehicle sound representing a sound emitted by a vehicle in the vicinity of the user. In some instances, the relevance measure may be determined to be indicative of a lower probability that the user is endangered by a vehicle when the content of the outputted audio signal substantially only includes a vehicle sound as compared to when the content also includes a voice sound and/or a background sound, in particular when the content does not include a vehicle sound.

In some instances, audio content 476 may be based on at least one sound feature extracted and/or separated from sound data included in the outputted audio signal. To this end, a digital signal processing (DSP) and/or an ML algorithm may be applied on the audio signal, in particular before and/or during and/or after outputting the audio signal. The ML algorithm may be based on a plurality of neural networks (NNs). For instance, an arrangement of NNs as disclosed in international patent application No. PCT/EP2020/051734 and/or No. PCT/EP2020/051735 and/or No. PCT/EP2020/060196 may be applied. In some instances, audio content 476 may be determined from audio type 471 and/or audio origin 472. For example, an audio signal communicated from an external audio source may be identified to contain a different content than an audio signal based on sound data detected by sound sensor 411. In some instances, audio content 476 may be determined based on a sensitivity and/or specialization of sound sensor 411 to a specific audio content 476. For example, a voice content may be determined based on sound data provided by a VAD.

Audio content amount 477 may comprise information about an amount of any of content 476 represented in the outputted audio signal. In particular, the outputted audio signal may be composed of various audio content 476. To illustrate, the outputted audio signal may comprise a first amount of ambient sound and a second amount of non-ambient sound. In some instances, the relevance measure may be determined to be indicative of a probability that the user is endangered by a vehicle depending on the amount of content 476, in particular a ratio between a first amount of a first content 476 and a second amount of a second content 476. To illustrate, the user may be less aware of a potential danger when the outputted audio signal comprises a larger amount of non-ambient sound relative to an amount of ambient sound.

A vehicle sound contained in the outputted audio signal may also comprise various content of sounds emitted by a plurality of vehicles and/or a sound emitted by a single vehicle, wherein at least one other vehicle emitting a sound may be present in a vicinity of the user. In some instances, the relevance measure may be determined to be indicative of a higher probability that the user is endangered by a vehicle when the content of the outputted audio signal does not contain a sound emitted by all vehicles in the vicinity of the user and/or does not contain a sound emitted by a vehicle prioritized by processing unit 420. A vehicle may be prioritized, for instance, when the relevance measure indicates a higher probability of the user endangered by this vehicle as compared to the relevance measure determined for another vehicle and/or when the relevance measure indicates the highest probability of the user endangered by this vehicle as compared to other vehicles. In some instances, the relevance measure may be determined to be indicative of a higher probability that the user is endangered by a vehicle when the content of the outputted audio signal does contain a plurality of amounts of sound each emitted by a different vehicle in the vicinity of the user such that an amount of a sound emitted by a vehicle prioritized by processing unit 420 is not predominantly represented and/or emphasized in the outputted audio signal.

Noise cancelling 478 may comprise information whether the outputted audio signal is employed to provide for an active noise cancelling (ANC). In some instances, the relevance measure may be determined to be indicative of a higher probability that the user is endangered by a vehicle when the outputted audio signal is employed for performing more ANC as compared to performing less ANC, in particular no ANC. To illustrate, ANC may at last partially cancel a sound emitted by a vehicle in a vicinity of the user putting the user into a higher risk. In some instances, the relevance measure may be determined to be indicative of a lower probability that the user is endangered by a vehicle when the outputted audio signal is employed for performing more ANC as compared to performing less ANC, in particular no ANC. Such a mode of operation may be particularly useful when the outputted audio signal further contains an indication of a vehicle in the vicinity of the user, in particular an emitted vehicle sound and/or a sound alerting the user about the vehicle. To illustrate, ANC may cancel any sound distracting the user from the vehicle emitted sound and/or alerting sound.

Sound frequency 479 may comprise information about a frequency of a sound represented by the outputted audio signal. Some frequencies may be harder to perceive. For instance, a lower sound frequency may be harder to perceive, in particular for elderly people.

Audio property control module 463 of operation controller 427, as illustrated in FIG. 10, can be configured to control modifying a property of the outputted audio signal depending on the relevance measure. In particular, audio property control module 463 may control modifying at least one of audio properties 471-479. Modifying audio property 471-479 can be employed as an operation alerting the user about a vehicle in its vicinity. A first operation may comprise modifying audio type 471 of at least one component of the outputted audio signal from an audio signal communicated from an external audio source to an audio signal representing a sound detected by sound sensor 411. A second operation may comprise modifying audio origin 471 of at least one component of the outputted audio signal from an audio signal representative of a sound detected at a location different than the user's location to an audio signal representative of a sound detected at the location of the user. A third operation may comprise modifying audio volume 473 and/or audio directivity 474 of at least one component of the outputted audio signal. A fourth operation may comprise modifying audio timing 475 of at least one component of the audio signal to be output by postponing the output to a later time. A fifth operation may comprise modifying audio content 476 and/or amount 477 of audio content 476 of the outputted audio signal from a non-ambient sound to an ambient sound. A sixth operation may comprise adding audio content 476 representing a sound emitted by a vehicle to the outputted audio signal and/or increasing an amount 477 of such an audio content 476 in the outputted audio signal. In particular, the sound may be selected to be emitted by a vehicle prioritized by processing unit 420. A seventh operation may comprise adjusting an ANC performed by the outputted audio signal. Any of those operations may be applied to alert a user about a vehicle in its vicinity, in particular to draw the user's attention to the vehicle.

In some implementations, audio property control module 463 is configured to modify the property of the outputted audio signal by augmenting the audio signal. Augmenting the audio signal may include emphasizing any aspect of the audio signal, in particular any of properties 471-479 in the audio signal, before outputting the audio signal. Augmenting the audio signal may also include superimposing a sound and/or sound feature on the audio signal, in particular to modify and/or emphasize audio content 476. For instance, the audio signal may represent ambient sound, which may be detected by sound sensor 411, and/or streamed audio, which may be received by communication unit 105, 205, before augmenting the audio signal. In particular, the audio signal may be augmented with information about a property of the vehicle. The augmented information may include, for instance, a motor sound emitted by the vehicle, which may be emphasized e.g. by a higher volume level and/or a different frequency as compared to the motor sound emitted by the vehicle and/or by removing other sound components from the audio signal, and/or a voice alert and/or an alarm sound. This may be employed to allow the user to more easily identify the vehicle in its vicinity. In some implementations, audio property control module 463 is configured to modify, in particular augment, the property of the outputted audio signal by augmenting the audio signal with information about a property of at least one vehicle from plurality of vehicles in the vicinity of the user.

In some implementations, audio property control module 463 is configured to modify, in particular augment, at least one property 471-479 of the outputted audio signal depending on vehicle-related data 422 including information about a property of the vehicle. For instance, the property of the vehicle may comprise a type and/or location and/or moving direction and/or speed and/or itinerary of the vehicle and/or a number of vehicles in the vicinity of the user. A first operation may comprise modifying audio directivity 474 depending on the vehicle property. In particular, the directivity modification may be performed depending on a dynamic property of the vehicle and/or a dynamic property of the vehicle relative to a dynamic property of the user. To illustrate, the audio signal may be spatialized. The outputted audio signal may then be provided with a directivity depending on the location and/or moving direction and/or itinerary of the vehicle and/or depending on the location and/or moving direction and/or itinerary of the vehicle relative to the location and/or moving direction and/or itinerary of the user. The user may thus be informed about a direction from which the vehicle is approaching the user. A second operation may comprise modifying audio volume 473 depending on the vehicle property. In particular, the volume level may be adapted to a type of the vehicle and/or distance of the vehicle relative to the user and/or a speed of the vehicle and/or a direction from which the vehicle is approaching the user. For instance, the volume level may be higher when the vehicle is approaching the user from behind as compared to when the vehicle is approaching the user from the front. When more than one vehicle is present in the vicinity of the user, audio volume 473 of a detected sound emitted by one of the vehicles may be altered in the outputted audio signal in order to allow the user to recognize this vehicle in addition to the other. A third operation may comprise modifying frequency 479 of a sound represented by the outputted audio signal depending on the vehicle property. In particular, when more than one vehicle is present in the vicinity of the user, a main frequency of a sound emitted by one of the vehicles may be altered in the outputted audio signal in order to allow the user to more easily distinguish between the vehicles. A fourth operation may comprise attenuating volume level 473 of a first sound feature in the audio signal relative to a volume level of a second sound feature in the audio signal, the second sound feature representing a sound emitted by the vehicle in the vicinity of the user, for instance a motor sound and/or a sound of a siren. This may comprise decreasing the volume level of the first sound feature relative to the second sound feature and/or increasing the volume level of the second sound feature relative to the first sound feature. A fifth operation may comprise superimposing a second sound feature to the audio signal containing a first sound feature. In this way, audio content 476 of the audio signal may be modified by adding an audio content represented by the second sound feature to the audio content represented by the first sound feature to the audio signal. The audio signal by thus be augmented by the second sound feature in order to attract the user's attention. For instance, the first sound feature may be representative of an ambient sound detected by sound sensor 411 and/or a sound represented by an audio signal communicated from an external audio source. The second sound feature may be selected to be suitable to attract the user's attention away from the first sound feature when perceiving the outputted audio signal.

In some implementations, audio property control module 463 is configured to modify, in particular augment, the property of the outputted audio signal depending on user-related data 421. In particular, user-related data 421 may include information about a property detected on the user and/or in an ambient environment of the user and/or a property of the hearing device 100 and/or remote device 200 operated by the user. A first operation may comprise modifying audio volume 473 depending on an environmental noise in the ambient environment of the user. For instance, an increased noise may be compensated with an increased volume level of the outputted audio signal to maintain a desired signal-to-noise ratio (SNR). A second operation may comprise modifying the property of the outputted audio signal depending on a property of hearing device 100 and/or remote device 200. The property may comprise a sensitivity of detector unit 410. For instance, audio volume 473 may be adapted to an input amplification of sound sensor 411. The property may also comprise a current setting of hearing device 100 and/or remote device 200, for instance a muting of sound sensor 411 due to wind noise.

FIG. 12 illustrates examples of different properties of a venting provided between an inner region of an ear canal of the ear at which hearing device 100 is worn and an ambient environment outside the ear canal. The venting may be provided by a venting channel included in hearing device 100. Hearing device 100 may include an active vent allowing to adjust the venting properties. In particular, an effective size of the venting channel may be adjusted by the active vent providing for an adjustment of an acoustic impedance of the venting channel. In this way, a venting amount 481 of sound waves vented between the inner region of the ear canal and the ambient environment can be adjusted. The active vent may be controlled by processing unit 420.

The active vent may be controlled between different states each providing for a different effective size of the venting channel. A first state of the active vent may correspond to a fully reduced effective size of the venting channel in which the venting channel is substantially closed. In the first state, natural sound entering the venting channel from the ambient environment can be substantially blocked from entering the inner region of the ear canal. In consequence, substantially no air-conducted natural sound but the audio signal outputted by audio transducer 107 may be perceivable by the user at the ear at which hearing device 100 is worn. A second state of the active vent may correspond to a less reduced effective size of the venting channel in which the venting channel is partially open. In the second state, natural sound may enter the ear canal from the ambient environment through the venting channel to a limited extent. A smaller amount of the air-conducted natural sound and the audio signal outputted by audio transducer 107 may thus be perceivable by the user. A third state of the active vent may correspond to a non-reduced effective size of the venting channel in which the venting channel is fully open. A larger amount of the air-conducted natural sound and the audio signal outputted by audio transducer 107 may thus be perceivable by the user. In some instances, when the active vent is in the second state or in the third state, audio transducer 107 may be controlled to output no audio signal such that only natural sound may be perceivable by the user. In some instances, when the active vent is in the first state, audio transducer 107 may be controlled to output no audio signal such that substantially no sound with the exception of a bone-conducted sound may be perceivable by the user.

Venting control module 466 of operation controller 427, as illustrated in FIG. 10, can be configured to control adjusting an effective size of a venting channel included in the hearing device depending on the relevance measure. In particular, venting control module 466 may control the active vent to be switched between the different states. Adjusting the effective size of the venting channel can be employed as an operation alerting the user about a vehicle in its vicinity. A first operation may comprise increasing the effective size of the venting channel. A natural sound from the ambient environment perceivable by the user may thus alert the user about the vehicle. A second operation may comprise decreasing the effective size of the venting channel and controlling audio transducer 107 to output an audio signal alerting the user about the vehicle. The user may thus be prompted to focus its attention to the alert due to a decrease and/or absence of the natural sound from the ambient environment. A third operation may comprise increasing the effective size of the venting channel and controlling audio transducer 107 to output an audio signal representative of sound detected in the ambient environment. The user may thus be alerted by the natural sound and the outputted audio signal complementing each other. In particular, the outputted audio signal may be modified in order to enhance sound features detected in the ambient environment alerting the user, for instance by increasing the volume of a sound emitted by the vehicle.

FIG. 13 illustrates examples of different warning notifications 482 that may be controlled to be initiated by warning notification control module 461 of operation controller 427, as illustrated in FIG. 10. Warning notifications 482 may comprise a voice alert and/or a warning tone and/or a vibration of hearing device 100 evoking a tactile perception of the user. The voice alert may be implemented as an artificial voice speaking to the user. The voice alert may include a voice message providing information about a property the vehicle, for instance a vehicle type. The warning tone may be implemented as any noticeable sound attracting the user's attention. A plurality of different warning tones may be stored in a memory of hearing device 100 and/or remote device 200. An audio signal representing the warning tone may also be communicated from the vehicle in the vicinity of the user to hearing device 100 and/or remote device 200 via communication unit 105, 205. For instance, a siren may be streamed from an emergency vehicle to hearing device 100 and/or remote device 200 as a warning tone. Different warning tones may be associated with different properties of a vehicle, for instance a vehicle type. The user may select a preferred warning tone via a user interface, in particular a preferred warning tone for each of a plurality of different vehicle properties. In some implementations, an audio signal representing the voice alert and/or the warning tone can be spatialized in accordance with a location and/or moving direction and/or itinerary of the vehicle before outputting the audio signal. The voice alert and/or the warning tone can thus be provided with a directivity indicating the location and/or moving direction and/or itinerary from which the vehicle is approaching the user. The vibration may be produced by a vibrator included in hearing device 100.

Any of these warning notifications 482 can be employed as an operation alerting the user about a vehicle in its vicinity. A first operation may comprise initiating the warning notification, in particular at a rather low volume and/or at a rather low vibration intensity, under continuation of outputting an audio signal and/or an audio signal component currently output by audio transducer 107. A second operation may comprise initiating the warning notification, in particular at a rather high volume and/or at a rather high vibration intensity, wherein a volume of an audio signal and/or an audio signal component unrelated to an alert currently outputted by audio transducer 107 may be reduced. A third operation may comprise initiating the warning notification, wherein audio transducer 107 is controlled to stop outputting an audio signal and/or an audio signal component unrelated to an alert for the user.

Figure 14:
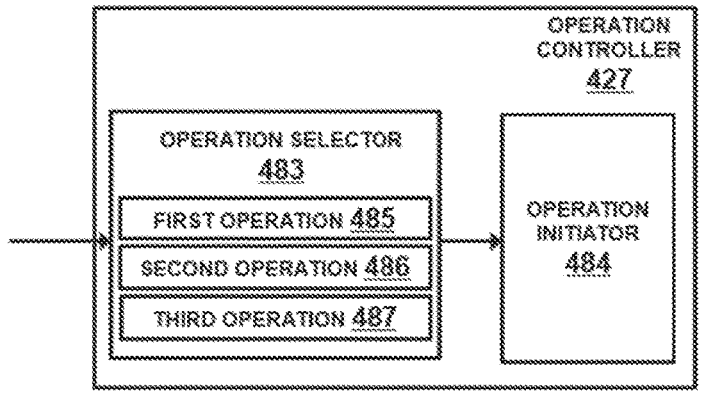
FIG. 14 schematically illustrates some exemplary configurations of the hearing device illustrated in FIGS. 2, 4 and/or the electronic device illustrated in FIG. 4 to control an operation alerting the user about a vehicle.

FIG. 14 depicts a functional block diagram of an exemplary implementation of operation control module 427. Operation control module 427 may be executed by processing unit 420 in the algorithm shown in FIG. 8. As illustrated, operation control module 427 comprises an operation selection module 483, and an operation initiation module 484. Operation selection module 483 is configured to select an operation from a plurality of operations including a first operation 485 and a second operation 486, and may include additional operations such as a third operation 487. Each of operations 485-487 can alert the user about a vehicle in its vicinity. In particular, operations 485-487 may be implemented as any operation that may be controlled by audio property control module 463 and/or venting control module 466 and/or warning notification control module 461, for instance any of the exemplary operations described above.

Operations 485-487 may be distinguished in that they are configured to evoke a different degree of alertness by the user. In particular, each of operations 485-487 may alert the user by attracting a different degree of attentiveness of the user. For instance, third operation 487 may only attract the attention of the user to a degree by which the user does hardly feel interrupted from pursuing another activity, second operation 486 may attract the attention of the user to a degree by which the user may feel disturbed but still be able to continue pursuing an ongoing activity, and first operation 485 may attract the attention of the user to a degree by which the user is deflected from pursuing an ongoing activity under any normal daily occurring circumstances.

To give an illustrative example, third operation 487 may be performed by audio property control module 463 controlling modifying a property of an audio signal currently outputted by audio transducer 107 to a degree by which the outputted audio signal further contains the same content as before. For instance, the outputted audio signal may be modified by adding additional content, such as a warning tone. The outputted audio signal may also be modified by changing a property such as audio volume 473, for instance decreasing a volume level of an audio signal communicated by an external audio source and/or increasing a volume of an audio signal representing a sound detected in the ambient environment which may include a sound emitted by a vehicle. Second operation 486 may also be performed by audio property control module 463 controlling modifying a property of a currently outputted audio signal to a degree by which a content of the currently outputted audio signal may not be further reproduced and/or by which a type 471 and/or origin 472 and/or directivity 474 and/or timing 475 and/or ANC generation 478 of the currently outputted audio signal may be altered. For instance, the outputted audio signal may be altered from an audio signal communicated by an external audio source to an audio signal representing a sound detected in the ambient environment of the user. The outputted audio signal may also be altered from an audio signal having a larger directivity to an audio signal having a smaller directivity. First operation 485 may be performed by warning notification control module 461. At the same time, the currently outputted audio signal may be terminated.

The relevance measure determined by relevance measure determining module 425, as illustrated in FIG. 8, is inputted to operation selection module 483. Operation selection module 483 can be configured to select one of operations 485-487 depending on the relevance measure. In particular, each of operations 485-487 may be associated with a different probability and/or probability range that the user is endangered by a vehicle as indicated by the relevance measure. At a lower probability and/or probability range, third operation 487 may be selected. At a medium probability and/or probability range, second operation 486 may be selected. At a higher probability and/or probability range, first operation 485 may be selected. The selected operation can then be initiated by operation initiation module 484.

As another example, operations 485-487 may be performed by audio property control module 463 by controlling an augmenting of the outputted audio signal with information about a property of the vehicle. Operations 485-487 may be distinguished by a different amount of the augmentation. To illustrate, third operation 487 may be performed by setting audio volume 473 of the outputted audio signal, which may represent a detected sound emitted by the vehicle, to a lower volume level, second operation 486 may be performed by setting the audio volume 473 to a medium volume level, and first operation 487 may be performed by setting the audio volume 473 to a higher volume level. The audio signal outputted in any of operations 485-487 can thus be augmented by a sound including a sound emitted by a vehicle at a different volume level.

As another example, at least one of operations 485-487 may comprise at least one of modifying, when an audio signal is outputted to the user by an audio transducer included in the hearing device, a directivity of the outputted audio signal such that the directivity points toward a location of the vehicle and/or a moving direction of the vehicle and/or an itinerary of the vehicle; and/or modifying, when an audio signal is outputted to the user by an audio transducer included in the hearing device, a volume level of the outputted audio signal depending on a distance of the vehicle to the user and/or a type of the vehicle and/or a speed of the vehicle and/or a direction from which the vehicle is approaching the user; and/or modifying, when an audio signal is outputted to the user by an audio transducer included in the hearing device, a frequency of a sound feature contained in the outputted audio signal, the sound feature representing a sound emitted by the vehicle in the vicinity of the user. To illustrate, third operation 487 may only perform one of the modifying of the directivity, the modifying of the volume level, and the modifying of the frequency. Second operation 486 may perform two of these. Third operation 487 may perform all three of these. In this way, a different degree of an augmentation of the outputted audio signal may be performed, wherein a higher degree of the augmentation can evoke a higher degree of alertness by the user.

Operations 485-487 can then be performed by audio property control module 463 depending on the relevance measure. The relevance measure, in turn, depends on information about a property of the vehicle included in vehicle-related data 422, for instance a type of the vehicle and/or a distance of the vehicle relative to the user and/or a speed of the vehicle and/or a direction from which the vehicle is approaching the user. For instance, when the distance of the vehicle relative to the user is smaller and/or the speed of the vehicle is larger, the relevance measure can be determined to indicate a higher probability that the user is endangered by the vehicle. Operations 485-487 can thus be selected by operation selection module 483 depending on the property of the vehicle influencing the relevance measure. For instance, when the distance of the vehicle to the user is rather large, third operation 487 may be performed and the sound emitted by the vehicle is reproduced at the lower volume level in the outputted audio signal. When the distance of the vehicle to the user is in a medium range, second operation 486 may be performed and the sound emitted by the vehicle is reproduced at the medium volume level in the outputted audio signal. When the distance of the vehicle to the user is rather small, first operation 485 may be performed and the sound emitted by the vehicle is reproduced at the higher volume level in the outputted audio signal. Augmenting the outputted audio signal in such a way with information about the distance of the vehicle can allow the user to more easily identify the vehicle in its vicinity.

The above described implementations of operation control module 427 may be employed to balance the user's interests of reliably becoming alerted about a potentially risky traffic situation, and of not being overloaded or annoyed by too many or needless alerts. In particular, a mildest measure for alerting the user may thus be achieved by still maintaining a desired degree of road safety. The mildest measure can be provided by operation control module 427 by relating a different level of attention evoked by the operations 485-487 to a respective probability that the user is endangered by a vehicle, as indicated by the relevance measure. For instance, when the user ignores any of the operations provoking a lower level of attention, the probability that the user is endangered by the vehicle may increase, as may be indicated by a newly determined relevance measure, such that selecting any of the other operations provoking a higher level of attention seems appropriate.

Figure 15:
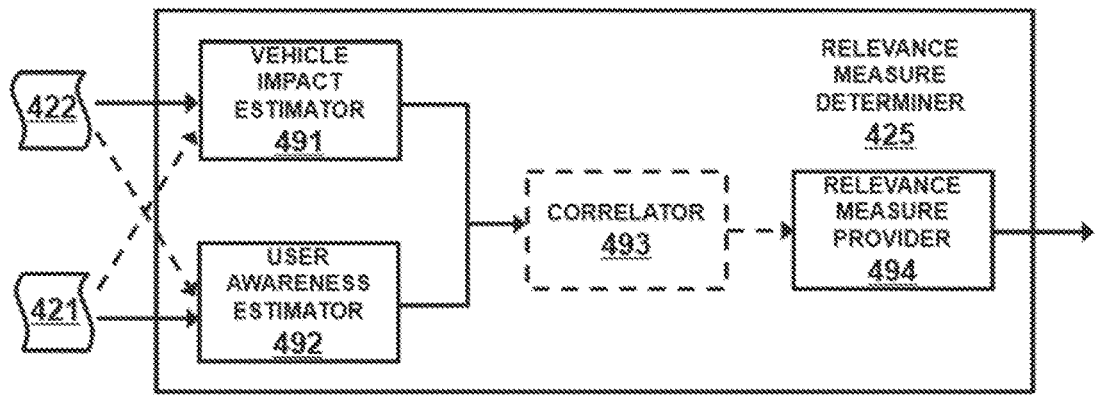
FIG. 15 schematically illustrates some exemplary configurations of the hearing device illustrated in FIGS. 2, 4 and/or the electronic device illustrated in FIG. 4 to determine a relevance measure indicative of a probability that the user is endangered by a vehicle.

FIG. 15 depicts a functional block diagram of an exemplary implementation of relevance measure determining module 425. Relevance measure determining module 425 may be executed by processing unit 420 in the algorithm shown in FIG. 8. Relevance measure determining module 425 comprises a vehicle impact estimation module 491, a user awareness estimation module 492, and a relevance measure provision module 494. Relevance measure determining module 425 may further comprise a correlation module 493. Vehicle impact estimation module 491 can be configured to determine a probability that a vehicle in a vicinity of the user will impact the user, for instance by estimating a proximity or a likelihood of collision of the vehicle with the user and/or a vehicle driven by the user. To this end, vehicle-related data 422 is inputted to vehicle impact estimation module 491. In addition, user-related data 421 may be inputted to vehicle impact estimation module 491. To illustrate, the probability that the vehicle will impact the user may not only depend on a property of the vehicle, for instance a dynamic property and/or intrinsic property of the vehicle, but also on a property of the user, for instance a dynamic property and/or intrinsic property of the user.

User awareness estimation module 492 can be configured to determine a probability that the user is aware of a vehicle in its vicinity. To this end, user-related data 421 is inputted to user awareness estimation module 492. In addition, vehicle-related data 421 may be inputted to user awareness estimation module 492. To illustrate, the probability that the user is aware of the vehicle may not only depend on a property of the user and/or its environment, for instance a physical condition of the user and/or a visibility range, but also on a property of the vehicle, for instance a type, size, movement speed, and/or emitted sound.

Correlation module 493 may be employed to correlate an output of vehicle impact estimation module 491 with an output of user awareness estimation module 492. In particular, correlation module 493 may be configured to ensure that the user's awareness about a vehicle, as estimated by user awareness estimation module 492, is associated with the vehicle potentially impacting the user, as estimated by vehicle impact estimation module 491. Relevance measure provision module 494 can be configured to provide the relevance measure indicative of a probability that the user is endangered by the vehicle by taking into account both the probability that the vehicle will impact the user and the probability that the user is aware of the vehicle.

Vehicle impact estimation module 491 may be configured to perform at least one of the following exemplary operations to determine a probability that a vehicle will impact the user: In some instances, vehicle impact estimation module 491 can be configured to take into account a dynamic property of the vehicle indicated by vehicle-related data 422, for instance a location and/or a speed and/or a moving direction and/or an itinerary and/or a proximity and/or a distance and/or a presence of the vehicle in the vicinity of the user. In some instances, vehicle impact estimation module 491 can also be configured to take into account a dynamic property of the user indicated by user-related data 421, for instance a location of the user and/or a speed of the user and/or a moving direction of the user and/or an itinerary of the user. In some instances, vehicle impact estimation module 491 can be configured to take into account a dynamic property of the vehicle relative to the user indicated by user-related data 421 and/or vehicle-related data 422, for instance a distance and/or proximity and/or presence of the vehicle relative to the user and/or a predicted impact location of the vehicle with the user and/or an orientation of the user relative to the vehicle. For instance, only a vehicle approaching the user from behind and/or from the side may be selected to be of interest. In some instances, vehicle impact estimation module 491 can be configured to take into account an intrinsic property of the vehicle indicated by vehicle-related data 422, such as a type of the vehicle. For example, the vehicle impact probability may be determined depending on a recognizability of the vehicle. To illustrate, a type of a vehicle that may be hard to recognize by the user by an emitted sound, such as an EV, may be determined to have a larger vehicle impact probability. The vehicle impact probability may also be determined depending on a magnitude of harm which a vehicle may potentially inflict on the user. To illustrate, a type of a vehicle driven by a larger propelling force and/or having a larger mass, such as a car or a truck, and/or a vehicle driving at higher speed may cause a higher damage to the user as compared to a less powerful and/or lighter and/or slower vehicle, such as a bike. As another example, information may be gathered whether the user is passing a street with a lighting system, in particular whether the lighting is red or green, and/or whether the user is passing a crosswalk or a random place of the street. The vehicle impact probability may depend on any of those circumstances.

Figure 16:
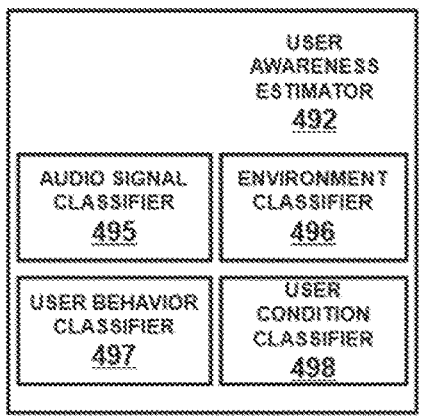
FIG. 16 schematically illustrates some exemplary configurations of the hearing device illustrated in FIGS. 2, 4 and/or the electronic device illustrated in FIG. 4 to determine a probability that the user is aware of a vehicle.

FIG. 16 illustrates exemplary operations that may be performed by user awareness estimation module 492 to determine the probability that the user is aware of a vehicle in its vicinity. As illustrated, user awareness estimation module 492 comprises an audio signal classification module 495 and/or an environment classification module 496 and/or a user behavior classification module 497 and/or a user condition classification module 498. Audio signal classification module 495 can be configured to classify the user's awareness based on a property of an audio signal outputted to the user by audio transducer 107. In particular, any of audio properties 471-479 illustrated in FIG. 11 may be employed to determine a resulting impact on the user's awareness. For instance, the probability that the user's awareness is affected by various audio properties 471-479 may be based on some of the examples described above in conjunction with FIG. 11.

Environment classification module 496 can be configured to classify the user's awareness based on a property of an ambient environment of the user. In particular, user-related data 421 indicative of a property detected in the ambient environment of the user may be employed to determine a resulting impact on the user's awareness. To this end, user-related data 421 may be provided by detector unit 410, for instance by environment sensor 416 and/or sound sensor 411 and/or radio sensor 412 and/or optical sensor 413. User-related data 421 may also be provided by communication unit 105, 205, for instance in the form of GPS data and/or data received via a cellular data network and/or a computer network. The property detected in the ambient environment and/or received via communication unit 105, 205 may comprise information about a current traffic situation at the location of the user. For instance, information may be gathered whether the user is located in a rather dense and/or dynamic traffic situation or whether the user is moving through rather unpopulated streets. Furthermore, information may be gathered whether the road environment itself is rather confusing, in particular due to a large number of vehicles parked on the side and/or bad viewing conditions, or whether the road environment is rather transparent for the user. Depending on the traffic situation and/or road environment, it may be easier or harder for the user to become aware of a vehicle in its vicinity. The user's awareness may thus be classified as higher or lower. The property detected in the ambient environment and/or received via communication unit 105, 205 may also comprise information about a current weather and/or climate-induced visibility obstructions and/or daylight conditions. The user's awareness may then be classified accordingly. The property detected in the ambient environment may also comprise a sound, in particular a noise level prevailing in the ambient environment. Increased noise makes it harder for the user to hear an approaching vehicle. The user's awareness may then be classified accordingly.

User behavior classification module 497 can be configured to classify the user's awareness based on a current behavior of the user and/or a behavior of the user that may be correlated with a property of a vehicle in its vicinity. In particular, user-related data 421 indicative of a property detected on the user and/or in the ambient environment of the user may be employed to determine a resulting impact on the user's awareness. In some instances, vehicle-related data 422 may be employed in addition to user-related data 421. User-related data 421 may be provided by detector unit 410, for instance by movement sensor 414 and/or physiological sensor 415 and/or sound sensor 411. User-related data 421 may also be provided by communication unit 105, 205. The property of the user may comprise information about a movement of the user, in particular a movement of the user's body and/or the user's head and/or the user's eye gaze. Such a movement may be determined based on user-related data 421 provided by movement sensor 414 and/or physiological sensor 415 and/or user-related data 421 received by communication unit 105, 205, for instance via a cellular network and/or GPS data. The movement of the user's body may comprise a translational and/or rotational movement. The movement of the user may also comprise a recurring pattern of a movement activity. For instance, the pattern may be indicative of a walking activity and/or a cycling activity and/or a skating activity and/or an activity of the user riding a scooter. The property detected on the user may also comprise information about a sound, in particular an own voice activity of the user. The property detected on the user may also comprise a biometric property, for instance an EEG and/or EOG and/or pupillometry measurement.

In some implementations, a direction of a rotation of the user, in particular of the user's body and/or the user's head, and/or an eye gaze movement of the user and/or an orientation of the user's head and/or body is determined relative to a dynamic property of a vehicle in the vicinity of the user. The dynamic property may comprise a location and/or a moving direction and/or an itinerary of the vehicle and/or a predicted impact location of the vehicle with the user. Depending on the determined direction of the rotation and/or eye gaze movement and/or orientation, the user's awareness may be classified as higher or lower. To illustrate, a behavior of the user turning his head or body toward an approaching vehicle can indicate that the user has taken notice of the vehicle. A different behavior may indicate that the user is not aware of such a vehicle.

In some implementations, a direction of the orientation of the user's head relative to the surface of the earth is determined. Depending on the determined direction of the orientation relative to a direction parallel to the earth's surface, the user's awareness may be classified as higher or lower. To illustrate, a behavior of the user turning his head toward the surface of the earth can indicate that the user is distracted, for instance by looking at a mobile device in his hands and/or by having lost his thoughts during walking, or that the user may be fallen asleep during driving a car. Consequently, the user's awareness may then be classified lower as compared to when the user's looking straight ahead in parallel to the floor.

In some implementations, a direction and/or a speed of a translational movement of the user and/or a pattern of a walking activity and/or cycling activity and/or skating activity and/or activity of riding a scooter is determined. Depending on determined changes of the direction and/or speed of the translational movement and/or the pattern, the user's awareness may be classified as higher or lower. To illustrate, a behavior of the user suddenly changing his movement behavior when a vehicle appears in its vicinity can indicate that the user has taken notice of the vehicle. An unchanged behavior may indicate that the user is unaware of the vehicle.

In some implementations, a reaction of the user to an operation alerting the user about the vehicle controlled by operation controller 427 is determined. The reaction may be determined based on user-related data 421 provided by movement sensor 414 and/or physiological sensor 415. Depending on the reaction, the user's awareness may be classified as higher or lower. To illustrate, a reaction of the user to the alert, which may be determined based on movement data and/or biometric data, can indicate that the user has taken notice of the vehicle.

In some implementations, a presence of a voice of the user and/or a person next to the user is determined. The voice may be determined based on user-related data 421 provided by sound sensor 411, for instance a microphone and/or a VAD. Depending on the presence of the voice, the user's awareness may be classified as higher or lower. To illustrate, a presence of a voice can indicate that the user is distracted by being involved in a conversation.

User condition classification module 498 can be configured to classify the user's awareness based on a physical and/or mental condition of the user. User-related data 421 indicative of a property detected on the user and/or in the ambient environment of the user may be employed to determine a resulting impact on the user's awareness. User-related data 421 may be provided by detector unit 410, for instance by movement sensor 414 and/or physiological sensor 415 and/or sound sensor 411. User-related data 421 may also be provided by communication unit 105, 205.

In some implementations, the property of the user comprises a level of fatigue of the user. A fatigue, as used herein, includes a physical and/or mental condition of fatigue. For instance, the fatigue can be caused by a physical exhaustion and/or a cognitive load and/or a lack of sleep. The level of fatigue, as determined by user condition classification module 498, may constitute a physical and/or mental condition of the user. The level of fatigue may be determined in various ways, which may include user-related data 421 provided by movement sensor 414 and/or physiological sensor 415 and/or sound sensor 411. In particular, a physical condition of fatigue may be determined based on data provided by movement sensor 414 and/or a biometric sensor included in physiological sensor 415. Movement data provided by movement sensor 414 can indicate a physical exhaustion of the user, for instance when movements have been continuously performed by the user for a prolonged time. The biometric sensor may be configured to provide biometric data indicative of a heart rate and/or blood pressure and/or heart rate variability (HRV) which can indicate a current physical exhaustion and/or mental stress level impacting the user's fatigue. For instance, the biometric data may be provided by a PPG sensor and/or an ECG sensor implemented in hearing device 100. The biometric sensor may also be configured to provide biometric data indicative of a body temperature and/or dehydration which can also impact the user's fatigue. A mental status of fatigue, for instance a cognitive load and/or lack of sleep, may be determined by biometric data provided by an EEG sensor and/or an EOG sensor implemented in hearing device 100. Moreover, a pupillometry measurement may be employed. The level of fatigue may also be determined based on sound data provided by sound sensor 411. The sound data may be analyzed with respect to indicators of the user's fatigue. For instance, a voice of the user may indicate a physical and/or emotional condition of the user impacting its fatigue. Detecting the user's voice may be performed by a VAD and/or by separating the user's voice from sound data provided by a microphone. As another example, sound detected in the ambient environment over a prolonged time period, for instance the past hour, can indicate how exhausting a hearing situation for the user was impacting its current fatigue.

In some implementations, the property of the user comprises a health condition of the user. The health condition, as determined by user condition classification module 498, may constitute a physical and/or mental condition of the user. The health condition may comprise a hearing loss. User-related data 421 indicative of the hearing loss may include a setting of hearing device 100 employed by the user. The setting may comprise, for instance, a level of amplification provided by hearing device 100 when outputting a sound detected in the ambient environment. User-related data 421 indicative of the hearing loss may also include information provided by the user and/or a health care provider, which may be entered via a user interface. In particular, the health condition may comprise an asymmetric hearing loss in which one ear of the user has a better hearing performance and the other ear has a worse hearing performance. The asymmetric hearing loss may lead to a higher risk for the user when a vehicle is approaching the user from the side of the ear with the worse hearing performance as compared to the side of the other ear with the better hearing performance. User condition classifier 498 may thus take into account from which side the vehicle is approaching the user when determining the probability that the user is aware of a vehicle in its vicinity.

The health condition may also comprise a fitness level of the user. The fitness level may be determined based on data provided by a biometric sensor included in physiological sensor 415. For instance, a $VO_2$ max value and/or an aerobic fitness level may be determined based on biometric data provided by a PPG sensor and/or an ECG sensor. User-related data 421 indicative of the fitness level may also include information provided by the user and/or a health care provider, such as an age of the user, which may be entered via a user interface. The health condition may also comprise a narcotization level of the user, for instance a blood alcohol level. A blood content indicative of a narcotization level may be determined based on biometric data provided by a PPG sensor.

The health condition may also include a cognitive impairment. The cognitive impairment may be caused by a physiological disorder such as dementia and/or attention deficit hyperactivity disorder (ADHS) and/or age. Dementia may be predominantly diagnosed for elderly people. ADHS may also be relevant for children. Both, elderly people and children represent age groups that are exposed to a higher risk in traffic, which can be enhanced by a physiological disorder. A cognitive impairment may be determined based on movement patterns detected on the user by a movement sensor, for instance when the user takes a long time to perform a rather simple movement such as a double tapping on the hearing device, and/or biometric data provided by an EEG sensor. The health condition may also include a physical impairment. A physical impairment may be determined based on movement patterns detected on the user by a movement sensor, for instance the user walking slow.

In some implementations, the health condition may be correlated with the level of fatigue of the user. To illustrate, the user's level of fatigue may have a smaller impact on the user's awareness when the user is in a good health condition.

Figure 17:
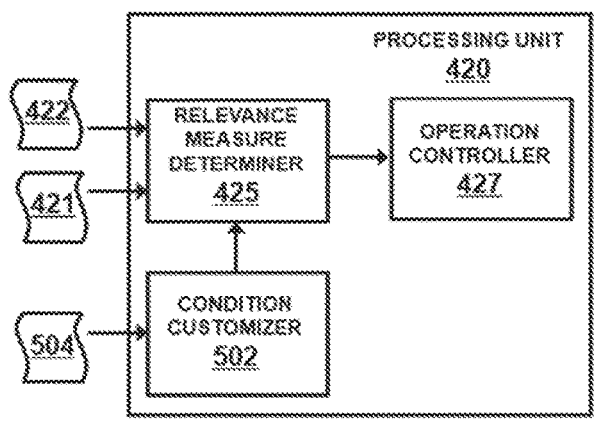
FIG. 17 schematically illustrates some exemplary configurations of the hearing device illustrated in FIGS. 2, 4 and/or the electronic device illustrated in FIG. 4 to determine a relevance measure, and to control an operation alerting the user about a vehicle depending on the relevance measure.

FIG. 17 illustrates a functional block diagram of an exemplary sensor data processing algorithm that may be executed by processing unit 420. As illustrated, the algorithm comprises relevance measure determining module 425 and operation control module 427, in accordance with the algorithm illustrated in FIG. 8. User-related data 421 and vehicle-related data 422 is inputted in relevance measure determining module 425. The algorithm further comprises a condition customization module 502. Condition customization module 502 is configured to customize a condition evaluated by relevance measure determining module 425. During the evaluation, relevance measure determining module 425 can determine whether user-related data 421 and/or vehicle-related 422 data fulfills the condition. The relevance measure can then be determined depending on the condition being fulfilled.

Customizing the condition by module 502 can be employed to restrict the controlling of the alert operation by operation controller 427 to a specific context. The context may be selected such that, in traffic situations in which operations alerting the user can be perceived as unnecessary and/or undesired, such alert operations can be avoided. The restriction of the context may depend on any user-related data 421 and/or vehicle-related 422. The condition customized by customization module 502 may be a boundary condition for the context which must be fulfilled to control the alert operation by operation controller 427. In this way, customization module 502 may be employed to balance the user's interests of reliably becoming alerted about a potentially risky traffic situation, and of not being overloaded or annoyed by too many or needless alerts.

Condition customization module 502 can be configured to perform the customization based on customization data 504 which may be inputted to module 502. Customization data 504 may be any data containing information and/or parameters and/or instructions for customizing the condition. In some implementations, customization data 504 can be inputted by the user via a user interface. Hearing device 100 and/or remote device 200 may include the user interface. For instance, the user interface may be implemented as a voice command interpreter included in hearing device 100 and/or touchscreen 224 included in remote device 200. In this way, the user may enter personal preferences and/or context-relevant information that can be employed to customize the condition. In some implementations, customization data 504 can be communicated from a data source distant from the user, for instance by an RF signal. Customization data 504 may be received by processing unit 402 via communication unit 105, 205. For instance, customization data 504 may be stored in central server and/or cloud 216 and transmitted to hearing device 100 and/or remote device 200 via a cellular data network and/or a computer network. Customization data 504 stored in central server and/or cloud 216 may include data provided by the user and/or data comprising context-relevant information, for instance information about the user, a local traffic situation, weather, and/or the like. In some instances, customization data 504 can be provided by an ML algorithm, which may be trained based on data collected from a multitude of users.

In this way, condition customization module 502 can be configured to perform a customization of the condition during operation of hearing device 100 and/or remote device 200. In particular, the customization of the condition may be performed during daily usage of device 100, 200 and/or after turning on device 100, 200, for instance during a boot process, and/or during an initial setup of device 100, 200. In some instances, a previous customization may be updated by providing new customization data 504 any time.

Figure 18:
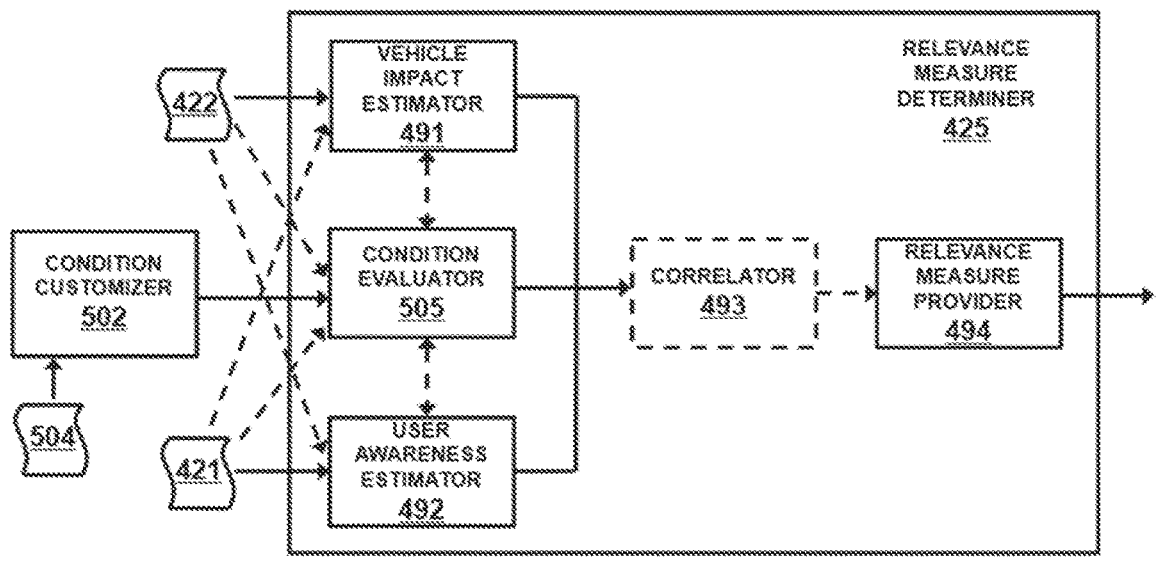
FIG. 18 schematically illustrates some exemplary configurations of the hearing device illustrated in FIGS. 2, 4 and/or the electronic device illustrated in FIG. 4 to determine a relevance measure indicative of a probability that the user is endangered by a vehicle.

FIG. 18 depicts a functional block diagram of an exemplary implementation of relevance measure determining module 425. Relevance measure determining module 425 may be executed by processing unit 420 in the algorithm shown in FIG. 17. Relevance measure determining module 425 comprises vehicle impact estimation module 491, user awareness estimation module 492, and relevance measure provision module 494, and may further comprise correlation module 493, in accordance with the implementation of relevance measure determining module 425 illustrated in FIG. 15. Relevance measure determining module 425 further comprises a condition evaluation module 505. Condition evaluation module 505 is configured to evaluate the condition customized by condition customization module 502. To this end, user-related data 421 and/or vehicle-related data 422 can be inputted to condition evaluation module 505. Additionally or alternatively, the vehicle impact probability determined by vehicle impact estimation module 491 based on vehicle-related data 422 and/or user-related data 421 can be inputted to condition evaluation module 505. Additionally or alternatively, the user awareness probability determined by user awareness estimation module 492 based on user-related data 421 and/or vehicle-related data 422 can be inputted to condition evaluation module 505. Condition evaluation module 505 can thus be configured to determine whether user-related data 421 and/or vehicle-related data 422 and/or the vehicle impact probability and/or user awareness probability fulfills the condition.

Relevance measure provision module 494 can then determine the relevance measure depending on whether the condition is fulfilled, as determined by condition evaluation module 505, and/or the vehicle impact probability, as determined by vehicle impact estimation module 491, and/or the user awareness probability, as determined by user awareness estimation module 492. In some instances, the relevance measure may be determined to be indicative of a zero probability when the condition is determined to be not fulfilled, wherein the vehicle impact probability and the user awareness probability may not be further taken into account. In some instances, the relevance measure may be determined to be indicative of a non-vanishing probability when the condition is determined to be not fulfilled, which probability may be reduced as compared to when the condition is determined to be fulfilled, wherein the vehicle impact probability and the user awareness probability may be further taken into account.

In some implementations, as illustrated, condition evaluation module 505 can be configured to provide the information whether the condition is fulfilled to vehicle impact estimation module 491 and/or user awareness estimation module 492. The vehicle impact probability and/or the user awareness probability can then be determined depending on whether the condition is fulfilled or not. To illustrate, in some instances, when the condition is fulfilled or not fulfilled, an estimation of the vehicle impact probability and/or the user awareness probability may not be required to determine the relevance measure by relevance measure provision module 494. In those cases, vehicle impact estimation module 491 and/or user awareness estimation module 492 may be disabled in order to not provide a contribution to the relevance measure provided by relevance measure provision module 494. In the illustrated example, vehicle impact estimation module 491, user awareness estimation module 492, and condition evaluation module 505 are applied in a parallel operation. It may also be that condition evaluation module 505 is applied in a sequential operation with vehicle impact estimation module 491 and/or user awareness estimation module 492. For example, depending on whether condition evaluation module 505 yields that the condition is fulfilled or not, impact estimation module 491 and/or user awareness estimation module 492 may be operated subsequently or not.

Figure 19:
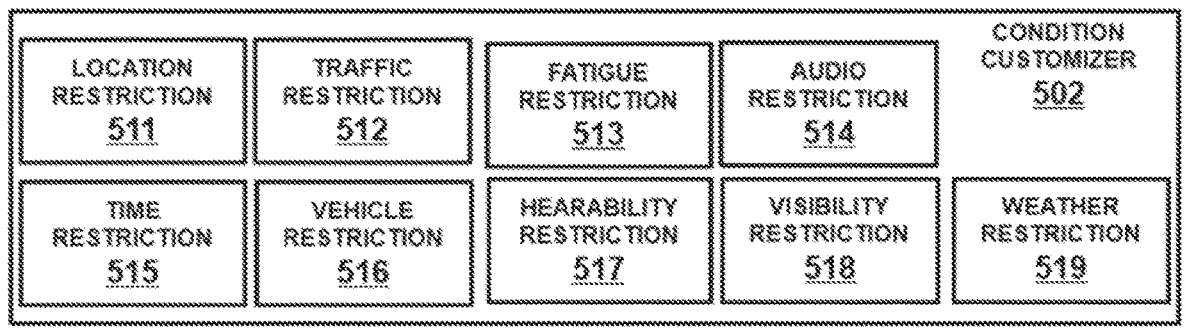
FIG. 19 schematically illustrates some exemplary configurations of the hearing device illustrated in FIGS. 2, 4 and/or the electronic device illustrated in FIG. 4 to customize a condition depending on which an operation alerting the user about a vehicle can be controlled.

FIG. 19 illustrates examples of different restrictions of the operation controlled by operation controller 427 to alert the user to a specific context. The restrictions comprise a location restriction 511 and/or a traffic restriction 512 and/or a fatigue restriction 513 and/or an audio restriction 514 and/or a time restriction 515 and/or a vehicle restriction 516 and/or an audibility restriction 517 and/or a visibility restriction 518 and/or a whether restriction 519. Location restriction 511 can limit the location at which the user may be alerted by the operation controlled by operation controller 427. For instance, the user may indicate a preferred area on a map displayed on a user interface, such as screen 224, at which he wishes to be notified by an alert operation or not notified. Traffic restriction 512 can limit an amount of traffic during which the user may be alerted. Fatigue restriction 513 can limit the alert operation to a certain level of fatigue of the user. Audio restriction 514 can limit the alert operation to any property 471-479 of an audio signal outputted to the user. Time restriction 515 can limit the alert operation to a certain time, for instance to the evening when it is dark and/or to a time when the user is commuting between home and work. Vehicle restriction 516 can limit the alert operation to a certain property of a vehicle in a vicinity of the user, for instance a type of the vehicle and/or a speed of the vehicle and/or an angle restriction from which the vehicle may approach the user. For example, the alert operation may be limited to a type of a vehicle that may be hard to recognize by an emitted sound such as an EV and/or a type of a vehicle that may potentially inflict a larger harm to the user such as a car. Vehicle restriction 516 can also limit the alert operation to a type of vehicle driven by the user, for instance a bike, or when the user is walking and not driving a vehicle. Audibility restriction 517 can restrict the alert to situations in which the user has hearing difficulties, for instance due to a high noise level in the ambient environment, which may be determined by sound sensor 411. Visibility restriction 518 can restrict the alert to situations in which the user has visibility difficulties, for instance due to limited viewing range and/or a confusing road environment. Weather restriction 519 can restrict the alert to certain weather situations, for instance rain and/or smog and/or ice on the road. Further restrictions to another context are conceivable, for instance a behavior restriction restricting the alert to a certain behavior of the user and/or an alertness restriction restricting the alert to a certain alertness of the user.

Restrictions 511-519 can be inputted to condition customization module 502 in the form of customization data 504. Condition customization module 502 can then customize the condition such that the condition is unfulfilled in a case in which user-related data 421 and/or vehicle-related data 422 is indicative of a context beyond the restriction 511-519. The customized condition can then be applied by condition evaluation module 505 in the above described way.

Figure 20:
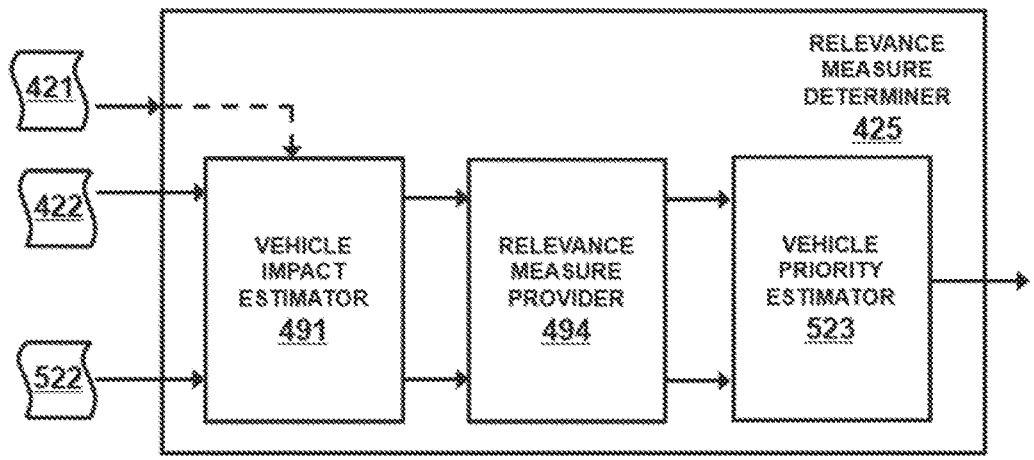
FIG. 20 schematically illustrates some exemplary configurations of the hearing device illustrated in FIGS. 2, 4 and/or the electronic device illustrated in FIG. 4 to determine a relevance measure indicative of a probability that the user is endangered by a vehicle.

FIG. 20 illustrates a functional block diagram of an exemplary implementation of relevance measure determining module 425. Relevance measure determining module 425 may be executed by processing unit 420 in the algorithm shown in FIG. 8 and/or in the algorithm shown in FIG. 17. Relevance measure determining module 425 comprises vehicle impact estimation module 491, relevance measure provision module 494, and a vehicle priority estimation module 523. Module 425 may further comprise user awareness estimation module 492. User-related data 421 may be inputted to vehicle impact estimation module 491 and/or user awareness estimation module 492. Module 425 may further comprise correlation module 493 and/or condition evaluation module 505.

Vehicle-related data 422 is inputted to vehicle impact estimation module 491. Vehicle-related data 422 is first vehicle-related data associated with a first vehicle in the vicinity of the user. Furthermore, second vehicle-related data 522 associated with a second vehicle in the vicinity of the user is inputted to vehicle impact estimation module 491. Vehicle impact estimation module 491 can thus determine a first probability that the first vehicle will impact the user and a second probability that the second vehicle will impact the user. The first vehicle impact probability and the second vehicle impact probability can then be inputted to relevance measure provision module 494. A user awareness probability estimated by user awareness estimation module 492 may be additionally inputted to relevance measure provision module 494. Relevance measure provision module 494 can provide a first relevance measure indicative of a probability that the user is endangered by the first vehicle, and a second relevance measure indicative of a probability that the user is endangered by the second vehicle. The first relevance measure and the second relevance measure can be inputted to vehicle priority estimation module 523. Vehicle priority estimation module 523 can determine a prioritization measure depending on the first relevance measure and the second relevance measure. The prioritization measure can be indicative of which of the first vehicle and the second vehicle shall be prioritized to control the operation alerting the user about the vehicle.

In some instances, the prioritization measure can be provided by module 523 by determining which of the first relevance measure and the second relevance measure is indicative of a higher probability, and selecting the vehicle represented by the relevance measure with the higher probability. In some instances, the prioritization measure can be provided by taking into account at least one additional criterion which may have been disregarded during determining the first relevance measure and/or the second relevance measure. The additional criterion may comprise, for instance, whether a property of first vehicle or a property of the second vehicle is able to cause a larger harm to the user.

The prioritization measure can be inputted to operation control module 427. Operation control module 427 can then control the operation alerting the user depending on the prioritization measure by selecting the operation from a first operation and a second operation, the first operation alerting the user about the first vehicle and the second operation alerting the user about the second vehicle. In particular, when the prioritization measure indicates that the first vehicle shall be prioritized the first operation can be selected, and when the prioritization measure indicates that the second vehicle shall be prioritized the second operation can be selected. Operation control module 427 can be further configured to control the operation alerting the user depending on the relevance measure associated with the vehicle that shall be prioritized. In particular, when the prioritization measure indicates that the first vehicle shall be prioritized, the operation may be controlled depending on the first relevance measure, and when the prioritization measure indicates that the second vehicle shall be prioritized, the operation may be controlled depending on the second relevance measure. This may imply that operation control module 427 refrains from controlling an operation alerting the user about the vehicle that has been prioritized by the prioritization measure when the relevance measure associated with the vehicle is below a threshold required for controlling the operation. In such a case, operation control module 427 may be configured to control the operation alerting the user about the other vehicle that has not been prioritized by the prioritization measure depending on the relevance measure associated with the other vehicle. This may also imply that operation selection module 483 of operation control module 427, as illustrated in FIG. 14, selects one of operations 485-487 depending on the relevance measure.

In some implementations, the prioritization measure can be provided by vehicle priority estimation module 523 depending on the relevance measures determined for more than two vehicles. In particular, additional vehicle-related data comprising at least third vehicle-related data associated with a third vehicle in the vicinity of the user can be inputted to vehicle impact estimation module 491 to provide a third probability that the third vehicle will impact the user, wherein an additional relevance measure comprising at least a third relevance measure indicative of a third probability that the user is endangered by the third vehicle can be provided by relevance measure provision module 494. Vehicle priority estimation module 523 can then determine a prioritization measure depending on each of the determined relevance measures. In some instances, the prioritization measure may then be provided as a list in which the vehicles are ordered by their priority. Operation control module 427 can be configured to control the operation depending on the priority of the vehicle and the relevance measure associated with the vehicle. In particular, operation control module 427 may first take into account the vehicle associated with the highest priority, and subsequently the vehicle associated with the next highest priority to control the operation depending on the respective relevance measure.

To illustrate, referring to FIG. 1, pedestrian 21 may be a user of hearing device 100. A relevance measure may be determined for each of the four vehicles 22-25 in the vicinity of user 21. The relevance measure associated with van 22 may be indicative of the highest probability to endanger user 21, for instance due to a proximity and/or a crossing of itineraries 31, 32 and/or a type of vehicle 22 potentially inflicting a high magnitude of harm to user 21. Other vehicles 23-25 may be estimated as less relevant, for instance vehicle 24 may be associated with the second highest probability, vehicle 23 with the third highest probability, and vehicle 25 with the lowest probability to endanger the user. User 21 is therefore primarily threatened by van 22 as compared to other vehicles 23-25 with the lower relevance. Alerting the user about all vehicles 22-25 and/or about any other vehicle 23-25 than van 22 may confuse the user and may even increase the danger of the traffic situation. Accordingly, van 22 can be prioritized by vehicle priority estimation module 523 in order to alert the user only about van 22. In this way, the user's interests of reliably becoming alerted about a potentially risky traffic situation and of not being overloaded or annoyed by too many or needless alerts can be balanced.

As illustrated in FIG. 20, vehicle priority estimation module 523 may be implemented in relevance measure determining module 425. In other configurations, vehicle priority estimation module 523 may be implemented in operation control module 427. In other configurations, vehicle priority estimation module 523 may be implemented as a separate module interposed between relevance measure determining module 425 and operation control module 427.

FIGS. 21A and 21B illustrate an exemplary traffic situation involving a user 532 of a hearing device 533, and a vehicle 537 in the form of a car approaching user 532 along a trajectory 538. Hearing device 533, which may be implemented as hearing device 100, is a binaural device comprising a first ear unit 534 and a second ear unit 535 worn on both ears of user 532. At a first time, as illustrated in FIG. 21A, user 532 faces away from the location and/or moving direction and/or itinerary 538 of vehicle 537. Therefore, the user may not be aware of potentially dangerous vehicle 537. At a second time, as illustrated in FIG. 21B, user 532 performs a rotation. A direction 536 of the rotation is indicated by a dashed arrow. As a result, an orientation of user 532 is directed toward the location and/or moving direction and/or itinerary 538 of vehicle 537. It can be assumed that the user is now aware of vehicle 537, since vehicle 537 may be in a visibility range of user 532 and/or user 532 may have performed rotation 536 to verify that vehicle 537 is approaching after perceiving a sound emitted by vehicle 537. The relevance measure can therefore be determined to be indicative of a reduced value of the probability that user 532 is endangered by vehicle 537 as compared to a situation in which user 532 does not perform rotation 536 and/or performs a different rotation and/or is oriented in a different direction. In some instances, a probability that user 532 is aware of vehicle 537 may be determined with an increased value due to a corresponding behavior of the user. The probability may be determined by user behavior classification module 497 based on user-related data 421 which may include rotation data and/or orientation data provided by movement sensor 414. In some instances, direction 536 and/or the orientation of user 532 relative to the location and/or moving direction and/or itinerary 538 of vehicle 537 is employed to provide a desired directivity 474 of the outputted audio signal as an operation alerting the user about the vehicle. Audio directivity 474 may be provided by an according spatialization of the audio signal, which may be performed by processing unit 420. The operation may be performed by operation control module 427 by taking into account direction 536 and/or the orientation of user 532 relative to the location and/or moving direction and/or itinerary 538 of vehicle 537.

FIGS. 22A and 22B illustrate another exemplary traffic situation involving user 532 of hearing device 100. At a first time, as illustrated in FIG. 22A, a direction 544 of an orientation of a head 541 of user 532 points substantially in parallel to a surface 542 of the earth, in particular in parallel to the ground below user 532. Direction 544 may be associated with a viewing direction of user 532. In the situation illustrated in FIG. 22A, user 532 looks straight ahead. At a second time, as illustrated in FIG. 22B, user 532 turned his head 541 toward surface 542 along direction 545. A direction 546 of the user's head orientation thus deviates from the direction 544 parallel to the earth's surface 542 by an angle 547. Viewing direction 546 points toward the earth's surface 542, i.e. user 532 looks down. The second behavior of user 532 illustrated in FIG. 22B can increase the user's risk during traffic as compared to the first behavior of user 532 illustrated in FIG. 22A. For instance, the user may look downwards while walking or driving, for instance when looking at a smartphone and/or having lost its thoughts and/or being fallen asleep. During the second behavior, the relevance measure can therefore be determined to be indicative of an increased value of the probability that user 532 is endangered by a vehicle as compared to during the first behavior. In some instances, a probability that user 532 is aware of a vehicle may be determined by user behavior classification module 497 with a decreased value due to a corresponding behavior of the user. In some instances, the user may restrict the alert operation to situations in which the user is not looking straightforward via condition customization module 502. The second behavior of the user can then be a condition evaluated by condition evaluation module 505, wherein the relevance measure is determined depending on whether the condition is fulfilled. The behavior may be determined based on user-related data 421 which may include rotation data and/or orientation data provided by movement sensor 414. For instance, movement sensor 414 may include an accelerometer configured to provide orientation data indicative of a direction of the user's head orientation relative to the gravitational force perpendicular to the earth's surface 542. The relevance measure may be determined to be indicative of an increased value when the user's viewing direction deviates from a direction parallel to the earth's surface 542 by more than a predefined value of angle 457. Such a predefined value may correspond, for instance, to at least 10 degrees.

Figure 23:
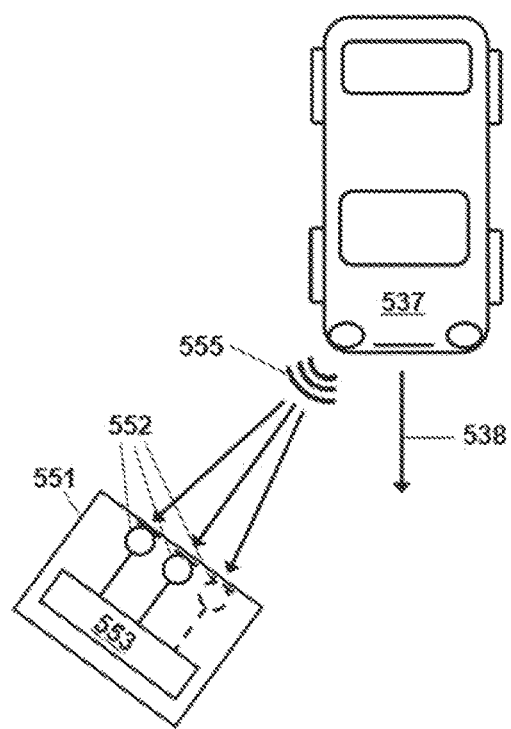
FIGS. 23-26 schematically illustrate further exemplary traffic situations during which vehicle-related data can be obtained by the hearing device illustrated in FIGS. 2, 4 and/or the electronic device illustrated in FIG. 4.

FIG. 23 illustrates another exemplary traffic situation involving vehicle 537 moving along trajectory 538 relative to a user wearing hearing device 100. A sound sensor 551 is provided stationary with the user, for instance in detector unit 100 of hearing device 100. For example, sound sensor 411 of detector unit 410 may be implemented by sound sensor 551. Sound sensor 551 comprises a plurality of spatially separated microphones 552. A sound 555 emitted by vehicle 537 can be detected by each microphone 552 at a different position. Spatially resolving the detected sound 555 can be employed to determine a dynamic property of vehicle 537, for instance a location and/or moving direction and/or speed and/or itinerary and/or distance and/or proximity and/or presence of vehicle 537. The detected sound may also be employed to determine an intrinsic property of vehicle 537, for instance a type of vehicle 537. Hearing device 100 can be provided as a binaural device comprising two ear units wearable at both ears of the user. Microphones 552 may then be spaced apart by integrating at least two microphones 552 in a different ear unit. This can result in a comparatively large spatial separation of microphones 552 which may be employed for an higher accuracy when determining the property depending on the spatialization. Sound data provided by each microphone 552 may be inputted to a processor 553 via a respective signal channel. Processor 553 may be included in processing unit 420. Processor 553 may also be implemented as a separate processing unit integrated in sound sensor 551. Processor 553 can be configured to determine differences in the sound data provided by different microphones 552 in order to assess a dynamic and/or intrinsic property of vehicle 537. For instance, the dynamic property may be determined based on a different time of arrival and/or a different sound level and/or a different phase and/or a different frequency and/or a different signal propagation delay of the sound detected by different microphones 553. In a binaural hearing device, the dynamic property may be determined based on an IPD and/or an ITD and/or an ILD of sound 555 detected at the different ear units. In some instances, a probability that that vehicle 537 will impact the user may be determined by vehicle impact estimation module 491 depending on vehicle property determined from sound 555 detected by microphones 552. In some instances, the user may restrict the alert operation to a certain vehicle property, for instance a type and/or speed of vehicle 537. The vehicle property determined from sound 555 can then be a condition evaluated by condition evaluation module 505, wherein the relevance measure is determined depending on whether the condition is fulfilled.

Figure 24:
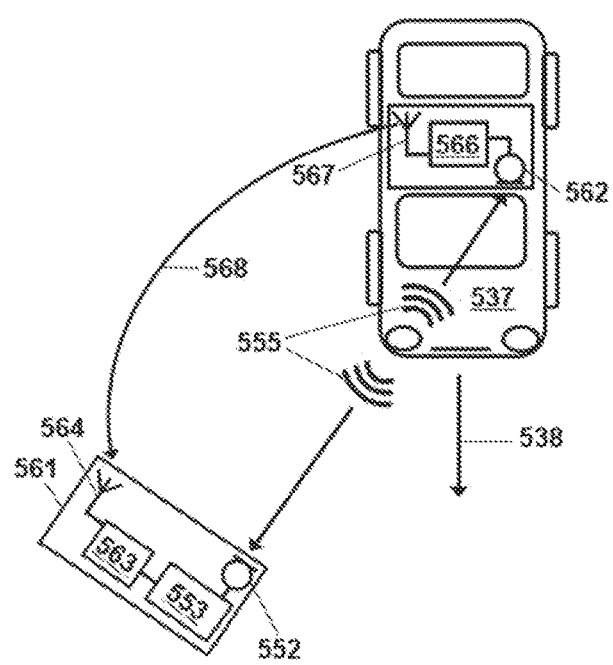

FIG. 24 illustrates another exemplary traffic situation involving vehicle 537 moving along trajectory 538 relative to a user wearing hearing device 100. A combined sound sensor and radio receiving unit 561 is provided stationary with the user, for instance in detector unit 100 of hearing device 100. For example, sound sensor 411 and radio sensor 412 of detector unit 410 may be implemented by unit 561. Unit 561 comprises at least one microphone 552 or a plurality of spatially separated microphones 552 as illustrated in FIG. 23, and an RF receiving port 564, which may be implemented by communication port 106 of hearing device 100. As illustrated, RF receiving port 564 can be included in a communication unit 563, which may be implemented as communication unit 105 of hearing device 100. Hearing device 100 may be provided as a binaural device comprising two ear units wearable at both ears of the user. Each of the ear units may then comprise an RF receiving port 564 allowing to spatially resolve the received RF signal. Moreover, a plurality of microphones 552 may be spaced apart by integrating at least two microphones 552 in a different ear unit, as detailed above in conjunction with FIG. 23. Sound data provided microphone 552 and radio data received by RF receiving port 564 may be inputted to processor 553 via a respective signal channel.

A combined sound sensor and radio emitter unit 566 is stationary included in vehicle 537. For instance, unit 566 may be mounted on a rooftop of vehicle 537. As illustrated, unit 566 comprises at least one microphone 562 and an RF emitting port 567. Sound 555 emitted by vehicle 537 can thus be simultaneously detected by unit 561 stationary with the user, and by unit 566 stationary with the vehicle. In addition, radio data representing the sound detected by unit 566 stationary with the vehicle can be transmitted to unit 561 stationary with the user via an RF signal 568. In particular, RF signal 568 can be emitted by RF emitting port 567 stationary with the vehicle, and received by RF receiving port 564 stationary with the user. For instance, RF signal 568 may be broadcast by unit 566 in a vicinity of the user and/or transmitted to RF receiving port 564 stationary with the user via a dedicated communication link. In some instances, unit 566 stationary with the vehicle comprises a plurality of spatially separated microphones 562 in order to obtain spatial information of the detected sound 555, which may also be transmitted via RF signal 568. For instance, RF signal 568 may contain sound data representative of sound 555 detected by each microphone 562.

Sound sensor and radio receiving unit 561 of hearing device 100 can thus be provided with information about sound 555 detected via microphone(s) 552 in the form of sound data obtained stationary with the user, and via RF receiving port 564 in the form of radio data containing information about sound obtained stationary with vehicle 537. In some instances, the information about the sound contained in the radio data can be compared with the sound data provided by microphone(s) 552 to obtain information about a property of vehicle 537. In particular, the information about the sound contained in the radio data can serve as a reference for the sound data provided by microphone(s) 552. To illustrate, when hearing device 100 is implemented as a binaural hearing device, a dynamic property of vehicle 537 may be determined based on an IPD and/or an ITD and/or an ILD of sound 555 detected by a respective microphone 552 at the different ear units, wherein the sound detected at each unit may be compared with the information about the sound data contained in the radio data. In some instances, a time of arrival of the radio data may be employed to obtain information about a property of vehicle 537. In particular, RF signal 568 may be spatially resolved by implementing a plurality of spaced apart RF receiving ports 564 in hearing device 100. Differences in RF signals 568 received at the different positions, for instance an RSSID and/or differences in the signal intensities, may then be employed to determine the dynamic property of vehicle 537. To illustrate, a respective RF receiving port 564 may be included in different ear units of a binaural hearing device allowing to exploit a comparatively large distance between the RF receiving ports 564 to spatially resolve the incoming signal.

In some instances, both the information about the sound contained in the radio data and a time of arrival of the radio data may be employed to obtain information about a property of vehicle 537. In particular, an IPD and/or an ITD and/or an ILD may be combined with an RSSID to increase the information content and thus the accuracy of the determined vehicle property. In some instances, the information about the vehicle may be solely obtained by the information contained in the radio data, in particular such that the sound data provided by microphone(s) 552 may not be employed. For example, a dynamic and/or intrinsic property of vehicle 537 may be obtained based on sound data provided by a plurality of spatially separated microphones 562 stationary with vehicle 537. The detected sound and/or the determined property of vehicle 537 may then be transmitted to hearing device 100 via RF signal 568. For instance, the radio data in RF signal 568 may include information based on a sound of a siren emitted by an emergency vehicle.

Figure 25:
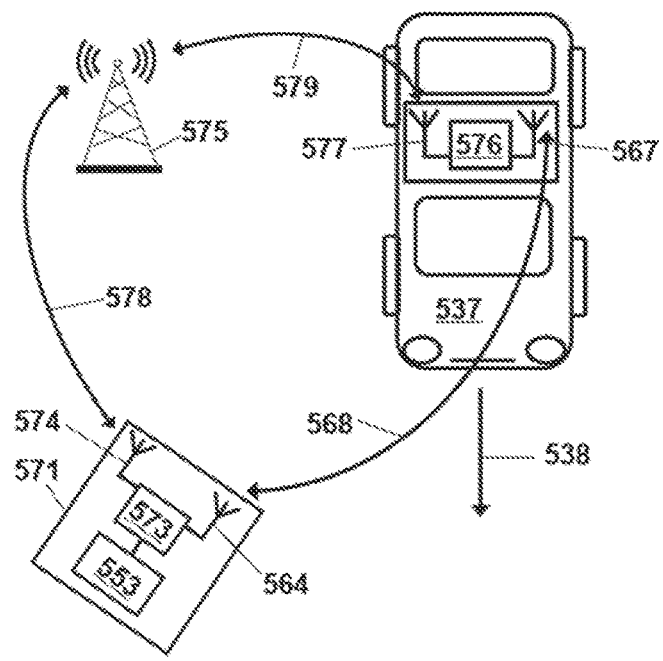

FIG. 25 illustrates another exemplary traffic situation involving vehicle 537 moving along trajectory 538 relative to a user wearing hearing device 100. An RF transceiving unit 571 is provided stationary with the user. Unit 571 comprises a communication unit 573 including first communication port 564, and a second communication port 574. Communication ports 564, 574 are each configured to emit and/or receive an RF signal. In some instances, communication unit 105 of hearing device 100 may be implemented by unit 571. In some instances, communication unit 205 of remote device 200 may be implemented by unit 571. Data received by communication unit 573 can be processed by a processor 553, which may be implemented by processing unit 420. An RF transceiving unit 576 is provided stationary with vehicle 576. Unit 571 comprises a communication unit 573 including first communication port 567 and a second communication port 577. Communication ports 567, 577 are each configured to emit and/or receive an RF signal.

In some instances, second communication port 574 stationary with the user is configured to receive an RF signal 578 from a communication network, for instance from a base transceiver station (BTS) 575 which may be communicatively connected to a central server and/or a cloud. RF signal 578 may comprise user-related data 421 and/or vehicle-related data 422, 522. In some instances, second communication port 576 stationary with the vehicle is configured to receive an RF signal 579 from the communication network. RF signal 579 may comprise vehicle-related data 422, 522. RF signal 579 may also comprise user-related data 421. First communication port 564 stationary with the user can then be configured to receive at least part of the data included in RF signal 579 and/or additional data from first communication port 567 stationary with the vehicle via an RF signal 568. RF signal 568 may be broadcast by unit 576 and/or transmitted to unit 571 via a dedicated communication link. For instance, an ad hoc communication, e.g. based on WLAN, may be employed between units 576, 571. In some instances, units 576, 571 can be configured to bi-directionally communicate directly via RF signal 568. In some instances, units 576, 571 can be configured to bi-directionally communicate via RF signals 578, 570 through the communication network. User-related data 421 and/or vehicle-related data 422, 522 may be exchanged by the bi-directional communication.

Figure 26:
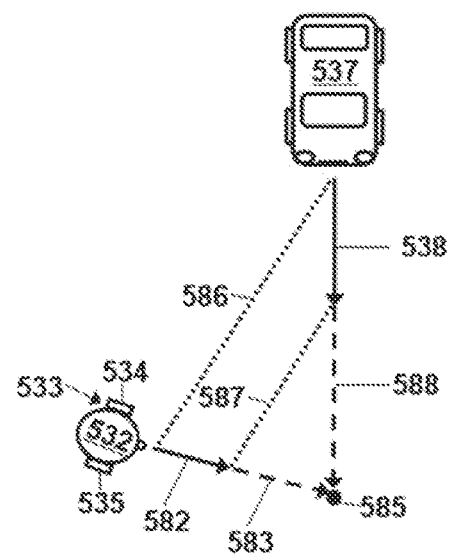

FIG. 26 illustrates another exemplary traffic situation involving vehicle 537 moving along trajectory 538 relative to user 532 wearing binaural hearing device 533 moving along a trajectory 582. Processing unit 420 can be configured to predict a probability that a future location of the vehicle will coincide with a future location of the user. The probability may be determined by vehicle impact estimation module 491. For instance, an impact location 585 may be determined based on user-related data 421 and/or vehicle-related data 422, 522. The impact location may be defined as a location at which a future location of the vehicle is likely to coincide with a future location of the user. Vehicle-related data 422, 522 may comprise information about trajectory 538, for instance information about a location of the vehicle and/or a speed of the vehicle and/or a moving direction of the vehicle and/or an itinerary of the vehicle. User-related data 421 may comprise information about trajectory 582, for instance information about a location of the user and/or a speed of the user and/or a moving direction of the user and/or an itinerary of the user. Vehicle-related data 422, 522 may also comprise information about a distance of the vehicle relative to the user.

In some implementations, as illustrated, impact location 585 is predicted based on the intercept theorem which may be applied on the information about trajectory 538 of the vehicle, and on the information about trajectory 582 of the user. To illustrate, the information about trajectory 582 of the user may comprise a velocity of the user having a starting point at the user's location, and the information about trajectory 538 of the vehicle may comprise a velocity of the vehicle having a starting point at the vehicle's location. As another example, the information about trajectory 582 of the user may comprise an itinerary traveled by the user within a period, and the information about trajectory 538 of the vehicle may comprise an itinerary traveled by the vehicle within the period. A first triangle may be defined by a first line 583 constituting a straight extension of user trajectory 582 leading to impact location 585, a second line 588 constituting a straight extension of vehicle trajectory 538 leading to impact location 585, and a third line 587 constituting a straight interconnection between starting points of extension lines 583, 588 corresponding to end points of trajectories 538, 582. A second triangle may be defined by a first line including user trajectory 582 combined with straight extension line 583, a second line including vehicle trajectory 538 combined with straight extension line 588, and a third line 586 constituting a straight interconnection between the starting points of trajectories 538, 582. The first triangle and the second triangle may be similar if and only if (iff) interconnection lines 586, 587 are substantially parallel. Only then the intercept theorem can be applicable according to which a ratio between the line including user trajectory 582 combined with its straight extension line 583 and the straight extension line 583 corresponds to a ratio between the line including vehicle trajectory 538 combined with its extension line 588 and the extension line 588, and also corresponds to a ratio between interconnection lines 586, 587. The probability that a future location of the vehicle will coincide with a future location of the user, in particular the impact probability of the vehicle with the user, can then be determined depending on a degree by which interconnection lines 586, 587 are parallel. In this regard, a linear dependency between trajectories 538, 582 may be assumed, which may imply to approximate trajectories 538, 582 in terms of a non-accelerated motion of the vehicle and the user. For instance, an angle spanned by interconnection lines 586, 587 may be determined by vehicle impact estimation module 491, wherein the impact probability of the vehicle with the user is determined to have a non-negligible value when the angle has a value between zero degrees and an upper threshold value.

Figures 27, 28:
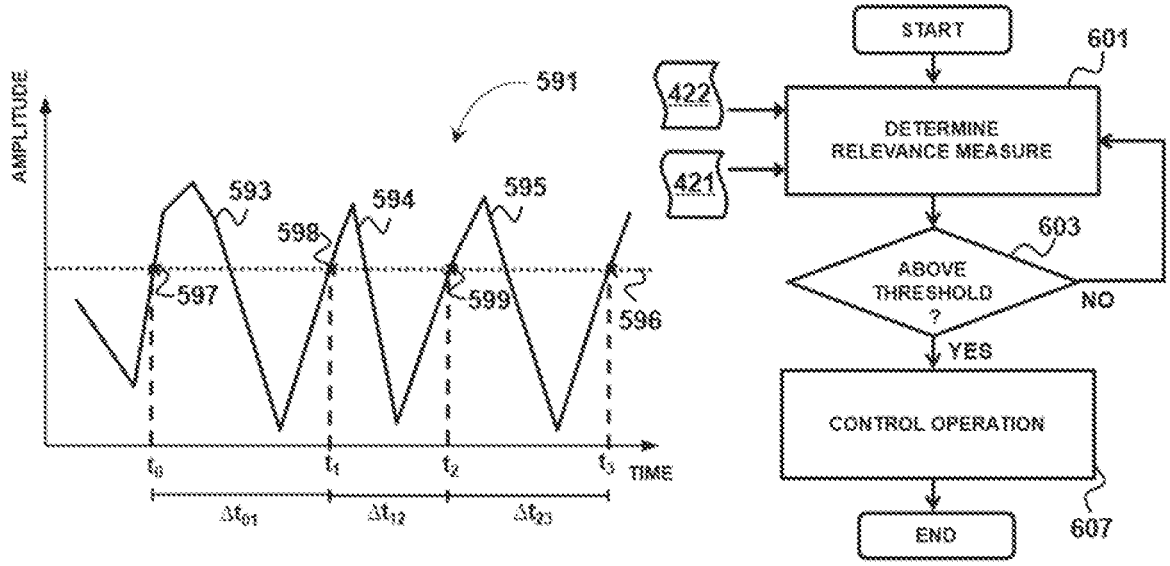
FIG. 27 schematically illustrates a graph of user-related data including information about a walking activity of the user which may be detected by a movement sensor included in the hearing device illustrated in FIGS. 2, 4 and/or the electronic device illustrated in FIG. 4.
FIGS. 28-35 illustrate exemplary methods of operating a hearing device and/or a hearing system according to principles described herein.

FIG. 27 illustrates an exemplary graph 591 of movement data that may be provided by movement sensor 414 as user-related data 421 while the user of hearing device 100 is taking steps. The illustrated movement data can be, for instance, a y-axis component of data output by an accelerometer. As shown, the amplitude characteristic of the movement data fluctuates with a certain regularity over time. Subsequent pulses 593, 594, 595 of the movement data are produced by a respective step taken by the user. Each pulse 593-595 comprises an associated data range 597, 598, 599 at which the movement data crosses an amplitude threshold 596 from below the threshold to above the threshold. The threshold crossing points 597-599 constitute movement features representative of a walking activity of the user that can be identified by relevance measure determination module 425 as a pattern of the walking activity. Based on the pattern, the movement data provided by movement sensor 414 can be classified as walking data representative of a walking activity of the user.

Threshold crossing points 597-599 of consecutive pulses 593-595 are separated by a respective time interval. The time intervals can serve as a temporal characteristic of the sequence of movement features 597-599. Moreover, threshold crossing points 597-599 reoccur in the sequence over time within a certain cadence range. The cadence range may be defined by a lower limit (e.g., a particular cadence, such as 0.5 Hz) and an upper limit (e.g., a particular cadence, such as 9 Hz). The cadence range can serve as another temporal characteristic of the sequence of movement features 597-599. The temporal characteristic can be determined by relevance measure determination module 425, for instance by user behavior classification module 497 and/or condition evaluation module 505. Moreover, a peak amplitude of subsequent pulses 593-595 may be determined as another characteristic of the sequence of movement features 597-599. This can allow a further identification of the pattern of the movement data associated with a walking activity of the user. A corresponding pattern may be identified in the movement data when the user is performing another repetitive movement activity, which may comprise cycling data indicative of a cycling activity of the user and/or skating data indicative of a skating activity of the user and/or scooter data indicative of an activity of the user riding a scooter.

In some implementations, determining the pattern in the movement data can be employed to restrict the alarm operation controlled by operation control module 427 to a certain type of locomotion of the user, for instance walking and/or cycling. For instance, the user may indicate via a user interface to condition customization module 502 that he wants to restrict the alarm operation to such a locomotion type. A condition depending on which the relevance measure is determined can then be customized by condition customization module 502 such that the condition is determined to be fulfilled by condition evaluation module 505 when user-related data 421 including the movement data contains the pattern of the locomotion type, for instance walking data indicative of a walking pattern and/or cycling data indicative of a cycling pattern.

In some implementations, determining the pattern in the movement data and/or changes in the pattern in the movement data can be employed to determine a user behavior by user behavior classification module 497 depending in which the relevance measure can be determined. The changes in the pattern in the movement data may comprise, for instance, a temporal characteristic and/or an amplitude characteristic of the sequence of movement features 597-599. To illustrate, the user may change his walking behavior after detecting a potentially dangerous vehicle, for instance by slowing down and/or hurrying up. The changes in the pattern of the walking data, in particular when they coincide with a vehicle appearing in the vicinity of the user, can thus indicate that the user is aware of the vehicle. The relevance measure may then be determined to be indicative of a lower probability that the user is endangered by the vehicle. In the contrary case, when the user maintains its current walking behavior, it may be assumed that the user is not aware of the vehicle. The relevance measure may then be determined to be indicative of a higher probability that the user is endangered by the vehicle.

FIG. 28 illustrates a block flow diagram for an exemplary method of providing an alert for a user by a hearing device configured to be worn at an ear of the user. The method may be executed by processing unit 420, in particular by executing the data processing algorithm illustrated in FIG. 8 or FIG. 17. At 601, a relevance measure indicative of a probability that the user is endangered by a vehicle in a vicinity of the user is determined based on user-related data 421 and vehicle-related data 422. The relevance measure is indicative of a probability that the user is endangered by the vehicle. Determining the relevance measure based on user-related data 421 and vehicle-related data 422 can allow to put the vehicle in a context with the user. The relevance measure may be determined as a numeric value. The value, for instance a value between zero and one, may be representative for a percentage. The value representing zero percent can indicate that the probability that the user is endangered by the vehicle is estimated as being negligible. The value representing one hundred percent can indicate that the probability that the user is endangered by the vehicle is estimated as being certain. At 603, it is determined whether the relevance measure is above a threshold. Evaluating the relevance measure relative to the threshold may be performed by operation control module 427. To illustrate, the threshold may be specified as a value representing fifty percent. When the relevance measure is determined to be above the threshold, an operation of the hearing device alerting the user about the vehicle is controlled at 607. When the relevance measure is determined to not exceed the threshold, operation 601 is repeated by determining the relevance measure. To this end, updated user-related data 421 and/or updated vehicle-related data 422 may be provided to relevance measure determining module 625 based on which an updated relevance measure is determined.

The relevance measure can thus be continuously determined by taking into account current changes in the user-related data 421 and/or vehicle-related data 422. This can allow to adapt the relevance measure to ongoing changes relevant for the danger posed to the user. To illustrate, the relevance measure may be adapted over time when a vehicle approaches the user, wherein the closer the vehicle to the user, the higher the probability may be determined that the user is endangered by the vehicle. As another example, a vehicle may stop moving or turn into another street away from the user, wherein the probability that the user is endangered by the vehicle may then be determined to a lower value than before. As a further example, the relevance measure may be adapted over time when the user changes its behavior indicating that the user became aware of the vehicle.

Figure 29:
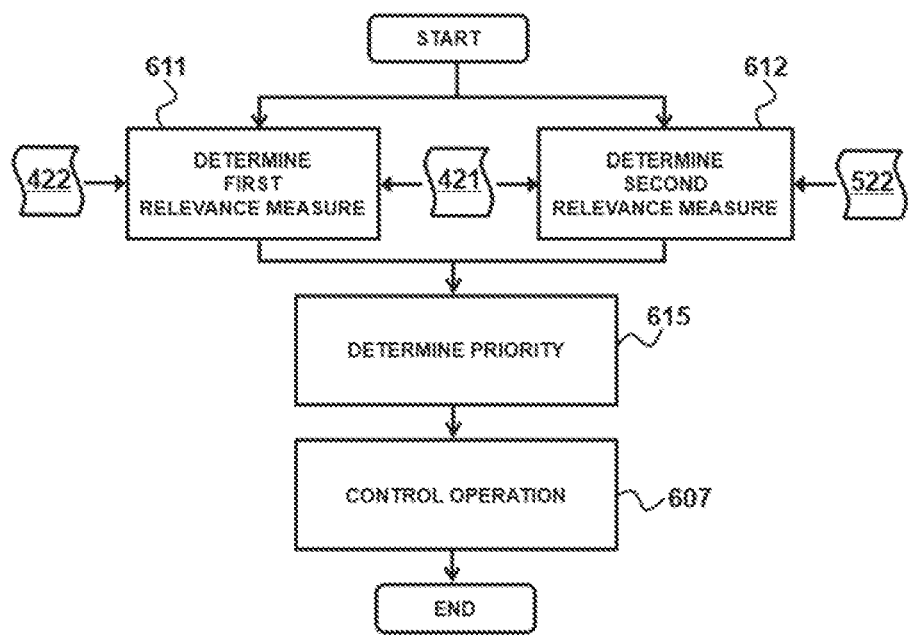

FIG. 29 illustrates a block flow diagram for another exemplary method of providing an alert for a user by a hearing device configured to be worn at an ear of the user. The method may be executed by processing unit 420, in particular by implementing relevance measure determining module 425 illustrated in FIG. 20 when executing the data processing algorithm illustrated in FIG. 8 or FIG. 17. At 611, a first relevance measure indicative of a probability that the user is endangered by a first vehicle in a vicinity of the user is determined based on user-related data 421 and first vehicle-related data 422. At 612, a second relevance measure indicative of a probability that the user is endangered by a second vehicle in a vicinity of the user is determined based on user-related data 421 and second vehicle-related data 522. At 615, it is determined whether the first vehicle or the second vehicle shall be prioritized when the user is alerted about one of the vehicles in the operation controlled by operation control module 427. For this purpose, a prioritization measure may be determined depending on the first relevance measure and the second relevance measure, in particular by vehicle priority estimation module 523. At 607, the operation is controlled depending on the prioritization measure and on the relevance measure which has been determined at 611 or 612 based on vehicle-related data 422, 522 of the vehicle that has been prioritized in the prioritization measure determined at 615.

Figure 30:
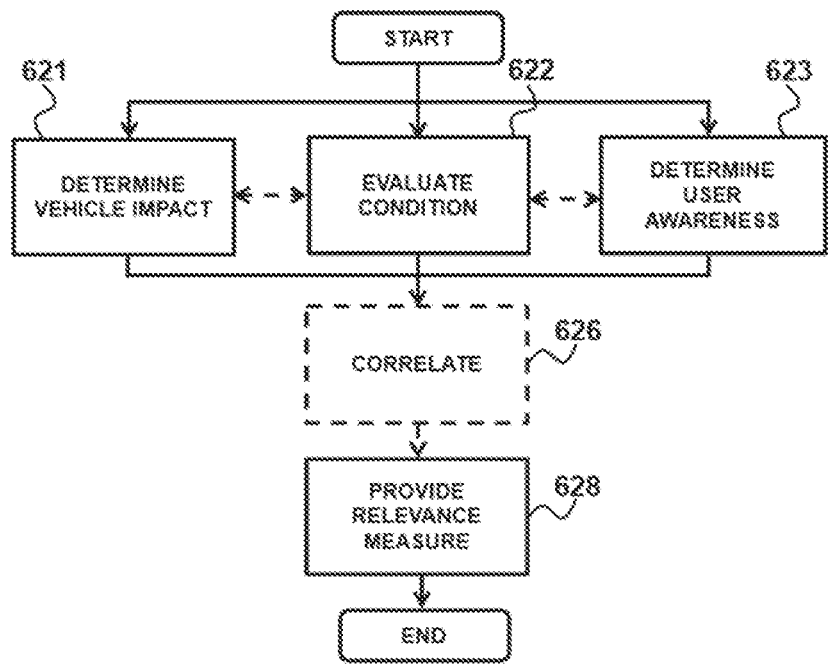

FIG. 30 illustrates a block flow diagram for an exemplary method of determining a relevance measure. The method may be executed by processing unit 420, in particular when executing the data processing algorithm illustrated in FIG. 18. The method may be applied at operation 601 of the method illustrated in FIG. 28 and/or at any of operations 611, 612 of the method illustrated in FIG. 29. At 621, a probability is determined that a vehicle in a vicinity of the user will impact the user. At 623, a probability is determined that the user is aware of a vehicle in its vicinity. Determining the relevance measure based on the vehicle impact probability determined at 621 and the user awareness probability determined at 623 can allow to put a danger contribution governed by the vehicle and a danger contribution governed by the user in a mutual context. At 622, it is determined whether user-related data 421 and/or vehicle-related data 422, 522 and/or the vehicle impact probability determined at 621 and/or the user awareness probability determined at 623 fulfills a condition customizable during operating the hearing device. Determining the relevance measure depending on the customizable condition can allow to restrict a context in which the operation alerting the user about the vehicle is controlled.

As illustrated, an outcome of the determining whether the condition is fulfilled at operation 622 may be inputted to operation 621 and/or operation 623. In this way, the vehicle impact probability may be only determined at 621 and/or the user awareness probability may be only determined at 623 depending on the condition determined to be fulfilled at 622. In particular, when the condition is determined to be not fulfilled at 622, the relevance measure may be only determined depending on this outcome of operation 622 independent from the vehicle impact probability and/or the user awareness probability. This may result in the alert operation not being controlled at operation 607 of the method illustrated in FIG. 28 and FIG. 29 due to the condition not being fulfilled.

At 626, the vehicle impact probability determined at 621 and the user awareness probability determined at 623 and/or the outcome whether the condition is fulfilled may be correlated. This can be employed to verify the mutual context between the vehicle impact probability and the user awareness probability and/or the outcome whether the condition is fulfilled. To illustrate, a certain movement behavior of the user may be only put in a context with a certain vehicle when there is a spatial correlation between the user's movement and/or position and/or orientation relative to a dynamic property of the vehicle. In this way, a false alert and/or an omission of a required alert controlled at operation 607 of the method illustrated in FIG. 28 and FIG. 29 may be avoided. At 628, the relevance measure is provided to be employed in subsequent operation 607 and/or 615.

Figure 31:
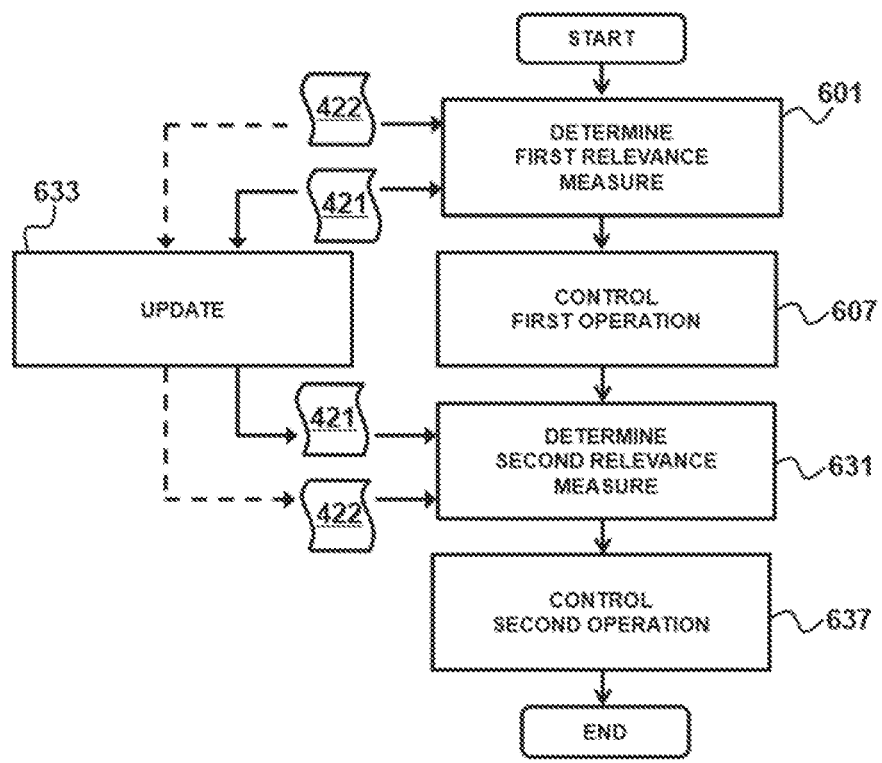

FIG. 31 illustrates a block flow diagram for another exemplary method of providing an alert for a user by a hearing device configured to be worn at an ear of the user. The relevance measure determined at 601 is a first relevance measure determined at a first time, and the operation controlled at 607 is a first operation alerting the user for a first time. In the mean time and/or after controlling the first operation at 607, user-related data 421 is updated at 633 such that it includes updated information. The updated information may differ from the previous information included in user-related data 421 provided at 601 in that the updated information has been obtained at a different time, for instance at a later time and/or a current time. The updated information may also differ from the previous information in that it represents a different property of the user and/or of the ambient environment and/or the hearing device and/or remote device operated by the user. At 631, a second relevance measure is determined at a second time, which is a time after the first time, based on the user-related data 421 updated at 633 and vehicle-related data 422, 522. In some instances, vehicle-related data 422, 522 may also be updated at 633 in order to include updated information. In some instances, vehicle-related data 422, 522 provided at 631 can correspond to vehicle-related data 422, 522 provided at 601. At 637, a second operation is controlled depending on the second relevance measure determined at 631. In some instances, the second operation can correspond to the first operation controlled at 607. In some instances, the second operation can differ from the first operation controlled at 607. For instance, the second operation may be selected to evoke a higher degree of alertness of the user as compared to the first operation.

In some implementations, when user-related data 421 is updated at 633 after controlling the first operation at 607, the updated information can be indicative of a reaction of the user to the operation controlled at 607. For instance, a movement behavior and/or a change of a movement behavior of the user, which may be determined by user behavior classification module 479, can indicate such a reaction. To illustrate, in a first case in which the user walks slower and/or changes his head orientation into a straightforward direction and/or toward the vehicle, it may be assumed that the user became aware of the vehicle by the operation controlled at 607. In a second case in which the user's behavior doesn't change, it may be assumed that the user ignored and/or didn't note the alert provided by the operation controlled at 607. In the first case, the second operation may be controlled at 637 to be omitted such that no further alert for the user is provided. In the second case, the second operation may be controlled at 637 such that another alert for the user is provided, in particular an alert configured to evoke a higher degree of alertness of the user.

Figure 32:
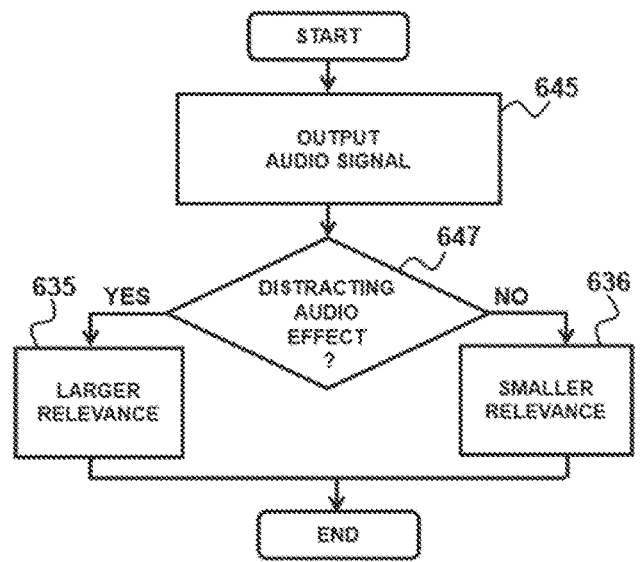

FIG. 32 illustrates a block flow diagram for another exemplary method of determining a relevance measure. The method may be executed by processing unit 420, in particular when executing the data processing algorithm illustrated in FIG. 15 or FIG. 18. The method may be applied at operation 601 of the method illustrated in FIG. 28 and/or at any of operations 611, 612 of the method illustrated in FIG. 29 and/or at any of operations 601, 631 of the method illustrated in FIG. 31. At 645, an audio signal is outputted to the user by an audio transducer included in the hearing device. A property 471-479 of the outputted audio signal may then be provided as user-related data 421 to determine the relevance measure. A probability that the user is aware of a vehicle in its vicinity, for which vehicle-related data 422, 522 can be provided in addition to the user-related data 421, may then be determined based on the user-related data 421, in particular by user awareness estimation module 492. To this end, audio signal classifier 495 may be employed. At 647, it is determined whether the outputted audio signal can be attributed to an audio signal suitable to decrease the user's awareness about the vehicle and/or an audio signal suitable to increase the user's awareness about the vehicle, for instance as compared to a situation in which no audio signal is outputted to the user. In particular, it may be determined whether a property 471-479 of the outputted audio signal is likely to distract the user from noticing the vehicle in its vicinity or to enhance the user's awareness about the vehicle.

In case the audio signal is suitable to decrease the user's awareness about the vehicle, a probability that the user is aware of the vehicle can be determined at a decreased value at 635 which may contribute to a larger probability that user is endangered by the vehicle, as indicated by the relevance measure. In case the audio signal is not suitable to decrease the user's awareness, in particular when the audio signal is suitable to increase the user's awareness about the vehicle, a probability that the user is aware of the vehicle can be determined at an increased value at 636 contributing to a smaller probability that user is endangered by the vehicle when determining the relevance measure. To illustrate, an audio signal received by the hearing device from an external audio source distant from the user, such as a phone call and/or a content from a media streaming source, may rather distract the user from the vehicle when outputted by the audio transducer. An audio signal representing a sound emitted from the vehicle, such as a sound detected in the ambient environment, may rather increase the user's awareness about the vehicle when outputted by the audio transducer.

Figure 33:
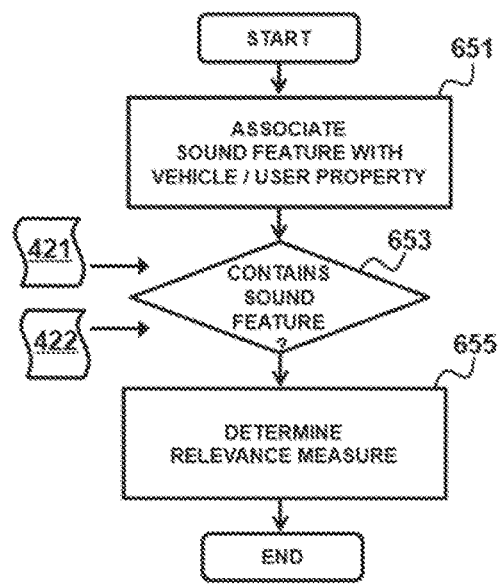

FIG. 33 illustrates a block flow diagram for another exemplary method of determining a relevance measure. The method may be executed by processing unit 420, in particular when executing the data processing algorithm illustrated in FIG. 15 or FIG. 18. The method may be applied at operation 601 of the method illustrated in FIG. 28 and/or at any of operations 611, 612 of the method illustrated in FIG. 29 and/or at any of operations 601, 631 of the method illustrated in FIG. 31. At 651, at least one sound feature is associated with at least one property of a vehicle and/or at least one property of the user and/or at least one property of the ambient environment of the user. In particular, the property may be an intrinsic property of the vehicle such as a typical sound emitted by a certain type of the vehicle, for instance a sound of a siren emitted by an emergency vehicle and/or a motor sound emitted by a car and/or a switching noise emitted by an EV and/or HV. The property may also be a dynamic property of the vehicle such as a motor sound at a certain volume level indicating a proximity and/or distance of the vehicle relative to the user and/or a moving direction and/or a speed of the vehicle. In some implementations, a plurality of different sound features are associated with different properties of a vehicle, for instance a different type of the vehicle. This can be employed to distinguish between the different vehicle properties based on the sound features. The sound feature may also be associated with a property of the user, for instance a certain behavior of the user such as a voice of the user when the user is talking and/or sounds of footsteps when the user is walking. The sound feature may also be associated with a property of the ambient environment of the user, for instance a certain noise typically emitted during intense traffic and/or a sound emitted by a traffic light for visually impaired people. In some implementations, a plurality of different sound features are associated with at least one property of a vehicle and at least one property of the user and/or an ambient environment of the user.

At 653, user-related data 421 and/or vehicle-related data 422, 522 is provided to determine the relevance measure. User-related data 421 and/or vehicle-related data 422, 522 may be inputted to relevance measure determining module 425. User-related data 421 and/or vehicle-related data 422, 522 comprises sound data indicative of a sound detected in the ambient environment of the user. For instance, the sound data may be provided by sound sensor 411. Furthermore, at 653, it is determined whether the user-related data 421 and/or vehicle-related data 422, 522 contains at least one sound feature associated with the at least one property of a vehicle and/or at least one property of the user and/or at least one property of the ambient environment at 651. In particular, the sound feature may be extracted and/or separated from the sound data indicative of the sound detected in the ambient environment. To this end, relevance measure determining module 425 can be configured to apply a digital signal processing (DSP) and/or an ML algorithm on the sound data. In particular, an ML algorithm based on a plurality of NNs may be employed. The different NNs may each be specialized to output a different sound feature in a case that the sound feature is contained in the sound data or a blank signal in a case that the sound feature is not contained in the sound data. For instance, an architecture of NNs as disclosed in international patent application No. PCT/EP2020/051734 and/or No. PCT/EP2020/051735 and/or No. PCT/EP2020/060196 may be applied.

At 655, when the sound feature is found to be present in user-related data 421 and/or vehicle-related data 422, 522, the relevance measure is determined. In some instances, the relevance measure can be determined to be indicative of an increased value of the probability that the user is endangered by the vehicle when the sound data contains the sound feature. For instance, the sound feature may be associated with a vehicle of a type potentially posing a high danger to the user. To illustrate, an EV or HV may be hard to recognize by its naturally emitted sound and therefore increase the risk for the user. The sound feature may also be associated with a behavior of the user increasing its risk. For instance, the user talking during travelling can indicate that he is not focused on the current traffic situation. In some instances, the relevance measure can be determined to be indicative of a decreased value of the probability that the user is endangered by the vehicle when the sound data contains the sound feature. For instance, the sound feature may be associated with a sound indicating a green traffic light to visually impaired people. In a contrary case, when the sound feature is not found to be present in user-related data 421 and/or vehicle-related data 422, 522, the relevance measure may be determined at 655 without taking into account a possible impact on the user's risk attributed to a presence of the sound feature.

Figure 34:
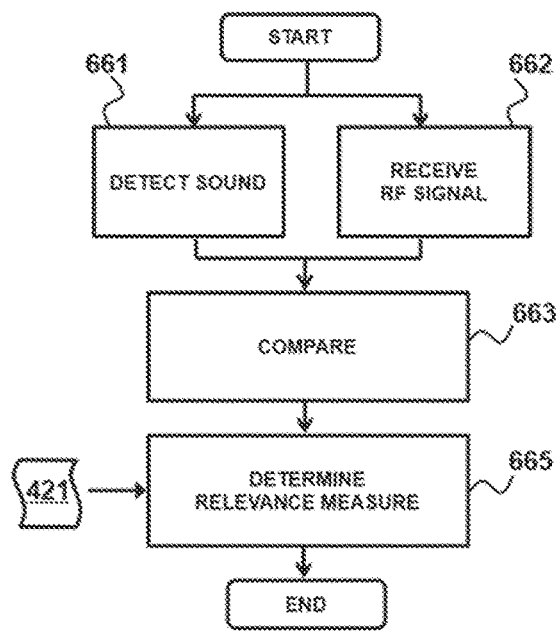

FIG. 34 illustrates a block flow diagram for an exemplary method of providing vehicle-related data 422, 522 and of determining a relevance measure based on the vehicle-related data 422, 522 and user-related data 421. The method may be executed by processing unit 420, in particular when executing the data processing algorithm illustrated in FIG. 15 or FIG. 18. The method may be applied at operation 601 of the method illustrated in FIG. 28 and/or at any of operations 611, 612 of the method illustrated in FIG. 29 and/or at any of operations 601, 631 of the method illustrated in FIG. 31. For instance, the method may be employed in a traffic situation as illustrated in FIG. 24. In some implementations, a hearing device and/or a remote device stationary with the user may then be equipped with sound sensor and radio receiving unit 561. At 661, a sound is detected in an ambient environment of the user. The sound may be detected by sound sensor 441. The detected sound may comprise information about sound 555 emitted from a vehicle. Simultaneously, at 662, an RF signal can be received. RF signal is emitted by the vehicle. The RF signal comprises information about sound 555 detected stationary with the vehicle. For instance, sound 555 may be detected by at least one microphone included in the vehicle, and the sound data provided by the microphone may then be included in the RF signal. Vehicle-related data 422 thus comprises the sound data, as detected stationary with the user at 661, and the RF signal containing information about sound 555 obtained stationary with the vehicle, as received at 662.

At 663, the information about sound 555 included in the RF signal is compared with the sound data detected stationary with the user. For instance, when the hearing device is a binaural device, sound 555 may be detected at different ear units of the hearing device at 661. An IPD and/or an ITD and/or an ILD of sound 555 detected at the different ear units may then be determined. The information about sound 555 contained in the RF signal may be employed as a reference to which sound 555 detected at each ear unit can be compared. Additionally or alternatively, an RSSID and/or differences in the signal intensities of the RF signal received at the different ear units can be determined at 663 by comparing the RF signals with each other. Based on the comparison at 663, a property of the vehicle can be determined, in particular a dynamic property. At 665, the determined property of the vehicle is employed to determine the relevance measure, in addition to further provided user-related data 421.

Figure 35:
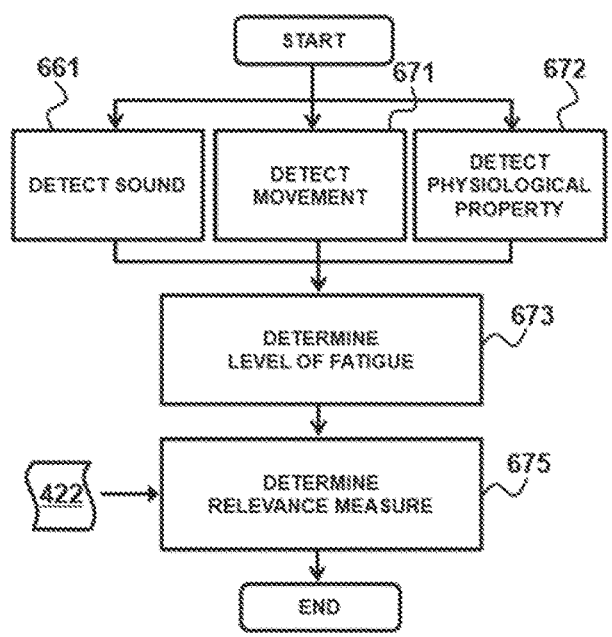

FIG. 35 illustrates a block flow diagram for an exemplary method of providing user-related data 421 and of determining a relevance measure based on the user-related data 421 and vehicle-related data 422, 522. The method may be executed by processing unit 420, in particular when executing the data processing algorithm illustrated in FIG. 15 or FIG. 18. The method may be applied at operation 601 of the method illustrated in FIG. 28 and/or at any of operations 611, 612 of the method illustrated in FIG. 29 and/or at any of operations 601, 631 of the method illustrated in FIG. 31. The user-related data 421 may be provided by performing at least one of operations 661, 671, and 672. The sound detected at 661 may include sound detected in the ambient environment of the user, for instance by a microphone, and/or sound detected on the user's body, for instance by a microphone and/or a VAD. At 671, a movement of the user is detected, for instance by movement sensor 414. At 672, a physiological property of the user is detected, for instance by physiological sensor 415. User-related data 421 comprising the sound detected at 661 and/or the movement detected at 671 and/or the physiological property detected at 672 can then be employed to determine a level of fatigue of the user at 674. In particular, the level of fatigue may be determined by user condition classification module 498. For example, a voice of the user represented by the sound detected at 661 and/or continuously performed movements detected at 671 and/or a biometric property detected at 672 by a biometric sensor may be employed to provide an estimation of the user's fatigue. The level of fatigue can be indicative of an awareness of the user about a potentially dangerous vehicle in the user's vicinity. At 675, the determined level of fatigue is employed to determine the relevance measure, in addition to further provided vehicle-related data 422, 522.

While the principles of the disclosure have been described above in connection with specific devices, systems, and methods, it is to be clearly understood that this description is made only by way of example and not as limitation on the scope of the invention. The above described embodiments are intended to illustrate the principles of the invention, but not to limit the scope of the invention. Various other embodiments and modifications to those preferred embodiments may be made by those skilled in the art without departing from the scope of the present invention that is solely defined by the claims. In the claims, the word "comprising" does not exclude other elements or steps, and the indefinite article "a" or "an" does not exclude a plurality. A single processor or controller or other unit may fulfil the functions of several items recited in the claims. The mere fact that certain measures are recited in mutually different dependent claims does not indicate that a combination of these measures cannot be used to advantage. Any reference signs in the claims should not be construed as limiting the scope.

What is claimed is:

1. A method of providing an alert for a user by a hearing device configured to be worn at an ear of the user, the method comprising:
   providing user-related data including information about at least one of the user, an ambient environment of the user, or a property of the hearing device worn by the user;
   providing first vehicle-related data associated with a first vehicle in a vicinity of the user, the first vehicle-related data including information about a property of the first vehicle;
   providing second vehicle-related data associated with a second vehicle in the vicinity of the user, the second vehicle-related data including information about a property of the second vehicle;
   determining, based on the user-related data and the first vehicle-related data, a first relevance measure indicative of a probability that the user is endangered by the first vehicle;
   determining, based on the user-related data and the second vehicle-related data, a second relevance measure indicative of a probability that the user is endangered by the second vehicle;
   determining, based on the first relevance measure and the second relevance measure, a prioritization measure indicating which of the first vehicle and the second vehicle is prioritized for providing alerts to the user, the prioritization measure based on one or more intrinsic properties of a vehicle including at least one of a type of the vehicle or a magnitude of harm associated with a mass of the vehicle; and
   controlling an operation of the hearing device depending on the prioritization measure, the operation alerting the user about at least one of the first vehicle or the second vehicle.

2. The method according to claim 1, wherein the user-related data comprises at least one of:
   data indicative of a property detected at least one of on the user or in an ambient environment of the user by a detector included in the hearing device;
   data indicative of a property of an audio signal outputted to the user by an audio transducer included in the hearing device; or
   data indicative of an effective size of a venting channel included in the hearing device, the venting channel configured to provide for venting between an inner region of an ear canal of the ear and an ambient environment outside the ear canal depending on the effective size.

3. The method according to claim 1, further comprising determining whether at least one of the user-related data or the first vehicle-related data fulfills a condition, wherein the first relevance measure is determined depending on the condition being fulfilled, wherein the condition is customizable during operating of at least one of the hearing device or an electronic device configured to be communicatively coupled to the hearing device.

4. The method according to claim 3, wherein the condition is customizable by at least one of:
   data provided via a user interface; or
   data communicated from a data source distant from the user.

5. The method according to claim 1, wherein the operation comprises at least one of:
   modifying, before an audio signal is outputted to the user by an audio transducer included in the hearing device, a property of the outputted audio signal;
   adjusting an effective size of a venting channel included in the hearing device, the venting channel configured to provide for venting between an inner region of an ear canal of the ear and an ambient environment outside the ear canal depending on the effective size;
   initiate outputting an audio signal to the user by an audio transducer included in the hearing device; or
   initiate a vibration of the hearing device evoking a tactile perception by the user.

6. The method according to claim 1, wherein:
   the hearing device is configured to receive an audio signal communicated from an external audio source; and
   when the audio signal is outputted to the user by an audio transducer included in the hearing device, the operation comprises at least one of:
   reducing a volume level of the outputted audio signal;
   outputting an audio signal representative of a sound detected in an ambient environment of the user;
   outputting a warning notification to the user; or
   terminating outputting the audio signal to the user.

7. The method according to claim 1, wherein the operation comprises at least one of:
   modifying, before an audio signal is outputted to the user by an audio transducer included in the hearing device, a directivity of the outputted audio signal such that the directivity points toward at least one of a location of the first vehicle, a moving direction of the first vehicle, or an itinerary of the first vehicle;
   modifying, before an audio signal is outputted to the user by an audio transducer included in the hearing device, at least one of a volume level of the outputted audio signal or a volume level of a sound feature contained in the outputted audio signal, the sound feature representing a sound emitted by the first vehicle in the vicinity of the user, depending on at least one of a distance of the first vehicle to the user, a type of the first vehicle, a speed of the first vehicle, or a direction from which the first vehicle is approaching the user;
   modifying, before an audio signal is outputted to the user by an audio transducer included in the hearing device, a frequency of a sound feature contained in the outputted audio signal, the sound feature representing a sound emitted by the first vehicle in the vicinity of the user;

attenuating, before an audio signal is outputted to the user by an audio transducer included in the hearing device, a volume level of a first sound feature contained in the audio signal relative to a volume level of a second sound feature contained in the audio signal, the second sound feature representing a sound emitted by the first vehicle in the vicinity of the user; or superimposing, before an audio signal containing a first sound feature is outputted to the user by an audio transducer included in the hearing device, a second sound feature to the audio signal, the second sound feature suitable to attract the user's attention away from the first sound feature when perceiving the outputted audio signal.

8. The method according to claim 1, wherein the operation is a first operation, the method further comprising:

controlling a second operation of the hearing device depending on the first relevance measure, the second operation alerting the user about the first vehicle, wherein the first operation is selected to be controlled when the first relevance measure is determined to have a first value, and the second operation is selected to be controlled when the first relevance measure is determined to have a second value, wherein the first value is indicative of a smaller probability that the user is endangered by the first vehicle than the second value.

9. The method according to claim 1, wherein the user-related data comprises at least one of movement data indicative of a movement of the user, physiological data indicative of a physiological property of the user, or sound data indicative of a detected sound, the method further comprising determining a probability that the user is aware of the first vehicle based on the user-related data, wherein the first relevance measure is determined depending on the probability that the user is aware of the first vehicle.

10. The method according to claim 9, further comprising determining a level of fatigue of the user based on the user-related data, wherein the probability that the user is aware of the first vehicle is determined depending on the level of fatigue.

11. The method according to claim 1, wherein the vehicle-related data comprises at least one of information about a location of the first vehicle, a speed of the first vehicle, a moving direction of the first vehicle, an itinerary of the first vehicle, or a distance of the vehicle relative to the user, wherein at least one of:

the first relevance measure is determined depending on at least one of the location of the first vehicle, the speed of the first vehicle, the moving direction of the first vehicle, the itinerary of the first vehicle, or the distance of the first vehicle relative to the user; or the first relevance measure is determined depending on a probability that a future location of the first vehicle is likely to coincide with a future location of the user.

12. The method according to claim 1, wherein the user-related data comprises at least one of rotation data indicative of a rotation of the user, ocular data indicative of an eye gaze movement of the user, or orientation data indicative of an orientation of the user, the method further comprising determining at least one of a direction of the rotation, the eye gaze movement, the orientation relative to a location of the first vehicle, a moving direction of the first vehicle, or an itinerary of the first vehicle, wherein the first relevance measure is determined to be indicative of a reduced value of the probability when the direction points toward at least one of the location of the first vehicle, the moving direction of the first vehicle, or the itinerary of the first vehicle.

13. The method according to claim 1, wherein the user-related data comprises orientation data indicative of an orientation of the user's head, the method further comprising determining a direction of the orientation of the user's head relative to the surface of the earth, wherein the first relevance measure is determined to be indicative of an increased value of the probability when the direction deviates from a direction parallel to the surface of the earth by more than a predefined angle.

14. The method according to claim 1, wherein the user-related data comprises at least one of movement data indicative of a movement of the user, walking data indicative of a walking activity of the user, cycling data indicative of a cycling activity of the user, skating data indicative of a skating activity of the user, or scooter data indicative of an activity of the user riding a scooter, wherein the method further comprises determining at least one of a direction, a speed of the movement, or a pattern of at least one of the walking activity, the cycling activity, the skating activity, or the activity of the user riding the scooter, wherein the first relevance measure is determined to be indicative of a reduced value of the probability when at least one of the direction, speed, or pattern changes and indicative of an increased value of the probability when the speed is determined to have a larger value as compared to when the speed is determined to have a smaller value.

15. The method according to claim 1, wherein at least one of the first vehicle-related data or the user-related data comprises sound data indicative of a sound detected in the ambient environment of the user, wherein the method further comprises determining whether the sound data contains a sound feature associated with a property of at least one of the first vehicle or a property of the user, wherein the first relevance measure is determined depending on the sound data containing the sound feature.

16. The method according to claim 15, wherein the sound feature is indicative of a sound emitted by the vehicle as detected by a sound detector stationary with the user, the method further comprising determining a frequency of the sound, wherein the first relevance measure is determined depending on the frequency of the sound.

17. The method according to claim 1, wherein the user-related data is first user-related data, the method further comprising providing second user-related data after controlling the operation, the second user-related data indicative of a reaction of the user to the operation; and determining, based on the second user-related data, a third relevance measure indicative of a probability that the user is endangered by the first vehicle.

18. A hearing system comprising:

a hearing device configured to be worn at an ear of a user; and an electronic device configured to be operated stationary with the user remote from the ear, the electronic device communicatively coupled to the hearing device, the hearing system including a processing unit configured to perform the method according to claim 1.

19. A hearing device configured to be worn at an ear of a user, the hearing device comprising a processing unit configured to perform the method according to claim 1.

* * * * *